United States Patent
Shelton, IV et al.

(10) Patent No.: US 10,568,621 B2
(45) Date of Patent: Feb. 25, 2020

(54) SURGICAL STAPLE BUTTRESS WITH INTEGRAL ADHESIVE FOR RELEASABLY ATTACHING TO A SURGICAL STAPLER

(71) Applicant: Ethicon Endo-Surgery, LLC, Guaynabo, PR (US)

(72) Inventors: Frederick E. Shelton, IV, Hillsboro, OH (US); Jason L. Harris, Lebanon, OH (US); Rao S. Bezwada, Whitehouse Station, NJ (US); Charles J. Scheib, Loveland, OH (US); Prudence A. Turner, Independence, KY (US)

(73) Assignee: Ethicon LLC, Guaynabo, PR (US)

( * ) Notice: Subject to any disclaimer, the term of this patent is extended or adjusted under 35 U.S.C. 154(b) by 884 days.

(21) Appl. No.: 14/667,961

(22) Filed: Mar. 25, 2015

(65) Prior Publication Data
US 2016/0278765 A1   Sep. 29, 2016

(51) Int. Cl.
*A61B 17/068*   (2006.01)

(52) U.S. Cl.
CPC .................................. *A61B 17/068* (2013.01)

(58) Field of Classification Search
None
See application file for complete search history.

(56) References Cited

U.S. PATENT DOCUMENTS

| | | | |
|---|---|---|---|
| 2,642,375 A | 6/1953 | Alfred et al. | |
| 4,805,823 A | 2/1989 | Rothfuss | |
| 5,263,629 A | 11/1993 | Trumbull et al. | |
| 5,397,324 A * | 3/1995 | Carroll ............. | A61B 17/07207 128/898 |
| 5,415,334 A | 5/1995 | Williamson et al. | |
| 5,465,895 A | 11/1995 | Knodel et al. | |
| 5,597,107 A | 1/1997 | Knodel et al. | |
| 5,632,432 A | 5/1997 | Schulze et al. | |
| 5,673,840 A | 10/1997 | Schulze et al. | |

(Continued)

FOREIGN PATENT DOCUMENTS

| | | |
|---|---|---|
| EP | 1 064 883 A1 | 1/2001 |
| EP | 2 008 595 A2 | 12/2008 |

(Continued)

OTHER PUBLICATIONS

U.S. Appl. No. 14/226,142.

(Continued)

*Primary Examiner* — Hemant Desai
*Assistant Examiner* — Tanzim Imam
(74) *Attorney, Agent, or Firm* — Frost Brown Todd LLC

(57) ABSTRACT

A surgical stapler end effector assembly comprises a staple cartridge, an anvil, and a buttress assembly. The staple cartridge comprises a plurality of staples and a deck. The staple cartridge is operable to drive the staples through the deck. The anvil is movable from an open position toward the staple cartridge to reach a closed position. The anvil includes an underside having staple forming surface configured to receive staples driven through the deck. The buttress assembly comprises a buttress body, an adhesive material, and a plurality of reinforcement strands. The reinforcement strands are configured to engage one or more staples fired through the buttress body.

16 Claims, 34 Drawing Sheets

(56) References Cited

U.S. PATENT DOCUMENTS

| | | | |
|---|---|---|---|
| 5,686,090 A | 11/1997 | Schilder et al. | |
| 5,704,534 A | 1/1998 | Huitema et al. | |
| 5,792,135 A | 8/1998 | Madhani et al. | |
| 5,814,055 A | 9/1998 | Knodel et al. | |
| 5,817,084 A | 10/1998 | Jensen | |
| 5,878,193 A | 3/1999 | Wang et al. | |
| 6,231,565 B1 | 5/2001 | Tovey et al. | |
| 6,325,810 B1 * | 12/2001 | Hamilton | A61B 17/07207 227/175.1 |
| 6,364,888 B1 | 4/2002 | Niemeyer et al. | |
| 6,783,524 B2 | 8/2004 | Anderson et al. | |
| 6,978,921 B2 | 12/2005 | Shelton et al. | |
| 7,000,818 B2 | 2/2006 | Shelton et al. | |
| 7,143,923 B2 | 12/2006 | Shelton et al. | |
| 7,303,108 B2 | 12/2007 | Shelton | |
| 7,367,485 B2 | 5/2008 | Shelton et al. | |
| 7,380,695 B2 | 6/2008 | Doll et al. | |
| 7,380,696 B2 | 6/2008 | Shelton et al. | |
| 7,404,508 B2 | 7/2008 | Smith et al. | |
| 7,434,715 B2 | 10/2008 | Shelton et al. | |
| 7,524,320 B2 | 4/2009 | Tierney et al. | |
| 7,691,098 B2 | 4/2010 | Wallace et al. | |
| 7,721,930 B2 | 5/2010 | Mckenna et al. | |
| 7,806,891 B2 | 10/2010 | Nowlin et al. | |
| 8,062,330 B2 * | 11/2011 | Prommersberger | A61B 17/07207 227/175.1 |
| 8,141,762 B2 | 3/2012 | Bedi et al. | |
| 8,210,411 B2 | 7/2012 | Yates et al. | |
| 8,371,491 B2 | 2/2013 | Huitema et al. | |
| 8,408,439 B2 | 4/2013 | Huang et al. | |
| 8,453,914 B2 | 6/2013 | Laurent et al. | |
| 8,479,969 B2 | 7/2013 | Shelton | |
| 8,573,461 B2 | 11/2013 | Shelton | |
| 8,573,465 B2 | 11/2013 | Shelton | |
| 8,602,288 B2 | 12/2013 | Shelton | |
| 8,616,431 B2 | 12/2013 | Timm et al. | |
| 8,783,541 B2 | 7/2014 | Shelton et al. | |
| 8,800,838 B2 | 8/2014 | Shelton | |
| 8,814,025 B2 | 8/2014 | Miller et al. | |
| 8,820,605 B2 | 9/2014 | Shelton | |
| 8,844,789 B2 | 9/2014 | Shelton et al. | |
| 8,899,464 B2 | 12/2014 | Hueil et al. | |
| 8,998,060 B2 | 4/2015 | Bruewer et al. | |
| 9,101,359 B2 | 8/2015 | Smith et al. | |
| 2008/0140115 A1 * | 6/2008 | Stopek | A61B 17/068 606/219 |
| 2008/0169328 A1 | 7/2008 | Shelton | |
| 2009/0206125 A1 * | 8/2009 | Huitema | A61B 17/07207 227/175.1 |
| 2012/0111920 A1 * | 5/2012 | Kostrzewski | A61B 17/07207 227/176.1 |
| 2012/0199632 A1 | 8/2012 | Spivey et al. | |
| 2012/0241492 A1 | 9/2012 | Shelton et al. | |
| 2012/0241493 A1 | 9/2012 | Baxter et al. | |
| 2012/0289979 A1 * | 11/2012 | Eskaros | A61B 17/07292 606/151 |
| 2013/0037596 A1 | 2/2013 | Bear et al. | |
| 2013/0062391 A1 | 3/2013 | Boudreaux et al. | |
| 2013/0068816 A1 | 3/2013 | Vasudevan et al. | |
| 2013/0075445 A1 | 3/2013 | Balek et al. | |
| 2013/0075446 A1 | 3/2013 | Wang et al. | |
| 2013/0075447 A1 | 3/2013 | Weisenburgh et al. | |
| 2013/0206813 A1 | 8/2013 | Nalagatla | |
| 2013/0214030 A1 * | 8/2013 | Aronhalt | A61B 17/0682 227/176.1 |
| 2013/0256367 A1 | 10/2013 | Scheib et al. | |
| 2013/0315963 A1 * | 11/2013 | Erneta | C08L 67/04 424/400 |
| 2014/0166721 A1 * | 6/2014 | Stevenson | A61B 17/068 227/176.1 |
| 2014/0166725 A1 * | 6/2014 | Schellin | A61B 17/064 227/178.1 |
| 2014/0166726 A1 | 6/2014 | Schellin et al. | |
| 2014/0239036 A1 | 8/2014 | Zerkle et al. | |
| 2014/0239037 A1 | 8/2014 | Boudreaux et al. | |
| 2014/0239038 A1 | 8/2014 | Leimbach et al. | |
| 2014/0239040 A1 | 8/2014 | Fanelli et al. | |
| 2014/0239041 A1 | 8/2014 | Zerkle et al. | |
| 2014/0239042 A1 | 8/2014 | Simms et al. | |
| 2014/0239043 A1 | 8/2014 | Simms et al. | |
| 2014/0239044 A1 | 8/2014 | Hoffman | |
| 2014/0239063 A1 | 8/2014 | Lewis et al. | |
| 2014/0243801 A1 | 8/2014 | Fanelli et al. | |
| 2014/0246473 A1 | 9/2014 | Auld | |
| 2014/0263563 A1 | 9/2014 | Stokes et al. | |
| 2016/0051296 A1 * | 2/2016 | Weinzweig | A61B 17/80 606/281 |

FOREIGN PATENT DOCUMENTS

| | | |
|---|---|---|
| EP | 2 589 345 A1 | 5/2013 |
| EP | 2 604 196 A2 | 6/2013 |
| EP | 2 786 718 A2 | 10/2014 |
| JP | 2008-508046 A | 3/2008 |
| JP | 2012-528678 A | 11/2012 |
| WO | WO 2006/023578 A2 | 3/2006 |

OTHER PUBLICATIONS

U.S. Appl. No. 14/300,804.
U.S. Appl. No. 14/300,811.
U.S. Appl. No. 14/314,108.
U.S. Appl. No. 14/314,125.
U.S. Appl. No. 14/498,070.
European Search Report, Partial, dated Jun. 24, 2016 for Application No. EP 16162059.6, 10 pgs.
European Search Report, Extended, and Written Opinion dated Sep. 30, 2016 for Application No. EP 16162059.6, 13 pgs.
International Search Report and Written Opinion dated Oct. 18, 2016 for Application No. PCT/US2016/022798, 18 pgs.
Chinese Office Action dated Oct. 29, 2019 for Application No. 201680030449.X, 11 pages.
Japanese Notification of Reasons for Refusal dated Dec. 3, 2019 for Application No. 2017-549712, 8 pages.

* cited by examiner

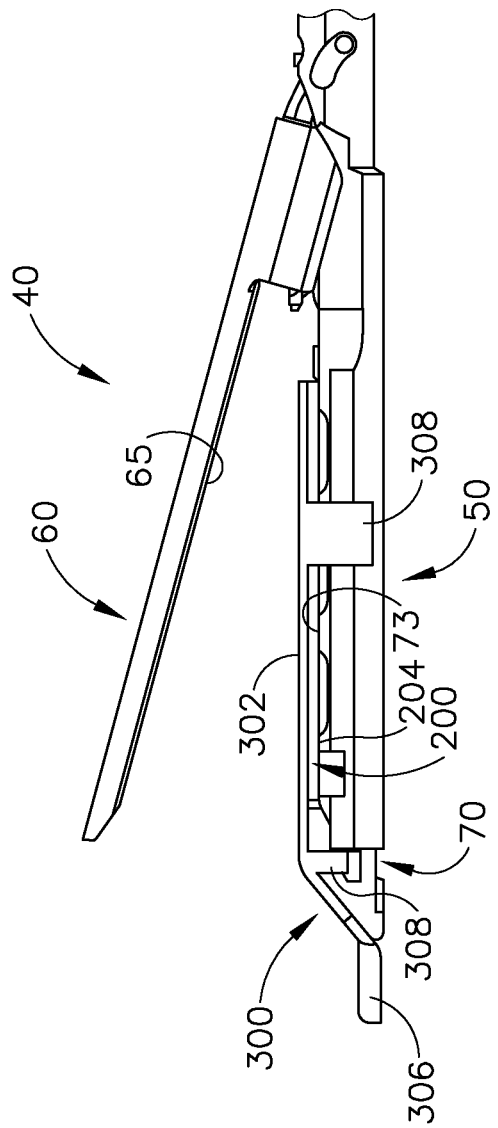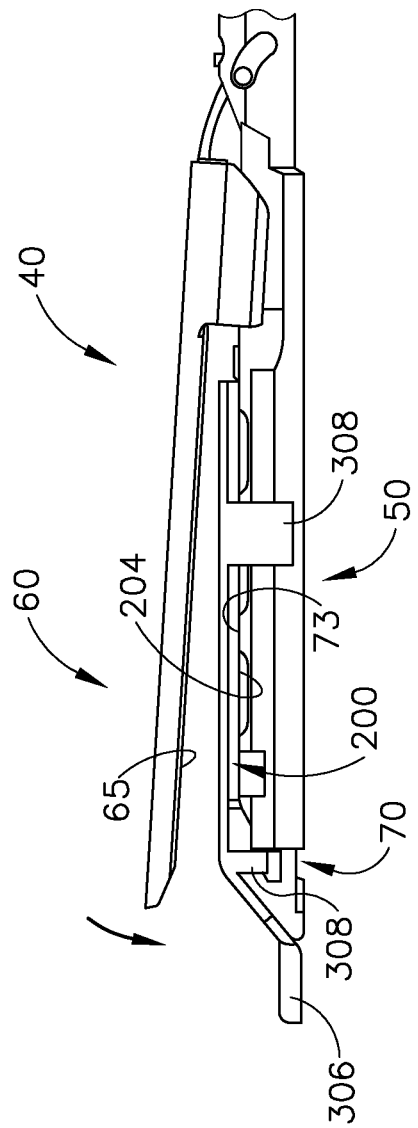

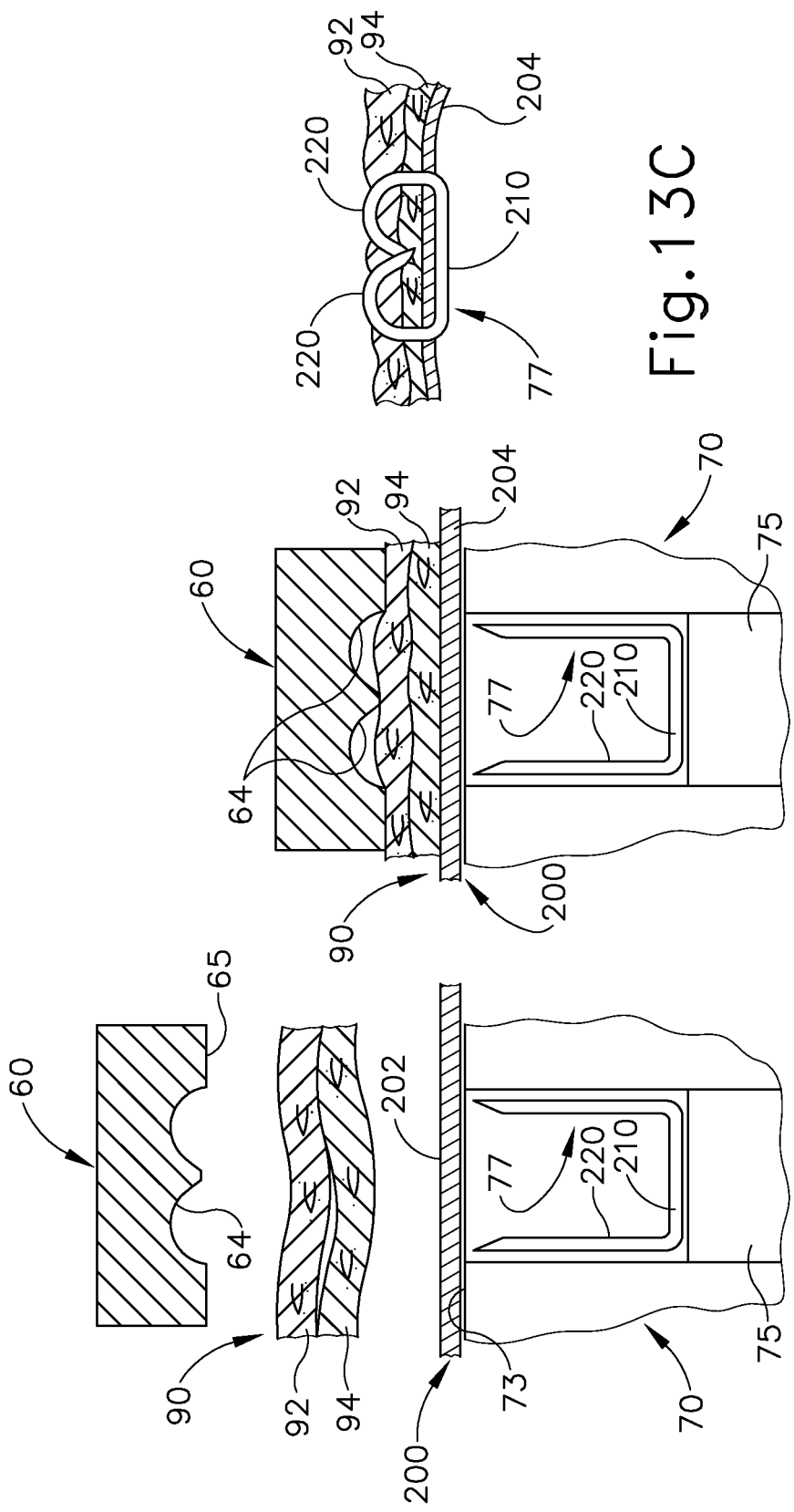

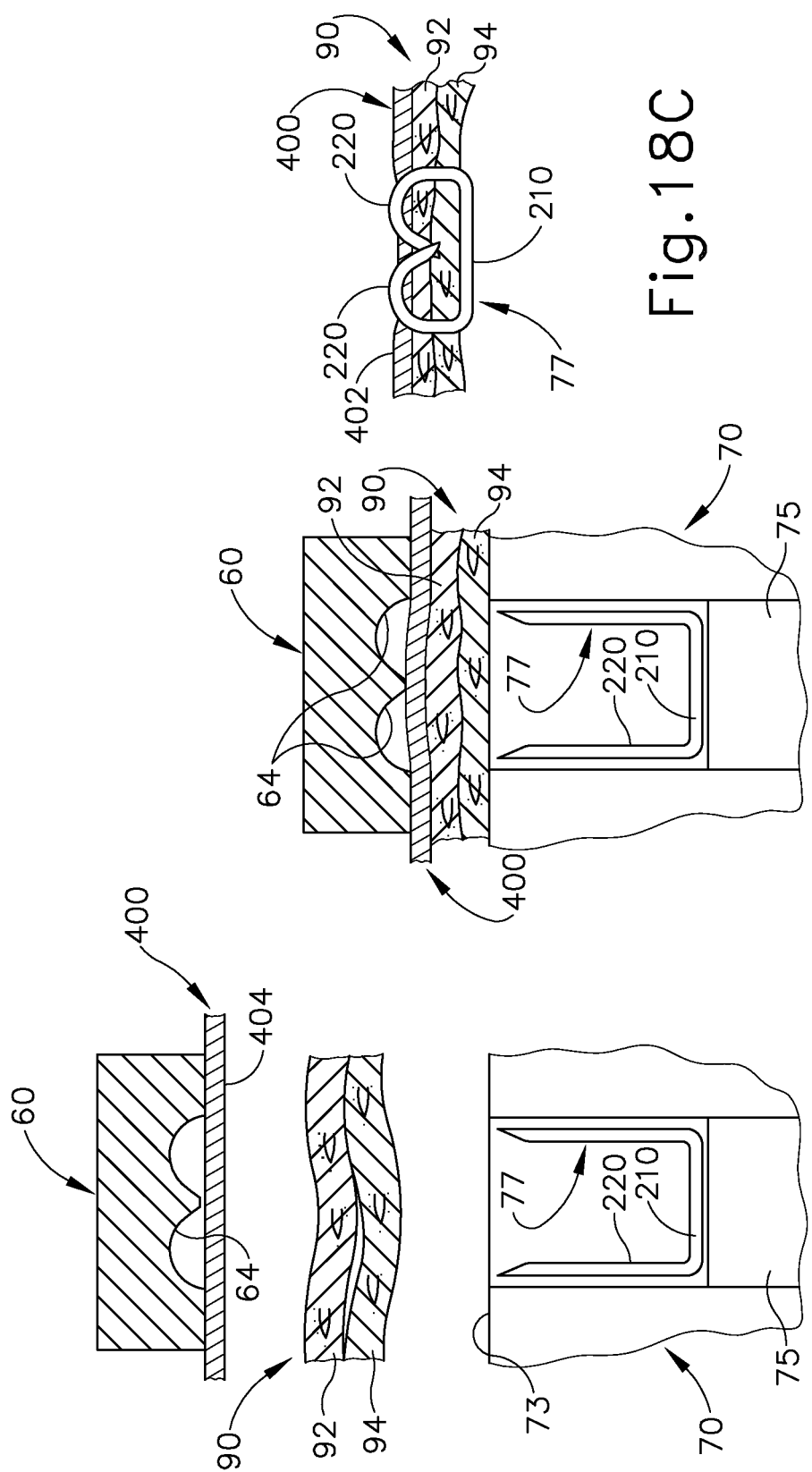

SURGICAL STAPLE BUTTRESS WITH INTEGRAL ADHESIVE FOR RELEASABLY ATTACHING TO A SURGICAL STAPLER

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasonic vibration, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. Patents is incorporated by reference herein.

While the surgical staplers referred to above are described as being used in endoscopic procedures, it should be understood that such surgical staplers may also be used in open procedures and/or other non-endoscopic procedures. By way of example only, a surgical stapler may be inserted through a thoracotomy, and thereby between a patient's ribs, to reach one or more organs in a thoracic surgical procedure that does not use a trocar as a conduit for the stapler. Such procedures may include the use of the stapler to sever and close a vessel leading to a lung. For instance, the vessels leading to an organ may be severed and closed by a stapler before removal of the organ from the thoracic cavity. Of course, surgical staplers may be used in various other settings and procedures.

Examples of surgical staplers that may be particularly suited or use through a thoracotomy are disclosed in U.S. Patent Pub. No. 2014/0243801, entitled "Surgical Instrument End Effector Articulation Drive with Pinion and Opposing Racks," published Aug. 28, 2014, issued as U.S. Pat. No. 9,186,142 on Nov. 17, 2015; U.S. Patent Pub. No. 2014/0239041, entitled "Lockout Feature for Movable Cutting Member of Surgical Instrument," published Aug. 28, 2014, issued as U.S. Pat. No. 9,717,497 on Aug. 1, 2017; U.S. Patent Pub. No. 2014/0239042, entitled "Integrated Tissue Positioning and Jaw Alignment Features for Surgical Stapler," published Aug. 28, 2014, issued as U.S. Pat. No. 9,517,065 on Dec. 13, 2016; U.S. Patent Pub. No. 2014/0239036, entitled "Jaw Closure Feature for End Effector of Surgical Instrument," published Aug. 28, 2014, issued as U.S. Pat. No. 9,839,421 on Dec. 12, 2017; U.S. Patent Pub. No. 2014/0239040, entitled "Surgical Instrument with Articulation Lock having a Detenting Binary Spring," published Aug. 28, 2014, issued as U.S. Pat. No. 9,867,615 on Jan. 16, 2018; U.S. Patent Pub. No. 2014/0239043, entitled "Distal Tip Features for End Effector of Surgical Instrument," published Aug. 28, 2014, issued as U.S. Pat. No. 9,622,746 on Apr. 18, 2017; U.S. Patent Pub. No. 2014/0239037, entitled "Staple Forming Features for Surgical Stapling Instrument," published Aug. 28, 2014, issued as U.S. Pat. No. 10,092,292 on Oct. 9, 2018; U.S. Patent Pub. No. 2014/0239038, entitled "Surgical Instrument with Multi-Diameter Shaft," published Aug. 28, 2014, issued as U.S. Pat. No. 9,795,379 on Oct. 24, 2017; and U.S. Patent Pub. No. 2014/0239044, entitled "Installation Features for Surgical Instrument End Effector Cartridge," published Aug. 28, 2014, issued as U.S. Pat. No. 9,808,248 on Nov. 7, 2017. The disclosure of each of the above-cited U.S. Patent Publications is incorporated by reference herein.

Additional surgical stapling instruments are disclosed in U.S. Pat. No. 8,141,762, entitled "Surgical Stapler Comprising a Staple Pocket," issued Mar. 27, 2012; U.S. Pat. No. 8,371,491, entitled "Surgical End Effector Having Buttress Retention Features," issued Feb. 12, 2013; U.S. Pub. No. 2014/0263563, entitled "Method and Apparatus for Sealing End-to-End Anastomosis" published Sep. 18, 2014, issued as U.S. Pat. No. 9,597,082 on Mar. 21, 2017; U.S. Pub. No. 2014/0246473, entitled "Rotary Powered Surgical Instruments with Multiple Degrees of Freedom," published Sep. 4, 2014, issued as U.S. Pat. No. 9,398,911 on Jul. 26, 2016; U.S. Pub. No. 2013/0206813, entitled "Linear Stapler," published Aug. 15, 2013, now abandoned; U.S. Pub. No. 2008/0169328, entitled "Buttress Material for Use with a Surgical Stapler," published Jul. 17, 2008, now abandoned; U.S. patent application Ser. No. 14/300,804, entitled "Woven and Fibrous Materials for Reinforcing a Staple Line," filed Jun. 10, 2014, issued as U.S. Pat. No. 9,848,871 on Dec. 26, 2017; U.S. patent application Ser. No. 14/300,811, entitled "Devices and Methods for Sealing Staples in Tissue," issued as U.S. Pat. No. 9,936,954 on Apr. 10, 2018; and U.S. patent application Ser. No. 14/498,070, entitled "Circular Fastener Cartridges for Applying Radially Expendable Fastener Lines" filed Sep. 26, 2014, issued as U.S. Pat. No. 10,426,476 on Oct. 1, 2019. The disclosure of each of the above-cited U.S. Patents, U.S. Patent Publications, and U.S. Patent Applications is incorporated by reference herein.

In some instances, it may be desirable to equip a surgical stapling instrument with a buttress material to reinforce the mechanical fastening of tissue provided by staples. Such a buttress may prevent the applied staples from pulling through tissue and may otherwise reduce a risk of tissue tearing at or near the site of applied staples.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 12B depicts a side elevational view of the buttress and retainer of FIG. 10 engaging the end effector of FIG. 3, with the anvil of the end effector in an open position;

FIG. 12C depicts a side elevational view of the buttress and retainer of FIG. 10 engaging the end effector of FIG. 3, with the anvil of the end effector moving toward a closed position;

FIG. 13A depicts a cross-sectional view of a portion of the end effector and buttress assembly of FIG. 12D, with tissue positioned between the buttress and the anvil, and with the anvil in an open position;

FIG. 13B depicts a cross-sectional view of a portion of the end effector and buttress assembly of FIG. 12D, with tissue positioned between the buttress and the anvil, and with the anvil in a closed position;

FIG. 13C depicts a cross-sectional view of a staple and the buttress of FIG. 12D being secured to tissue by the end effector of FIG. 12D;

FIG. 18A depicts a cross-sectional view of a portion of the end effector and buttress assembly of FIG. 17B, with tissue positioned between the buttress and the staple cartridge, and with the anvil in an open position;

FIG. 18B depicts a cross-sectional view of a portion of the end effector and buttress assembly of FIG. 17B, with tissue positioned between the buttress and the staple cartridge, and with the anvil in a closed position;

FIG. 18C depicts a cross-sectional view of a staple and the buttress of FIG. 17B being secured to tissue by the end effector of FIG. 17B;

Figure 1:
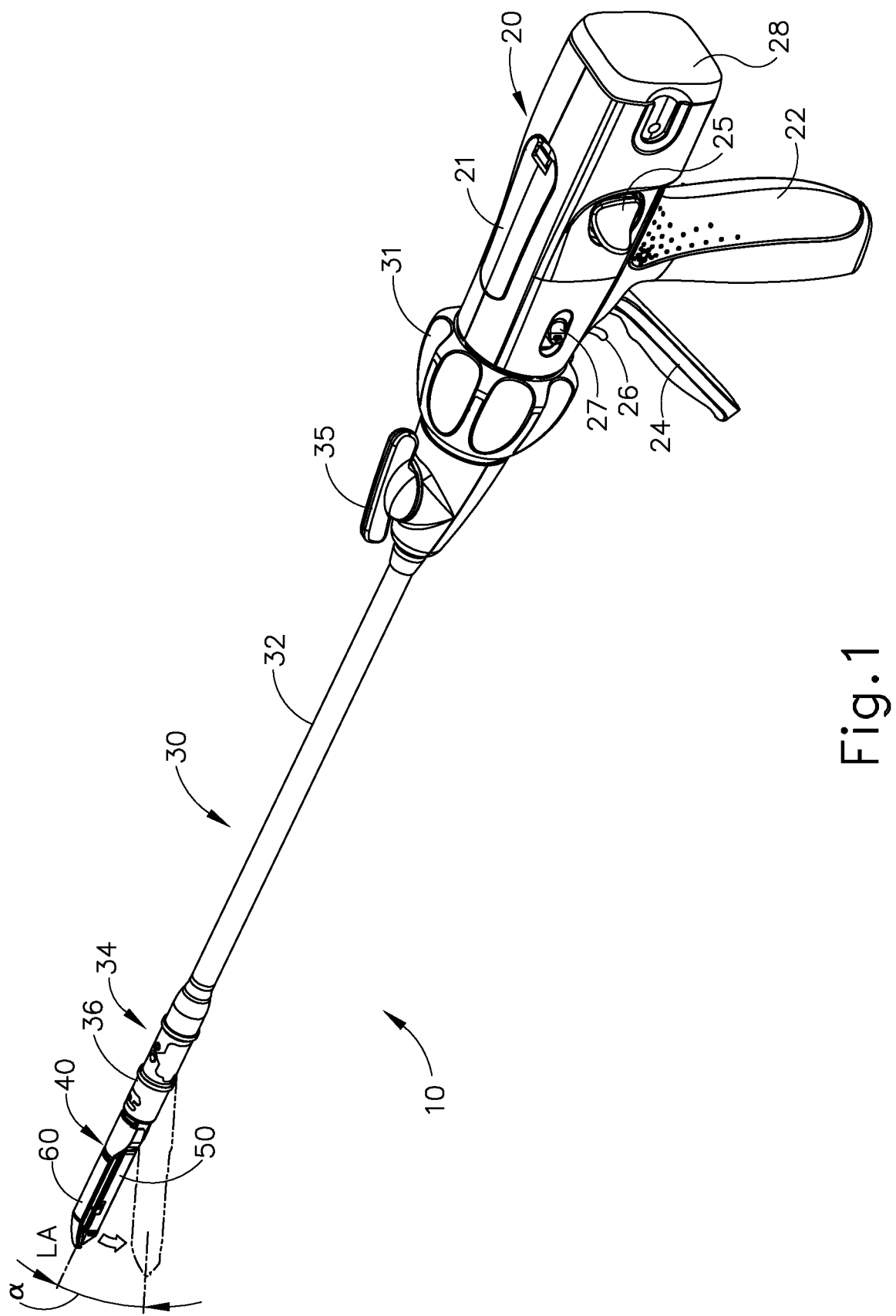
FIG. 1 depicts a perspective view of an exemplary articulating surgical stapling instrument.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Exemplary Surgical Stapler

FIG. 1 depicts an exemplary surgical stapling and severing instrument (10) that includes a handle assembly (20), a shaft assembly (30), and an end effector (40). End effector (40) and the distal portion of shaft assembly (30) are sized for insertion, in a nonarticulated state as depicted in FIG. 1, through a trocar cannula to a surgical site in a patient for performing a surgical procedure. By way of example only, such a trocar may be inserted in a patient's abdomen, between two of the patient's ribs, or elsewhere. In some settings, instrument (10) is used without a trocar. For instance, end effector (40) and the distal portion of shaft assembly (30) may be inserted directly through a thoracotomy or other type of incision. It should be understood that terms such as "proximal" and "distal" are used herein with reference to a clinician gripping handle assembly (20) of instrument (10). Thus, end effector (40) is distal with respect to the more proximal handle assembly (20). It will be further appreciated that for convenience and clarity, spatial terms such as "vertical" and "horizontal" are used herein with respect to the drawings. However, surgical instruments are used in many orientations and positions, and these terms are not intended to be limiting and absolute.

A. Exemplary Handle Assembly and Shaft Assembly

Figure 2:
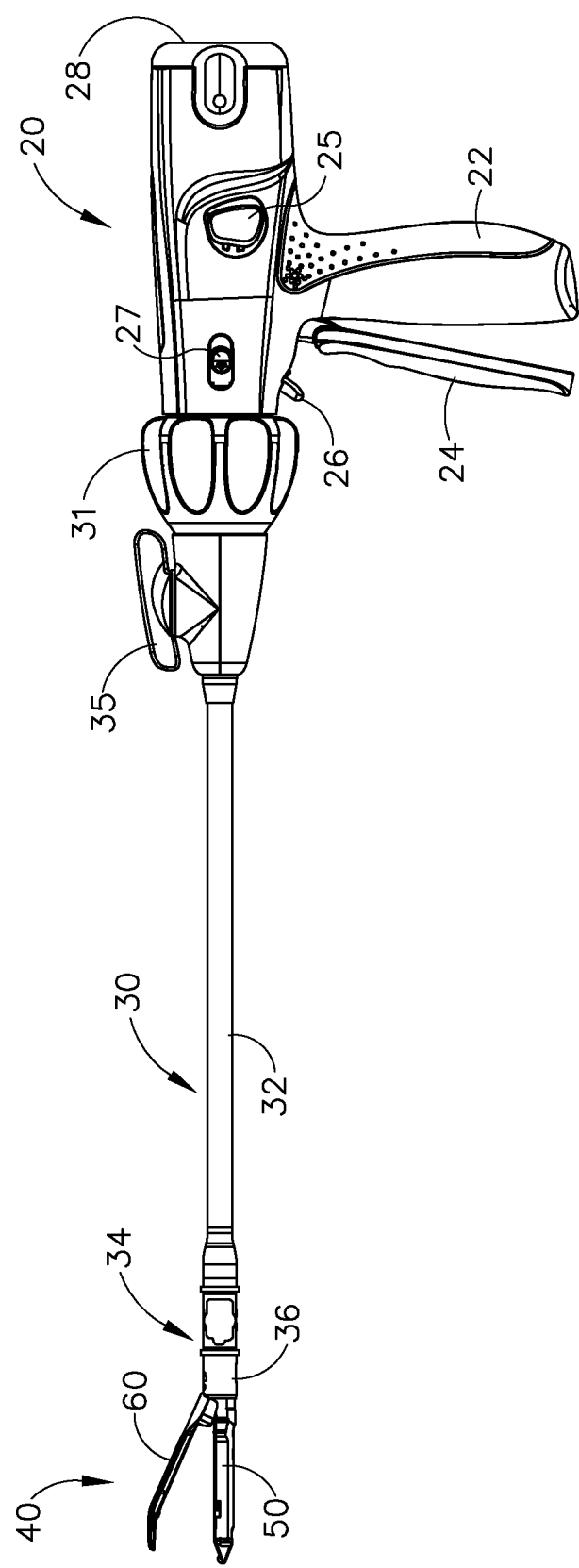
FIG. 2 depicts a side elevational view of the instrument of FIG. 1.

As shown in FIGS. 1-2, handle assembly (20) of the present example comprises pistol grip (22), a closure trigger (24), and a firing trigger (26). Each trigger (24, 26) is selectively pivotable toward and away from pistol grip (22) as will be described in greater detail below. Handle assembly (20) further includes an anvil release button (25), a firing beam reverse switch (27), and a removable battery pack (28). These components will also be described in greater detail below. Of course, handle assembly (20) may have a variety of other components, features, and operabilities, in addition to or in lieu of any of those noted above. Other suitable configurations for handle assembly (20) will be apparent to those of ordinary skill in the art in view of the teachings herein.

Figure 3:
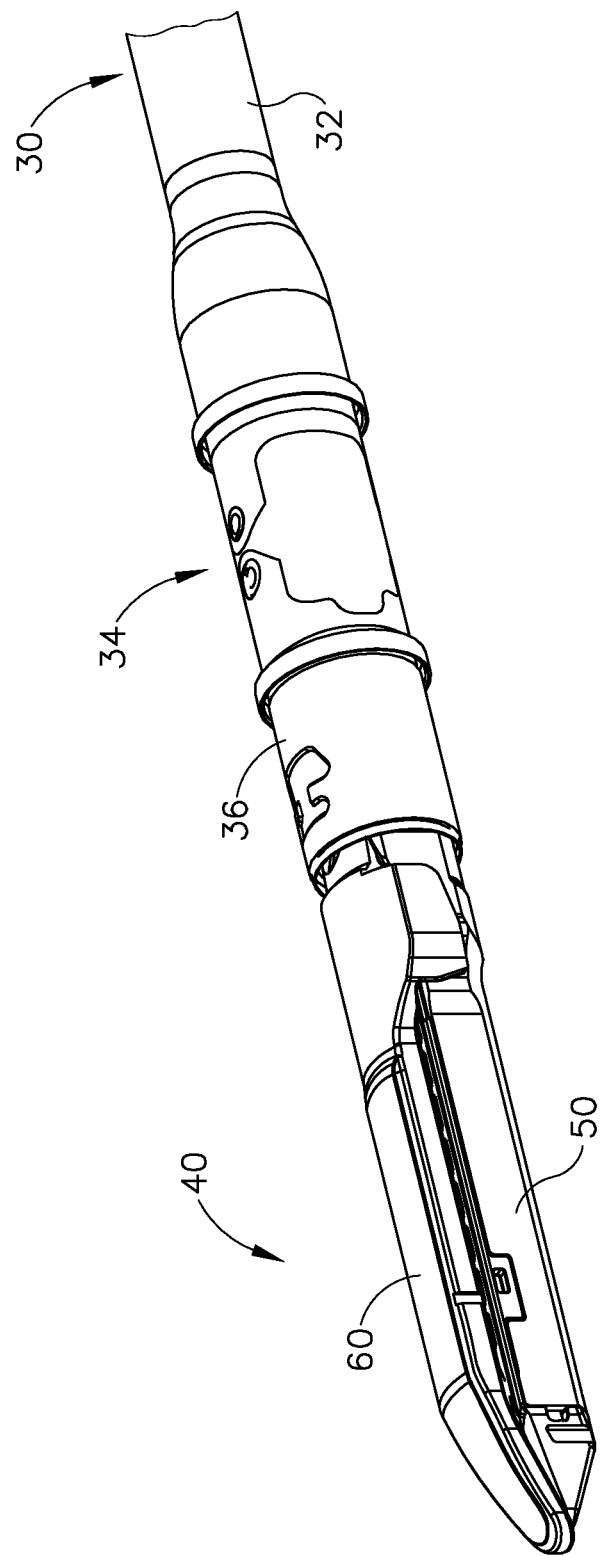
FIG. 3 depicts a perspective view of an end effector of the instrument of FIG. 1, with the end effector in a closed configuration.

As shown in FIGS. 1-3, shaft assembly (30) of the present example comprises an outer closure tube (32), an articulation section (34), and a closure ring (36), which is further coupled with end effector (40). Closure tube (32) extends along the length of shaft assembly (30). Closure ring (36) is positioned distal to articulation section (34). Closure tube (32) and closure ring (36) are configured to translate longitudinally relative to handle assembly (20). Longitudinal translation of closure tube (32) is communicated to closure ring (36) via articulation section (34). Exemplary features that may be used to provide longitudinal translation of closure tube (32) and closure ring (36) will be described in greater detail below.

Articulation section (34) is operable to laterally deflect closure ring (36) and end effector (40) laterally away from the longitudinal axis (LA) of shaft assembly (30) at a desired angle (α). End effector (40) may thereby reach behind an organ or approach tissue from a desired angle or for other reasons. In some versions, articulation section (34) enables deflection of end effector (40) along a single plane. In some other versions, articulation section (34) enables deflection of end effector along more than one plane. In the present example, articulation is controlled through an articulation control knob (35) which is located at the proximal end of shaft assembly (30). Knob (35) is rotatable about an axis that is perpendicular to the longitudinal axis (LA) of shaft assembly (30). Closure ring (36) and end effector (40) pivot about an axis that is perpendicular to the longitudinal axis (LA) of shaft assembly (30) in response to rotation of knob (35). By way of example only, rotation of knob (35) clockwise may cause corresponding clockwise pivoting of closure ring (36) and end effector (40) at articulation section (34). Articulation section (34) is configured to communicate longitudinal translation of closure tube (32) to closure ring (36), regardless of whether articulation section (34) is in a straight configuration or an articulated configuration.

In some versions, articulation section (34) and/or articulation control knob (35) are/is constructed and operable in accordance with at least some of the teachings of U.S. Pub. No. 2014/0243801, entitled "Surgical Instrument End Effector Articulation Drive with Pinion and Opposing Racks," published Aug. 28, 2014, issued as U.S. Pat. No. 9,186,142 on Nov. 17, 2015, the disclosure of which is incorporated by reference herein. Articulation section (34) may also be constructed and operable in accordance with at least some of the teachings of U.S. patent application Ser. No. 14/314,125, entitled "Articulation Drive Features for Surgical Stapler," filed Jun. 25, 2014, issued as U.S. Pat. No. 10,292,701 on May 21, 2019, the disclosure of which is incorporated by reference herein; and/or in accordance with the various teachings below. Other suitable forms that articulation section (34) and articulation knob (35) may take will be apparent to those of ordinary skill in the art in view of the teachings herein.

As shown in FIGS. 1-2, shaft assembly (30) of the present example further includes a rotation knob (31). Rotation knob (31) is operable to rotate the entire shaft assembly (30) and end effector (40) relative to handle assembly (20) about the longitudinal axis (LA) of shaft assembly (30). In some versions, rotation knob (31) is operable to selectively lock the angular position of shaft assembly (30) and end effector (40) relative to handle assembly (20) about the longitudinal axis (LA) of shaft assembly (30). For instance, rotation knob (31) may be translatable between a first longitudinal position, in which shaft assembly (30) and end effector (40) are rotatable relative to handle assembly (20) about the longitudinal axis (LA) of shaft assembly (30); and a second longitudinal position, in which shaft assembly (30) and end effector (40) are not rotatable relative to handle assembly (20) about the longitudinal axis (LA) of shaft assembly (30). Of course, shaft assembly (30) may have a variety of other components, features, and operabilities, in addition to or in lieu of any of those noted above. By way of example only, at least part of shaft assembly (30) is constructed in accordance with at least some of the teachings of U.S. Pub. No. 2014/0239038, entitled "Surgical Instrument with Multi-Diameter Shaft," published Aug. 28, 2014, issued as U.S. Pat. No. 9,795,379 on Oct. 24, 2017, the disclosure of which is incorporated by reference herein. Other suitable configurations for shaft assembly (30) will be apparent to those of ordinary skill in the art in view of the teachings herein.

B. Exemplary End Effector

As also shown in FIGS. 1-3, end effector (40) of the present example includes a lower jaw (50) and a pivotable anvil (60). Anvil (60) includes a pair of integral, outwardly extending pins (66) that are disposed in corresponding curved slots (54) of lower jaw (50). Pins (66) and slots (54) are shown in FIG. 5. Anvil (60) is pivotable toward and away from lower jaw (50) between an open position (shown in FIGS. 2 and 4) and a closed position (shown in FIGS. 1, 3, and 7A-7B). Use of the term "pivotable" (and similar terms with "pivot" as a base) should not be read as necessarily requiring pivotal movement about a fixed axis. For instance, in the present example, anvil (60) pivots about an axis that is defined by pins (66), which slide along curved slots (54) of lower jaw (50) as anvil (60) moves toward lower jaw (50). In such versions, the pivot axis translates along the path defined by slots (54) while anvil (60) simultaneously pivots about that axis. In addition or in the alternative, the pivot axis may slide along slots (54) first, with anvil (60) then pivoting about the pivot axis after the pivot axis has slid a certain distance along the slots (54). It should be understood that such sliding/translating pivotal movement is encompassed within terms such as "pivot," "pivots," "pivotal," "pivotable," "pivoting," and the like. Of course, some versions may provide pivotal movement of anvil (60) about an axis that remains fixed and does not translate within a slot or channel, etc.

As best seen in FIG. 5, lower jaw (50) of the present example defines a channel (52) that is configured to receive a staple cartridge (70). Staple cartridge (70) may be inserted into channel (52), end effector (40) may be actuated, and then staple cartridge (70) may be removed and replaced with another staple cartridge (70). Lower jaw (50) thus releasably retains staple cartridge (70) in alignment with anvil (60) for actuation of end effector (40). In some versions, lower jaw (50) is constructed in accordance with at least some of the teachings of U.S. Pub. No. 2014/0239044, entitled "Installation Features for Surgical Instrument End Effector Cartridge," published Aug. 28, 2014, issued as U.S. Pat. No. 9,808,248 on Nov. 7, 2017, the disclosure of which is incorporated by reference herein. Other suitable forms that lower jaw (50) may take will be apparent to those of ordinary skill in the art in view of the teachings herein.

Figure 4:
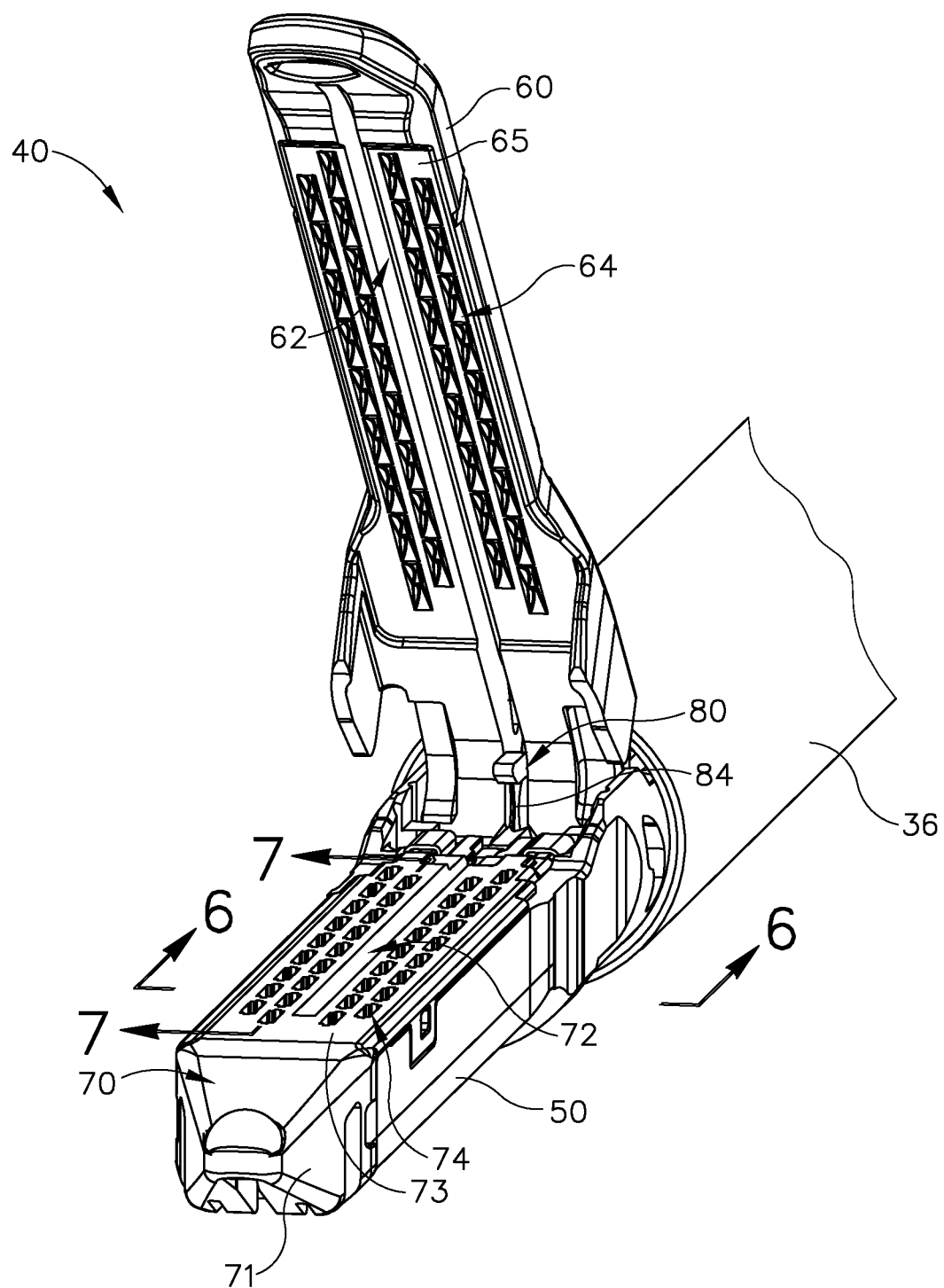
FIG. 4 depicts a perspective view of the end effector of FIG. 3, with the end effector in an open configuration.
Figure 5:
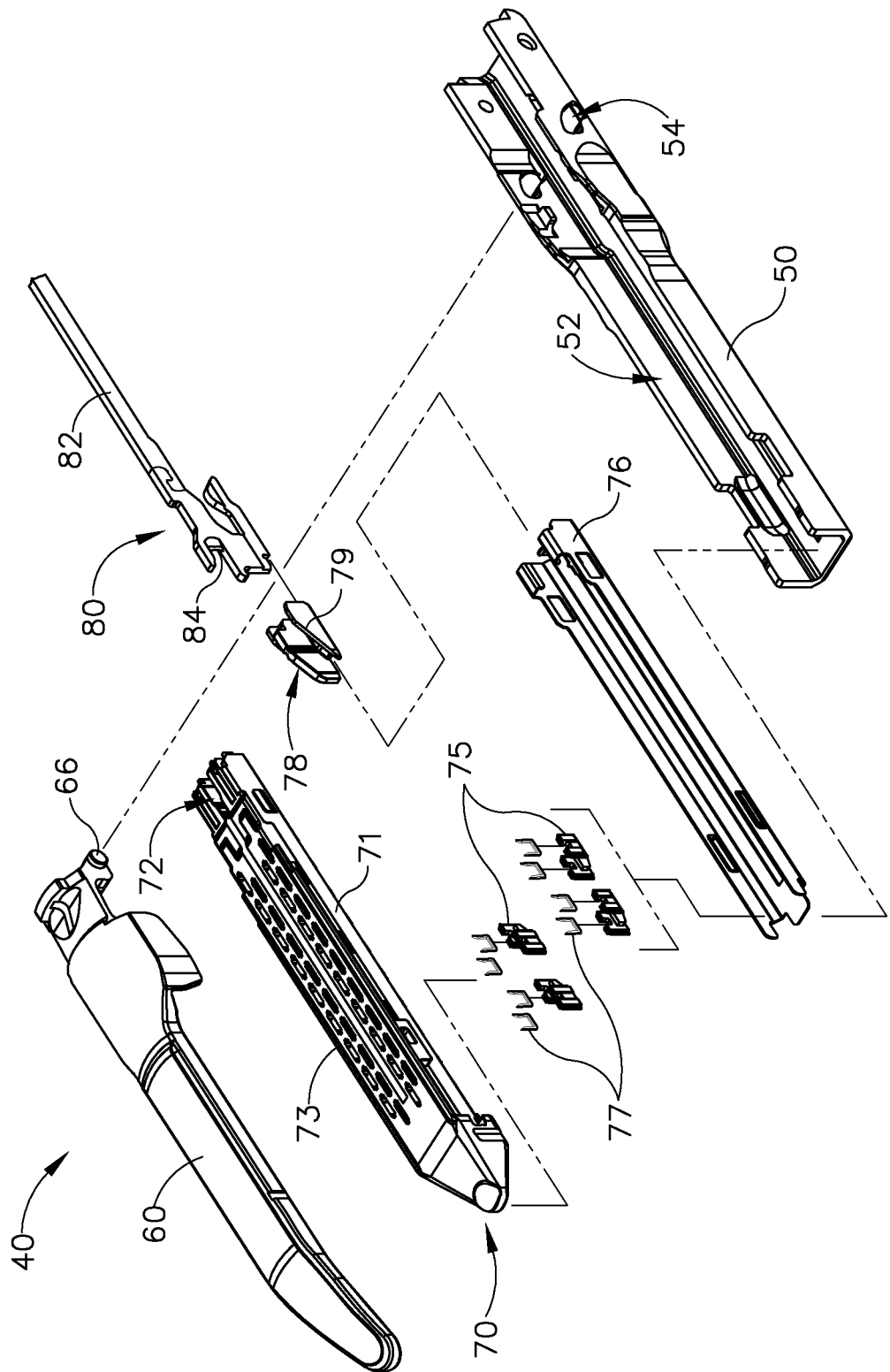
FIG. 5 depicts an exploded perspective view of the end effector of FIG. 3.
Figure 6:
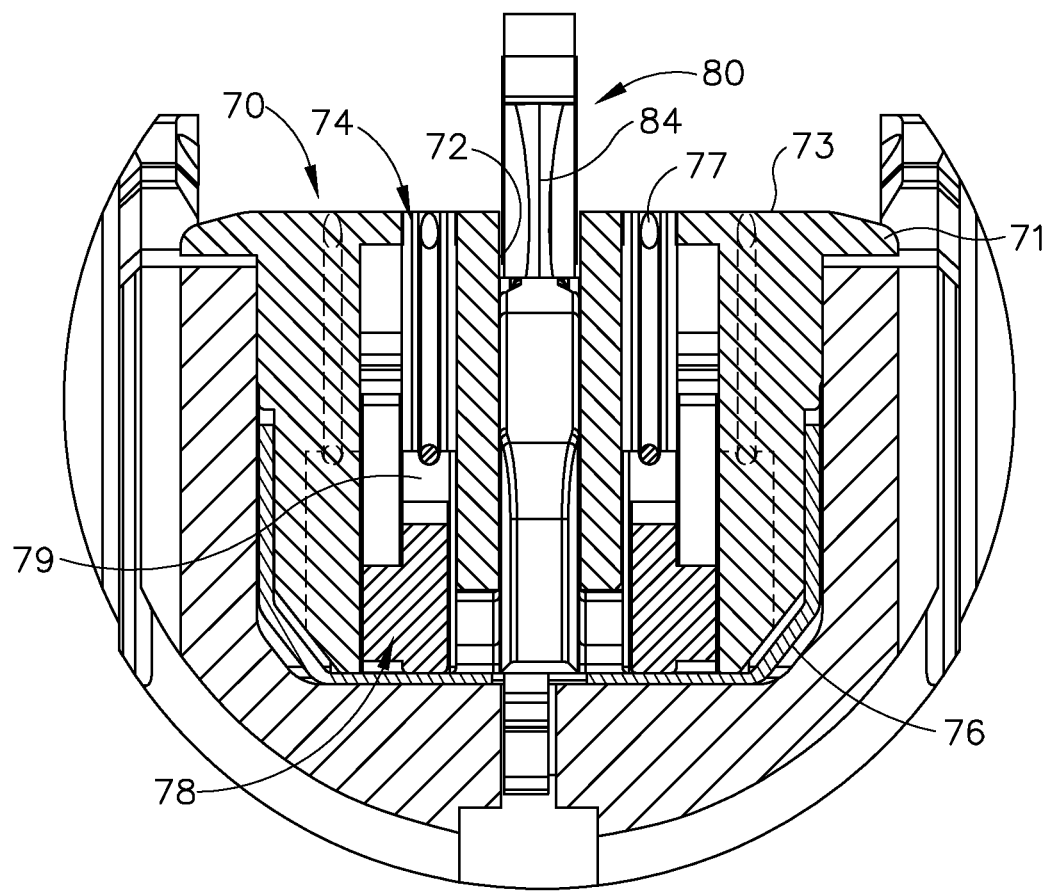
FIG. 6 depicts a cross-sectional end view of the end effector of FIG. 3, taken along line 6-6 of FIG. 4.
Figure 7A:
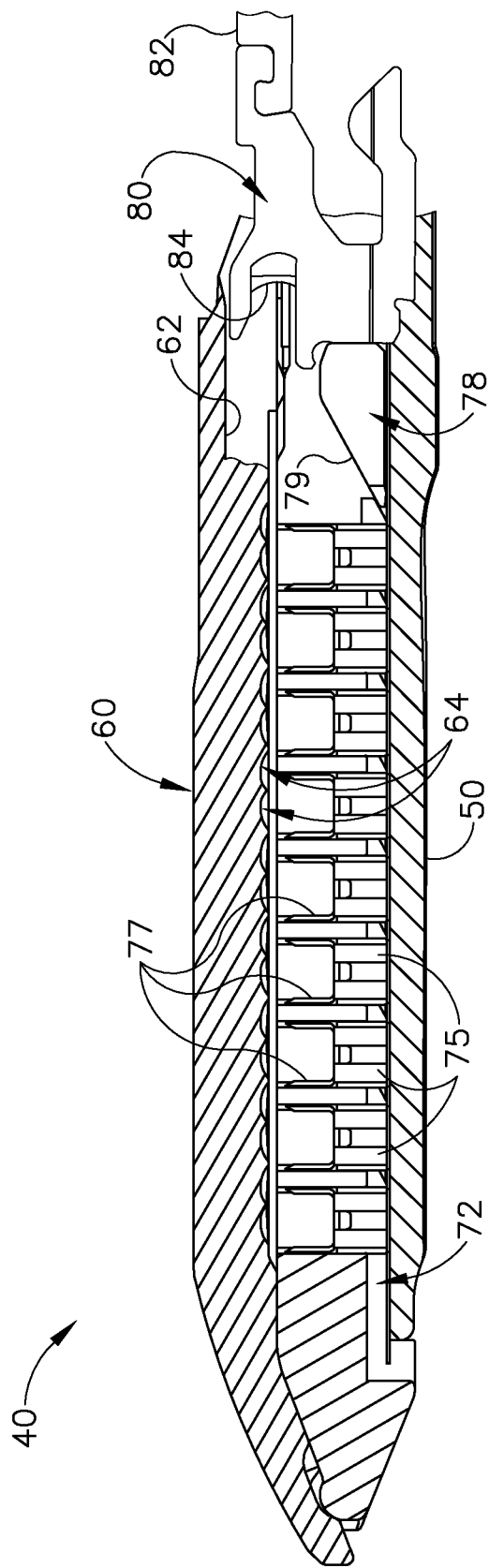
FIG. 7A depicts a cross-sectional side view of the end effector of FIG. 3, taken along line 7-7 of FIG. 4, with a firing beam in a proximal position.

As best seen in FIGS. 4-6, staple cartridge (70) of the present example comprises a cartridge body (71) and a tray (76) secured to the underside of cartridge body (71). The upper side of cartridge body (71) presents a deck (73), against which tissue may be compressed when anvil (60) is in a closed position. Cartridge body (71) further defines a longitudinally extending channel (72) and a plurality of staple pockets (74). A staple (77) is positioned in each staple pocket (74). A staple driver (75) is also positioned in each staple pocket (74), underneath a corresponding staple (77), and above tray (76). As will be described in greater detail below, staple drivers (75) are operable to translate upwardly in staple pockets (74) to thereby drive staples (77) upwardly through staple pockets (74) and into engagement with anvil (60). Staple drivers (75) are driven upwardly by a wedge sled (78), which is captured between cartridge body (71) and tray (76), and which translates longitudinally through cartridge body (71). Wedge sled (78) includes a pair of obliquely angled cam surfaces (79), which are configured to engage staple drivers (75) and thereby drive staple drivers (75) upwardly as wedge sled (78) translates longitudinally through cartridge (70). For instance, when wedge sled (78) is in a proximal position as shown in FIG. 7A, staple drivers (75) are in downward positions and staples (77) are located in staple pockets (74). As wedge sled (78) is driven to the distal position shown in FIG. 7B by a translating knife member (80), wedge sled (78) drives staple drivers (75) upwardly, thereby driving staples (77) out of staple pockets (74) and into staple forming pockets (64) that are formed in the underside (65) of anvil (60). Thus, staple drivers (75) translate along a vertical dimension as wedge sled (78) translates along a horizontal dimension.

It should be understood that the configuration of staple cartridge (70) may be varied in numerous ways. For instance, staple cartridge (70) of the present example includes two longitudinally extending rows of staple pockets (74) on one side of channel (72); and another set of two longitudinally extending rows of staple pockets (74) on the other side of channel (72). However, in some other versions, staple cartridge (70) includes three, one, or some other number of staple pockets (74) on each side of channel (72). In some versions, staple cartridge (70) is constructed and operable in accordance with at least some of the teachings of U. U.S. patent application Ser. No. 13/780,106, entitled "Integrated Tissue Positioning and Jaw Alignment Features for Surgical Stapler," filed Feb. 28, 2013, issued as U.S. Pat. No. 9,517,065 on Dec. 13, 2016, the disclosure of which is incorporated by reference herein. In addition or in the alternative, staple cartridge (70) may be constructed and operable in accordance with at least some of the teachings of U.S. Pub. No. 2014/0239044, entitled "Installation Features for Surgical Instrument End Effector Cartridge," published Aug. 28, 2014, issued as U.S. Pat. No. 9,808,248 on Nov. 7, 2017, the disclosure of which is incorporated by reference herein. Other suitable forms that staple cartridge (70) may take will be apparent to those of ordinary skill in the art in view of the teachings herein.

As best seen in FIG. 4, anvil (60) of the present example comprises a longitudinally extending channel (62) and a plurality of staple forming pockets (64). Channel (62) is configured to align with channel (72) of staple cartridge (70) when anvil (60) is in a closed position. Each staple forming pocket (64) is positioned to lie over a corresponding staple pocket (74) of staple cartridge (70) when anvil (60) is in a closed position. Staple forming pockets (64) are configured to deform the legs of staples (77) when staples (77) are driven through tissue and into anvil (60). In particular, staple forming pockets (64) are configured to bend the legs of staples (77) to secure the formed staples (77) in the tissue. Anvil (60) may be constructed in accordance with at least some of the teachings of U.S. Pub. No. 2014/0239042, entitled "Integrated Tissue Positioning and Jaw Alignment Features for Surgical Stapler," published Aug. 28, 2014, issued as U.S. Pat. No. 9,517,065 on Dec. 13, 2016; at least some of the teachings of U.S. Pub. No. 2014/0239036, entitled "Jaw Closure Feature for End Effector of Surgical Instrument," published Aug. 28, 2014, issued as U.S. Pat. No. 9,839,421 on Dec. 12, 2017; and/or at least some of the teachings of U.S. Pub. No. 2014/0239037, entitled "Staple Forming Features for Surgical Stapling Instrument," published Aug. 28, 2014, issued as U.S. Pat. No. 10,092,292 on Oct. 9, 2018, the disclosure of which is incorporated by reference herein. Other suitable forms that anvil (60) may take will be apparent to those of ordinary skill in the art in view of the teachings herein.

Figure 7B:
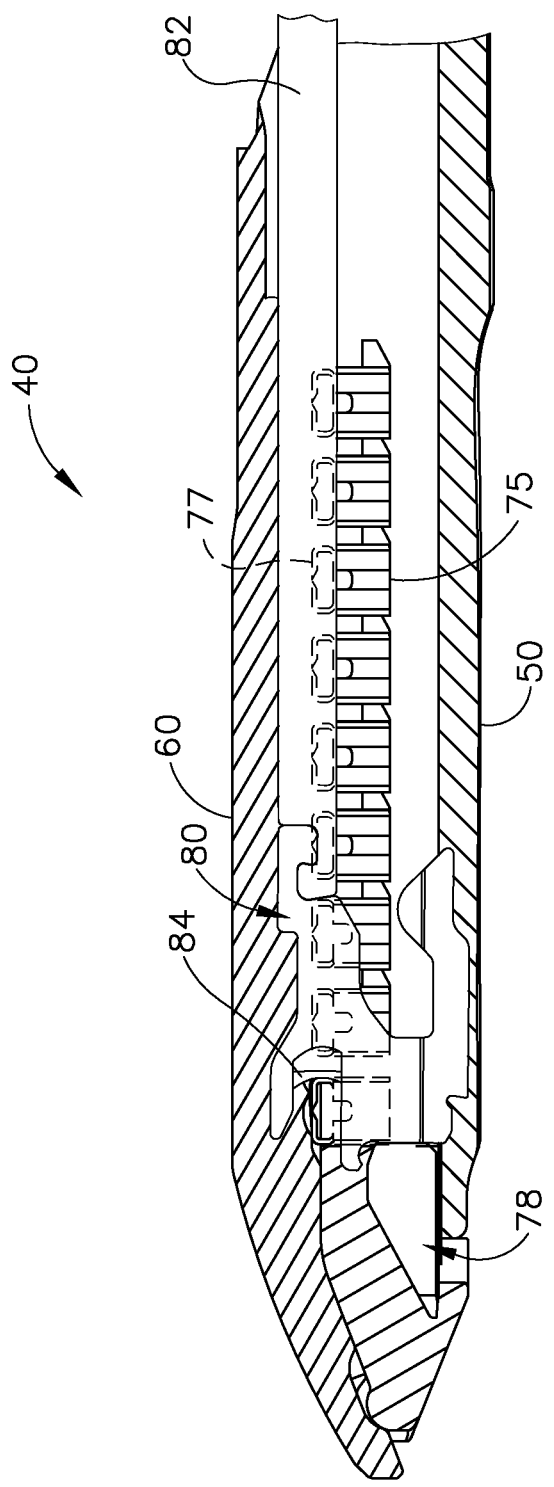
FIG. 7B depicts a cross-sectional side view of the end effector of FIG. 3, taken along line 7-7 of FIG. 4, with the firing beam in a distal position.

In the present example, a knife member (80) is configured to translate through end effector (40). As best seen in FIGS. 5 and 7A-7B, knife member (80) is secured to the distal end of a firing beam (82), which extends through a portion of shaft assembly (30). As best seen in FIGS. 4 and 6, knife member (80) is positioned in channels (62, 72) of anvil (60) and staple cartridge (70). Knife member (80) includes a distally presented cutting edge (84) that is configured to sever tissue that is compressed between anvil (60) and deck (73) of staple cartridge (70) as knife member (80) translates distally through end effector (40). As noted above and as shown in FIGS. 7A-7B, knife member (80) also drives wedge sled (78) distally as knife member (80) translates distally through end effector (40), thereby driving staples (77) through tissue and against anvil (60) into formation. Various features that may be used to drive knife member (80) distally through end effector (40) will be described in greater detail below.

In some versions, end effector (40) includes lockout features that are configured to prevent knife member (80) from advancing distally through end effector (40) when a staple cartridge (70) is not inserted in lower jaw (50). In addition or in the alternative, end effector (40) may include lockout features that are configured to prevent knife member (80) from advancing distally through end effector (40) when a staple cartridge (70) that has already been actuated once (e.g., with all staples (77) deployed therefrom) is inserted in lower jaw (50). By way of example only, such lockout features may be configured in accordance with at least some of the teachings of U.S. Pub. No. 2014/0239041, entitled "Lockout Feature for Movable Cutting Member of Surgical Instrument," published Aug. 28, 2014, issued as U.S. Pat. No. 9,717,497 on Aug. 1, 2017, the disclosure of which is incorporated by reference herein; and/or at least some of the teachings of U.S. patent application Ser. No. 14/314,108, entitled "Method of Using Lockout Features for Surgical Stapler Cartridge," filed on Jun. 25, 2014, issued as U.S. Pat. No. 10,335,147 on Jul. 2, 2019, the disclosure of which is incorporated by reference herein. Other suitable forms that lockout features may take will be apparent to those of ordinary skill in the art in view of the teachings herein. Alternatively, end effector (40) may simply omit such lockout features.

C. Exemplary Actuation of Anvil

In the present example, anvil (60) is driven toward lower jaw (50) by advancing closure ring (36) distally relative to end effector (40). Closure ring (36) cooperates with anvil (60) through a camming action to drive anvil (60) toward lower jaw (50) in response to distal translation of closure ring (36) relative to end effector (40). Similarly, closure ring (36) may cooperate with anvil (60) to open anvil (60) away from lower jaw (50) in response to proximal translation of closure ring (36) relative to end effector (40). By way of example only, closure ring (36) and anvil (60) may interact in accordance with at least some of the teachings of U.S. Pub. No. 2014/0239036, entitled "Jaw Closure Feature for End Effector of Surgical Instrument," published Aug. 28, 2014, issued as U.S. Pat. No. 9,839,421 on Dec. 12, 2017, the disclosure of which is incorporated by reference herein; and/or in accordance with at least some of the teachings of U.S. patent application Ser. No. 14/314,108, entitled "Method of Using Lockout Features for Surgical Stapler Cartridge," filed on Jun. 25, 2014, issued as U.S. Pat. No. 10,335,147 on Jul. 2, 2019, the disclosure of which is incorporated by reference herein. Exemplary features that may be used to provide longitudinal translation of closure ring (36) relative to end effector (40) will be described in greater detail below.

As noted above, handle assembly (20) includes a pistol grip (22) and a closure trigger (24). As also noted above, anvil (60) is closed toward lower jaw (50) in response to distal advancement of closure ring (36). In the present example, closure trigger (24) is pivotable toward pistol grip (22) to drive closure tube (32) and closure ring (36) distally. Various suitable components that may be used to convert pivotal movement of closure trigger (24) toward pistol grip (22) into distal translation of closure tube (32) and closure ring (36) relative to handle assembly (20) will be apparent to those of ordinary skill in the art in view of the teachings herein. When closure trigger (24) reaches a fully pivoted state, such that anvil (60) is in a fully closed position relative to lower jaw (50), locking features in handle assembly (20) lock the position of trigger (24) and closure tube (32), thereby locking anvil (60) in a fully closed position relative to lower jaw (50). These locking features are released by actuation of anvil release button (25). Anvil release button (25) is configured and positioned to be actuated by the thumb of the operator hand that grasps pistol grip (22). In other words, the operator may grasp pistol grip (22) with one hand, actuate closure trigger (24) with one or more fingers of the same hand, and then actuate anvil release button (25) with the thumb of the same hand, without ever needing to release the grasp of pistol grip (22) with the same hand. Other suitable features that may be used to actuate anvil (60) will be apparent to those of ordinary skill in the art in view of the teachings herein.

D. Exemplary Actuation of Firing Beam

In the present example, instrument (10) provides motorized control of firing beam (82). In particular, instrument (10) includes motorized components that are configured to drive firing beam (82) distally in response to pivoting of firing trigger (26) toward pistol grip (22). In some versions, a motor (not shown) is contained in pistol grip (22) and receives power from battery pack (28). This motor is coupled with a transmission assembly (not shown) that converts rotary motion of a drive shaft of the motor into linear translation of firing beam (82). In some such versions, firing beam (82) may only be advanced distally when anvil (60) is in a fully closed position relative to lower jaw (50). After firing beam (82) is advanced distally to sever tissue and drive staples (77) as described above with reference to FIGS. 7A-7B, the drive assembly for firing beam (82) may be automatically reversed to drive firing beam (82) proximally back to the retracted position (e.g., back from the position shown in FIG. 7B to the position shown in FIG. 7A). Alternatively, the operator may actuate firing beam reverse switch (27), which may reverse the drive assembly for firing beam (82) in order to retract firing beam (82) to a proximal position. Handle assembly (20) of the present example further includes a bailout feature (21), which is operable to provide a mechanical bailout allowing the operator to manually retract firing beam (82) proximally (e.g., in the event of power loss while firing beam (82) is in a distal position, etc.).

By way of example only, the features that are operable to provide motorized actuation of firing beam (82) may be configured and operable in accordance with at least some of the teachings of U.S. Pat. No. 8,210,411, entitled "Motor-Driven Surgical Instrument," issued Jul. 3, 2012, the disclosure of which is incorporated by reference herein. As another merely illustrative example, the features that are operable to provide motorized actuation of firing beam (82) may be configured and operable in accordance with at least some of the teachings of U.S. Pat. No. 8,453,914, entitled "Motor-Driven Surgical Cutting Instrument with Electric Actuator Directional Control Assembly," issued Jun. 4, 2013, the disclosure of which is incorporated by reference herein. As yet another merely illustrative example, the features that are operable to provide motorized actuation of firing beam (82) may be configured and operable in accordance with at least some of the teachings of U.S. patent application Ser. No. 14/226,142, entitled "Surgical Instrument Comprising a Sensor System," filed Mar. 26, 2014, issued as U.S. Pat. No. 9,913,642 on Mar. 13, 2018, the disclosure of which is incorporated by reference herein.

Other suitable components, features, and configurations that may be used to provide motorization of firing beam (82) will be apparent to those of ordinary skill in the art in view of the teachings herein. It should also be understood that some other versions may provide manual driving of firing beam (82), such that a motor may be omitted. By way of example only, firing beam (82) may be manually actuated in accordance with at least some of the teachings of any other reference cited herein.

Figure 8:
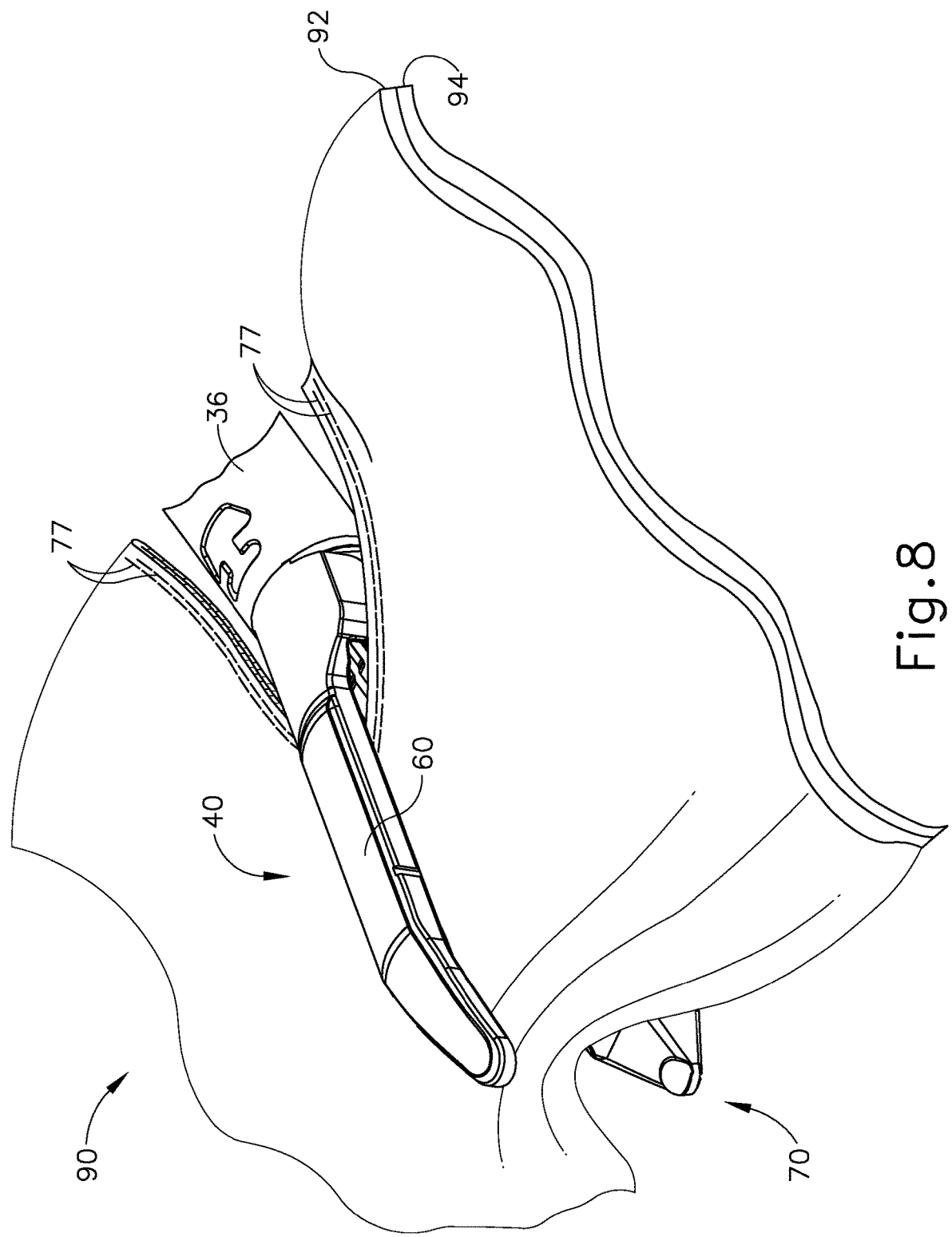
FIG. 8 depicts a perspective view of the end effector of FIG. 3, positioned at tissue and having been actuated once in the tissue.

FIG. 8 shows end effector (40) having been actuated through a single stroke through tissue (90). As shown, cutting edge (84) (obscured in FIG. 8) has cut through tissue (90), while staple drivers (75) have driven two alternating rows of staples (77) through the tissue (90) on each side of the cut line produced by cutting edge (84). Staples (77) are all oriented substantially parallel to the cut line in this example, though it should be understood that staples (77) may be positioned at any suitable orientations. In the present example, end effector (40) is withdrawn from the trocar after the first stroke is complete, the spent staple cartridge (70) is replaced with a new staple cartridge (70), and end effector (40) is then again inserted through the trocar to reach the stapling site for further cutting and stapling. This process may be repeated until the desired amount of cuts and staples (77) have been provided. Anvil (60) may need to be closed to facilitate insertion and withdrawal through the trocar; and anvil (60) may need to be opened to facilitate replacement of staple cartridge (70).

It should be understood that cutting edge (84) may cut tissue substantially contemporaneously with staples (77) being driven through tissue during each actuation stroke. In the present example, cutting edge (84) just slightly lags behind driving of staples (77), such that a staple (47) is driven through the tissue just before cutting edge (84) passes through the same region of tissue, though it should be understood that this order may be reversed or that cutting edge (84) may be directly synchronized with adjacent staples. While FIG. 8 shows end effector (40) being actuated in two layers (92, 94) of tissue (90), it should be understood that end effector (40) may be actuated through a single layer of tissue (90) or more than two layers (92, 94) of tissue. It should also be understood that the formation and positioning of staples (77) adjacent to the cut line produced by cutting edge (84) may substantially seal the tissue at the cut line, thereby reducing or preventing bleeding and/or leaking of other bodily fluids at the cut line. Furthermore, while FIG. 8 shows end effector (40) being actuated in two substantially flat, apposed planar layers (92, 94) of tissue, it should be understood that end effector (40) may also be actuated across a tubular structure such as a blood vessel, a section of the gastrointestinal tract, etc. FIG. 8 should therefore not be viewed as demonstrating any limitation on the contemplated uses for end effector (40). Various suitable settings and procedures in which instrument (10) may be used will be apparent to those of ordinary skill in the art in view of the teachings herein.

It should also be understood that any other components or features of instrument (10) may be configured and operable in accordance with any of the various references cited herein. Additional exemplary modifications that may be provided for instrument (10) will be described in greater detail below. Various suitable ways in which the below teachings may be incorporated into instrument (10) will be apparent to those of ordinary skill in the art. Similarly, various suitable ways in which the below teachings may be combined with various teachings of the references cited herein will be apparent to those of ordinary skill in the art. It should therefore be understood that the teachings below may be readily incorporated into the various instruments taught in the various references that are cited herein. It should also be understood that the below teachings are not limited to instrument (10) or devices taught in the references cited herein. The below teachings may be readily applied to various other kinds of instruments, including instruments that would not be classified as surgical staplers. Various other suitable devices and settings in which the below teachings may be applied will be apparent to those of ordinary skill in the art in view of the teachings herein.

II. Exemplary Buttress for Surgical Stapler

As noted above, it may be desirable in some instances to equip end effector (40) with a buttress material to reinforce the mechanical fastening of tissue (90) provided by staples (77). Such a buttress may prevent the applied staples (77) from pulling through tissue (90) and may otherwise reduce a risk of tissue (90) tearing at or near the site of applied staples (77). In addition to or as an alternative to providing structural support and integrity to a line of staples (77), a buttress may provide various other kinds of effects such as spacing or gap-filling, administration of therapeutic agents, and/or other effects. In some instances, a buttress may be provided on deck (73) of staple cartridge (70). In some other instances, a buttress may be provided on the surface of anvil

(60) that faces staple cartridge (70). It should also be understood that a first buttress may be provided on deck (73) of staple cartridge (70) while a second buttress is provided on anvil (60) of the same end effector (40). Various examples of forms that a buttress may take will be described in greater detail below. Various ways in which a buttress may be secured to a staple cartridge (70) or an anvil (60) will also be described in greater detail below.

A. Exemplary Composition of Buttress for Surgical Stapler

Figure 9:
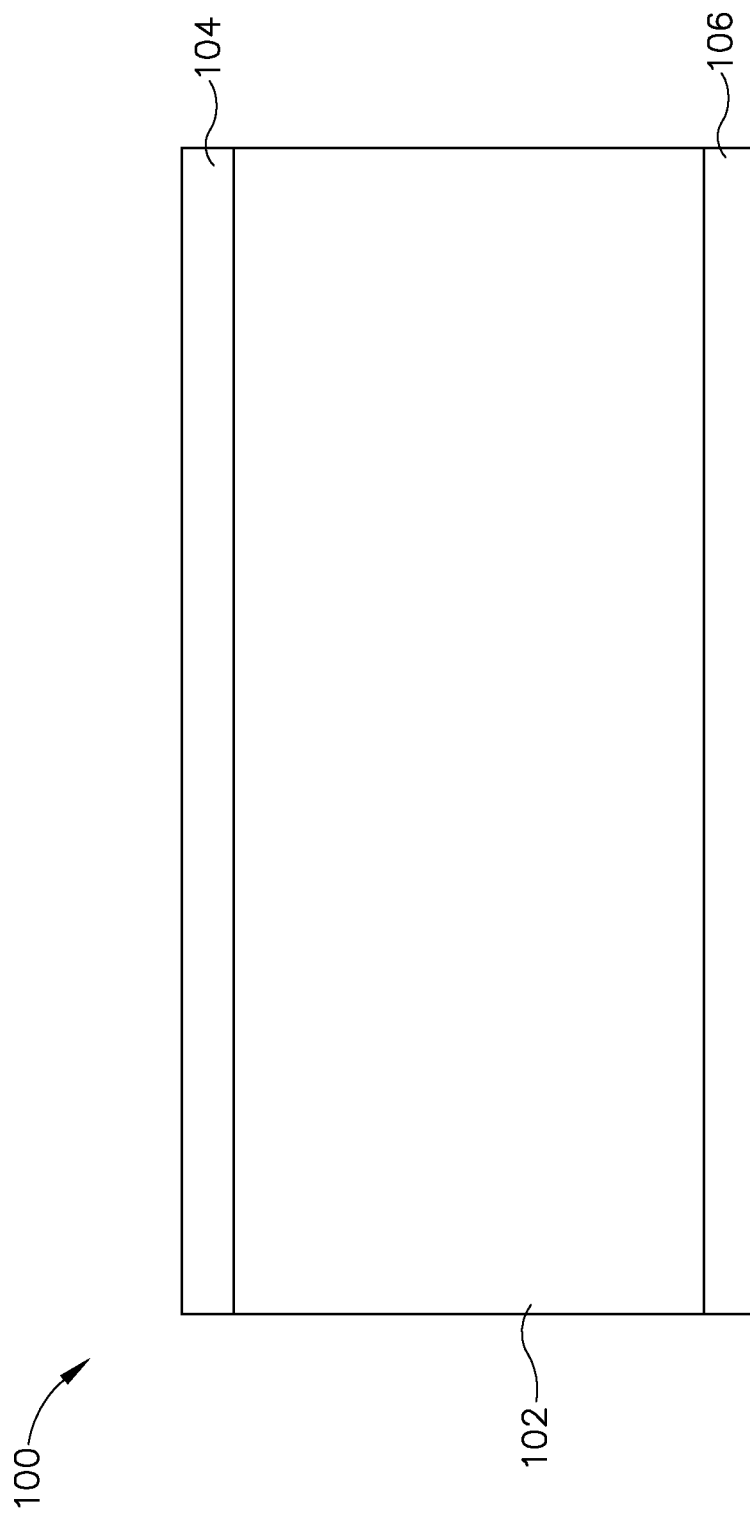
FIG. 9 depicts a cross-sectional view of an exemplary buttress assembly that may be used with the end effector of FIG. 3.
Figure 10:
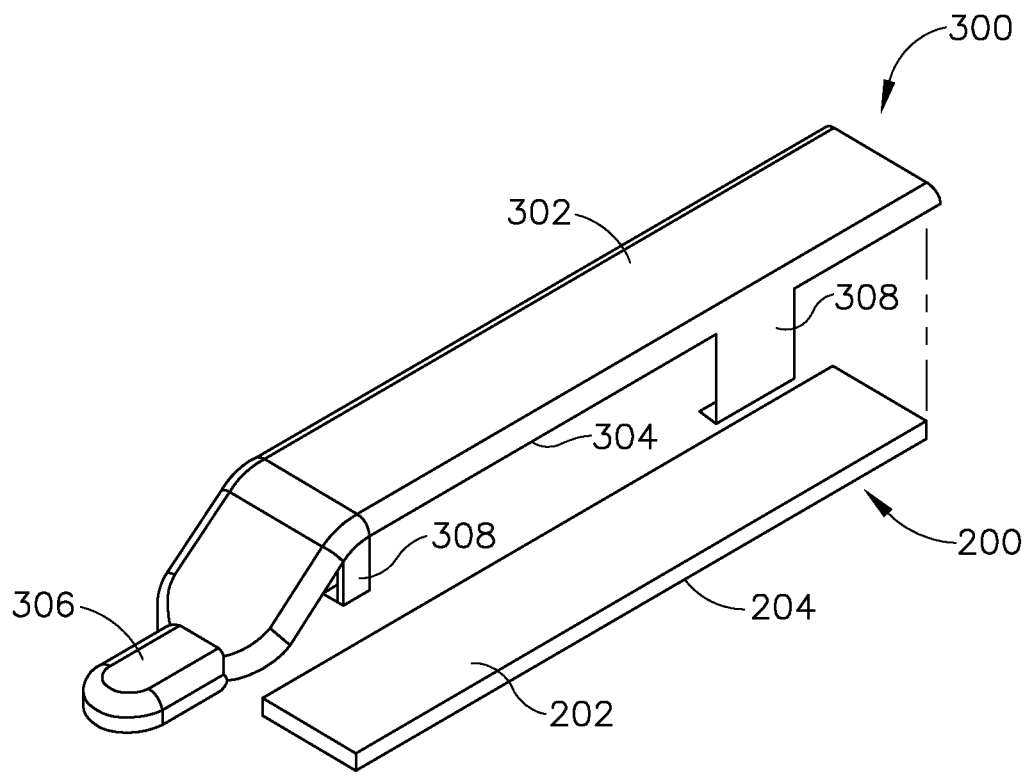
FIG. 10 depicts an exploded perspective view of an exemplary buttress and retainer.
Figure 11:
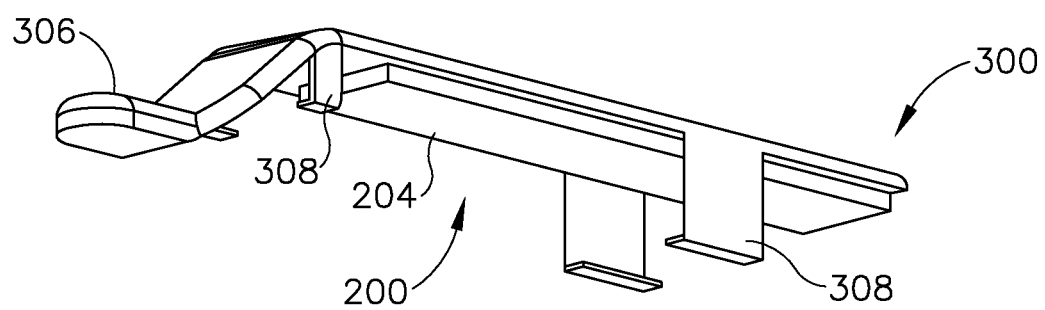
FIG. 11 depicts a perspective view of the buttress and retainer of FIG. 10, with the buttress secured to the underside of the retainer.

FIG. 9 shows an exemplary buttress assembly (100) with a basic composition. Buttress assembly (100) of this example comprises a buttress body (102), an upper adhesive layer (104), and a lower adhesive layer (106). In the present example, buttress body (102) comprises a strong yet flexible material configured to structurally support a line of staples (77). In addition or in the alternative, buttress body (102) may comprise a material including, for example, a hemostatic agent such as fibrin to assist in coagulating blood and reduce bleeding at the severed and/or stapled surgical site along tissue (90).

As another merely illustrative example, buttress body (102) may comprise other adjuncts or hemostatic agents such as thrombin may be used such that buttress body (102) may assist to coagulate blood and reduce the amount of bleeding at the surgical site. The hemostatic abilities of such adjuncts may also contribute to the use of such adjuncts as adhesives and sealants. The agents may assist to coagulate blood at a surgical site, which allows tissue surrounding such blood to stick together and may prevent leaks along the stapled tissue site, for example. Other adjuncts or reagents that may be incorporated into buttress body (102) may further include but are not limited to medical fluid or matrix components. By way of example only, buttress body (102) may include natural or genetically engineered absorbable polymers or synthetic absorbable polymers, or mixtures thereof. Merely illustrative examples of natural or genetically engineered absorbable polymers are proteins, polysaccharides and combinations thereof. Merely illustrative examples of proteins that may be used include prothrombin, thrombin, fibrinogen, fibrin, fibronectin, heparinase, Factor X/Xa, Factor VII/VIIa, Factor IX/IXa, Factor XI/XIa, Factor XII/XIIa, tissue factor, batroxobin, ancrod, ecarin, von Willebrand Factor, collagen, elastin, albumin, gelatin, platelet surface glycoproteins, vasopressin, vasopressin analogs, epinephrine, selectin, procoagulant venom, plasminogen activator inhibitor, platelet activating agents, synthetic peptides having hemostatic activity, and/or combinations thereof. Polysaccharides include, without limitation, cellulose, alkyl cellulose, e.g. methylcellulose, alkylhydroxyalkyl cellulose, hydroxyalkyl cellulose, cellulose sulfate, salts of carboxymethyl cellulose, carboxymethyl cellulose, carboxyethyl cellulose, chitin, carboxymethyl chitin, hyaluronic acid, salts of hyaluronic acid, alginate, alginic acid, propylene glycol alginate, glycogen, dextran, dextran sulfate, curdlan, pectin, pullulan, xanthan, chondroitin, chondroitin sulfates, carboxymethyl dextran, carboxymethyl chitosan, chitosan, heparin, heparin sulfate, heparan, heparan sulfate, dermatan sulfate, keratan sulfate, carrageenans, chitosan, starch, amylose, amylopectin, poly-N-glucosamine, polymannuronic acid, polyglucuronic acid polyguluronic acid, and derivatives of any of the above. Examples of synthetic absorbable polymers are aliphatic polyester polymers, copolymers, and/or combinations thereof. The aliphatic polyesters are typically synthesized in a ring opening polymerization of monomers including, but not limited to, lactic acid, lactide (including L-, D-, meso and D, L mixtures), glycolic acid, glycolide, ε-caprolactone, p-dioxanone (1,4-dioxan-2-one), and trimethylene carbonate (1,3-dioxan-2-one). Other suitable compounds, materials, substances, etc., that may be used in a medical fluid or matrix will be apparent to those of ordinary skill in the art in view of the teachings herein.

Buttress body (102) may alternatively comprise a fibrous pad, a foam, a mesh, a weave, and/or another structure capable of containing an adhesive and/or other type of medical fluid. In addition or in the alternative, buttress body (102) may simply comprise a mesh, a weave, and/or some other structure that is constructed to provide structural support or integrity to a line of staples (77) applied through tissue (90). Such a material and structure may be relatively thin and in some instances may be substantially non-compressible. By way of further example only, buttress body (102) may be constructed in accordance with at least some of the teachings of U.S. Patent Pub. No. 2012/0241493, entitled "Tissue Thickness Compensator Comprising Controlled Release and Expansion," published Sep. 27, 2012, issued as U.S. Pat. No. 10,123,798 on Nov. 13, 2018, the disclosure of which is incorporated by reference herein; U.S. Patent Pub. No. 2013/0068816, entitled "Surgical Instrument and Buttress Material," published Mar. 21, 2013, now abandoned, the disclosure of which is incorporated by reference herein; U.S. Patent Pub. No. 2013/0062391, entitled "Surgical Instrument with Fluid Fillable Buttress," published Mar. 14, 2013, issued as U.S. Pat. No. 9,999,408 on Jun. 19, 2018, the disclosure of which is incorporated by reference herein; U.S. Patent Pub. No. 2013/0068820, entitled "Fibrin Pad Matrix with Suspended Heat Activated Beads of Adhesive," published Mar. 21, 2013, issued as U.S. Pat. No. 8,814,025 on Aug. 26, 2014, the disclosure of which is incorporated by reference herein; U.S. Patent Pub. No. 2013/0082086, entitled "Attachment of Surgical Staple Buttress to Cartridge," published Apr. 4, 2013, issued as U.S. Pat. No. 8,899,464 on Dec. 2, 2014, the disclosure of which is incorporated by reference herein; U.S. Patent Pub. No. 2013/0037596, entitled "Device for Applying Adjunct in Endoscopic Procedure," published Feb. 14, 2013, issued as U.S. Pat. No. 9,492,170 on Nov. 15, 2016, the disclosure of which is incorporated by reference herein; U.S. Patent Pub. No. 2013/0062393, entitled "Resistive Heated Surgical Staple Cartridge with Phase Change Sealant," published Mar. 14, 2013, issued as U.S. Pat. No. 8,998,060 on Apr. 7, 2015, the disclosure of which is incorporated by reference herein; U.S. Patent Pub. No. 2013/0075446, entitled "Surgical Staple Assembly with Hemostatic Feature," published Mar. 28, 2013, issued as U.S. Pat. No. 9,393,018 on Jul. 19, 2016, the disclosure of which is incorporated by reference herein; U.S. Patent Pub. No. 2013/0062394, entitled "Surgical Staple Cartridge with Self-Dispensing Staple Buttress," published Mar. 14, 2013, issued as U.S. Pat. No. 9,101,359 on Aug. 11, 2015, the disclosure of which is incorporated by reference herein; U.S. Patent Pub. No. 2013/0075445, entitled "Anvil Cartridge for Surgical Fastening Device," published Mar. 28, 2013, issued as U.S. Pat. No. 9,198,644 on Dec. 1, 2015, the disclosure of which is incorporated by reference herein; U.S. Patent Pub. No. 2013/0075447, entitled "Adjunct Therapy for Applying Hemostatic Agent," published Mar. 28, 2013, now abandoned, the disclosure of which is incorporated by reference herein; and/or U.S. Patent Pub. No. 2013/0256367, entitled "Tissue Thickness Compensator Comprising a Plurality of Medicaments," published Oct. 3, 2013, issued as U.S. Pat. No. 9,211,120 on Dec. 15, 2015, the disclosure of which is incorporated by reference herein.

In the present example, buttress body (102) comprises a woven mesh of VICRYL® (polyglactin 910) material by Ethicon US, LLC. VICRYL® woven mesh is prepared from a synthetic absorbable copolymer of glycolide and lactide, derived respectively from glycolic and lactic acids. This tightly woven mesh is prepared from uncoated, undyed fiber identical in composition to that used in VICRYL® synthetic absorbable suture, which has been found to be inert, nonantigenic, nonpyrogenic, and to elicit only a mild tissue reaction during absorption. VICRYL® woven mesh is intended for use as a buttress to provide temporary support during the healing process. Alternatively, any other suitable materials or combinations of materials may be used in addition to or as an alternative to VICRYL® material to form buttress body (102).

In versions where buttress body (102) is formed as a mesh, it should be understood that various kinds of mesh geometry may be used. By way of example only, buttress body (102) may be formed as a woven mesh, a knitted mesh, or a warp knitted mesh. Regardless of whether buttress body (102) is formed as a mesh or not, buttress body (102) is porous in some examples. As described in greater detail below, an adhesive layer (104, 106) may be provided on buttress body (102) in order to adhere buttress body (102) to underside (65) of anvil (60) or deck (73) of staple cartridge (70). In some versions where buttress body (102) is porous, the material forming adhesive layer (104, 106) may pass through buttress body (102) to reach the outer surface of buttress body (102) that is opposite to the surface on which adhesive layer (104, 106) is disposed.

By way of example only, upper adhesive layer (104) may be used to secure buttress assembly (100) to the underside (304) of a retainer (300) as will be described in greater detail below; while lower adhesive layer (106) is used to secure buttress assembly (100) to deck (73) of staple cartridge (70). In some versions of this example, lower adhesive layer (106) is configured to provide stronger adherence than upper adhesive layer (104). In some illustrative variations of this example, one or more features of retainer (300) (e.g., flanges, clips, etc.) are configured to selectively retain buttress assembly (100) against underside (304) of retainer (300), such that upper adhesive layer (104) is omitted; while lower adhesive layer (106) is used to secure buttress assembly (100) to deck (73) of staple cartridge (70). In addition or in the alternative, an adhesive material may be applied to the lower surface of a porous version of buttress body (102) to form lower adhesive layer (106), and some of that adhesive material may pass through buttress body (102) to form upper adhesive layer (104). In some such versions, lower adhesive layer (106) ultimately has more adhesive material than upper adhesive layer (104), such that lower adhesive layer (106) provides greater adhesion than upper adhesive layer (104).

In yet another merely illustrative example, lower adhesive layer (106) may be used to secure buttress assembly (100) to the upper side (302) of a retainer (300) as will be described in greater detail below; while upper adhesive layer (104) is used to secure buttress assembly to underside (65) of anvil (60) of end effector (40). In some versions of this example, upper adhesive layer (104) is configured to provide stronger adherence than lower adhesive layer (106). In some illustrative variations of this example, one or more features of retainer (300) (e.g., flanges, clips, etc.) are configured to selectively retain buttress assembly (100) against upper side (302) of retainer (300), such that lower adhesive layer (106) is omitted; while upper adhesive layer (104) is used to secure buttress assembly (100) to underside (65) of anvil (60). In addition or in the alternative, an adhesive material may be applied to the upper surface of a porous version of buttress body (102) to form upper adhesive layer (104), and some of that adhesive material may pass through buttress body (102) to form lower adhesive layer (106). In some such versions, upper adhesive layer (104) ultimately has more adhesive material than lower adhesive layer (106), such that upper adhesive layer (104) provides greater adhesion than lower adhesive layer (106).

Various suitable compositions that may be used to form each adhesive layer (104, 106), as well as various forms that each adhesive layer (104, 106) may take, will be described in greater detail below.

It should also be understood that buttress assembly (100) may include an impermeable layer or a semi impermeable layer interposed between buttress body (102) and adhesive layer (102), to prevent or restrict migration of adhesive material from adhesive layer (104, 106) into buttress body (100). By way of example only, body (102) may be formed of a porous media (e.g., ETHISORB™ by Codman of Raynham, Mass.); while the semi impermeable layer may comprise polydioxanone (PDS). In versions where buttress assembly (100) comprises an impermeable layer or a semi impermeable layer to prevent or restrict migration of adhesive material from adhesive layer (104, 106) into buttress body (100), such a layer may be integrated into buttress body (102) such that the layer permits the adhesive to migrate at least partially into buttress body (102) but not across the full thickness of buttress body (102). Various suitable ways in which an impermeable layer or a semi impermeable layer may be integrated into buttress assembly (100) to prevent or restrict migration of an adhesive material will be apparent to those of ordinary skill in the art in view of the teachings herein.

B. Exemplary Instrument and Technique for Securing Buttress to Deck of Staple Cartridge FIGS. 10-12D show a combination of an exemplary buttress (200) with an exemplary retainer (300). Buttress (200) of this example may be constructed in accordance with the teachings above relating to buttress assembly (100) and/or in accordance with other teachings herein. Buttress (200) includes an upper side (202) and an underside (204). In the present example, underside (204) includes an adhesive (e.g., like lower adhesive layer (106)) to secure buttress (200) to deck (73) of staple cartridge (70) as described in greater detail below.

Retainer (300) of this example comprises an upper side (302), an underside (304), a distally projecting tongue (306), and a set of resilient latches (308). Upper side (302) and underside (304) are each generally flat in the present example, though it should be understood that upper side (302) and/or underside (304) may include various kinds of features as described elsewhere herein. Tongue (306) is configured to provide a grip for an operator, thereby facilitating grasping and handling of retainer (300) during use. Latches (308) are configured to releasably secure retainer (300) to lower jaw (50) of end effector (40) as will be described in greater detail below. By way of example only, retainer (300) may be formed of molded plastic. Alternatively, retainer (300) may be formed using any other suitable material(s) or technique(s).

In the present example, buttress (200) is secured to underside (304) of retainer (300), such that upper side (202) of buttress (200) apposes underside (304) of retainer (300). In some versions, an adhesive such as upper adhesive layer (104) provides releasable adhesion of buttress (200) to underside (304) of retainer (300). In some other versions, retainer (300) includes one or more features (e.g., flanges, clips, etc.) that are configured to selectively retain buttress (200) against underside (304) of retainer (300). Various suitable ways in which buttress (200) may be releasably secured to underside (304) of retainer (300) will be apparent to those of ordinary skill in the art in view of the teachings herein.

Figure 12A:
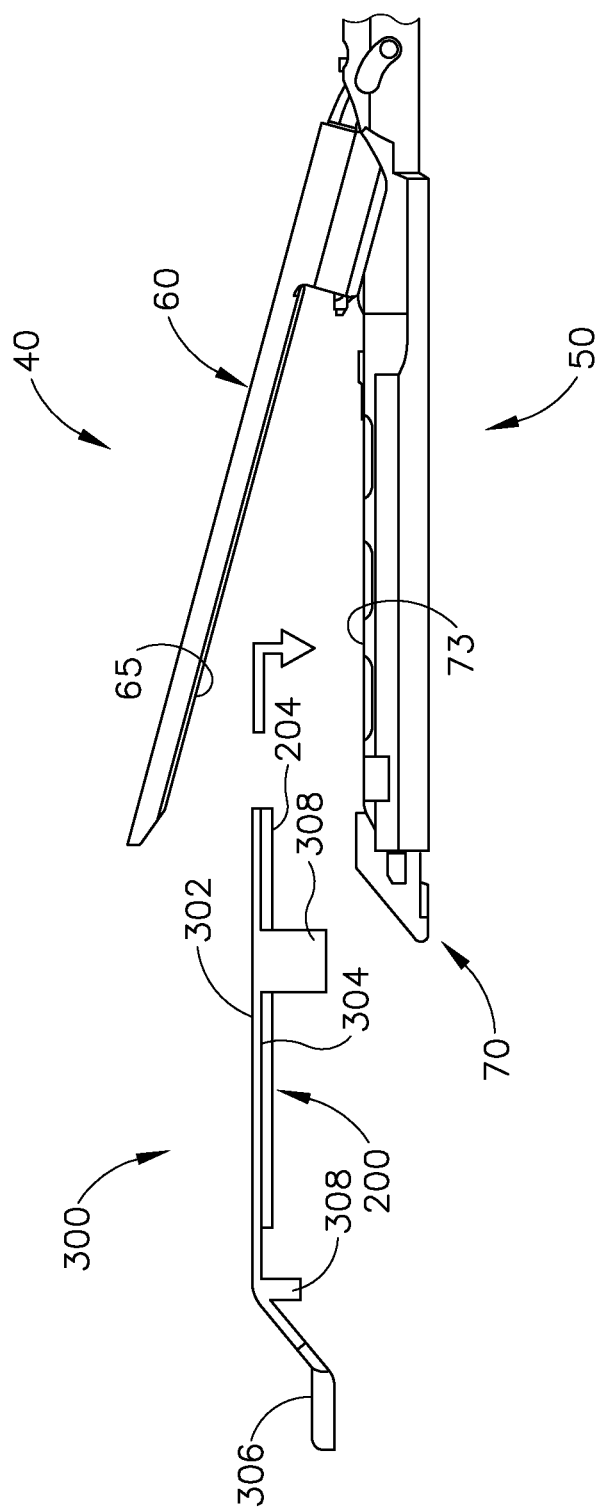
FIG. 12A depicts a side elevational view of the buttress and retainer of FIG. 10 positioned for engagement with the end effector of FIG. 3.
Figure 12D:
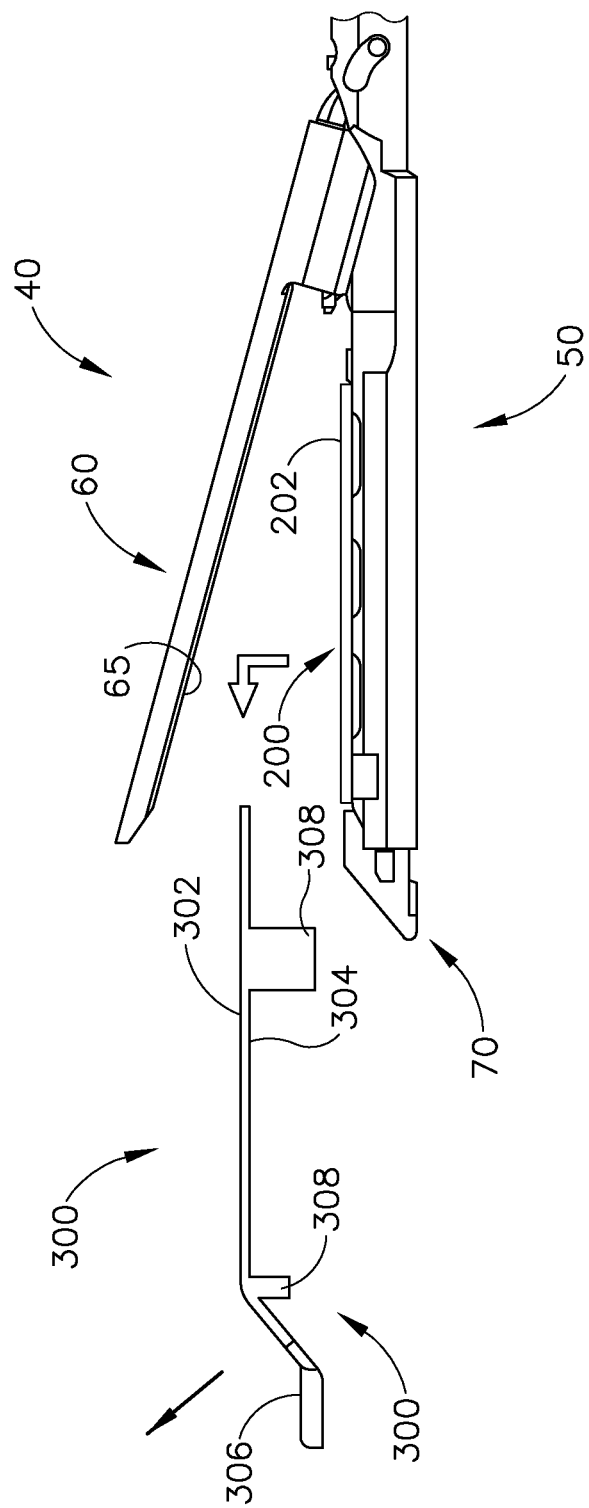
FIG. 12D depicts a side elevational view of the retainer of FIG. 10 being moved away from the end effector of FIG. 3, with the buttress of FIG. 10 being left behind on the end effector to form an end effector and buttress assembly.

As shown in FIG. 12A, the assembly formed by buttress (200) and retainer (300) may be placed before end effector (40) with anvil (60) in the open position. In some instances, a peel-away film (not shown) is positioned over underside (204) of buttress (200) to protect buttress (200) and/or any adhesive material on underside (204) of buttress (200). In such versions, the film is peeled away to expose underside (204) of buttress (200) before reaching the stage shown in FIG. 12A. Such a film may comprise polytetrafluoroethylene (PTFE) and/or any other suitable material(s). After reaching the stage shown in FIG. 12A, the assembly formed by buttress (200) and retainer (300) may then be placed on staple cartridge (70) such that underside (204) of buttress (200) apposingly contacts deck (73) of staple cartridge (70); and such that latches (308) are releasably secured to lower jaw (50) as shown in FIG. 12B. The operator may then drive anvil (60) toward the closed position as shown in FIG. 12C, eventually compressing buttress (200) against deck (73) of staple cartridge (70). Such compression may promote adhesion between underside (204) of buttress (200) and deck (73) of staple cartridge (70). After anvil (60) has been used to compress buttress (200) against deck (73) of staple cartridge (70), anvil (60) may be moved back to the open position as shown in FIG. 12D. As also shown in FIG. 12D, retainer (300) may then be pulled away from end effector (40), leaving behind buttress (200) adhered to deck (73) of staple cartridge (70). Upper side (202) of buttress (200) is exposed. End effector (40) is thus loaded with buttress (200) and ready for use in severing and stapling tissue (90).

Figure 14:
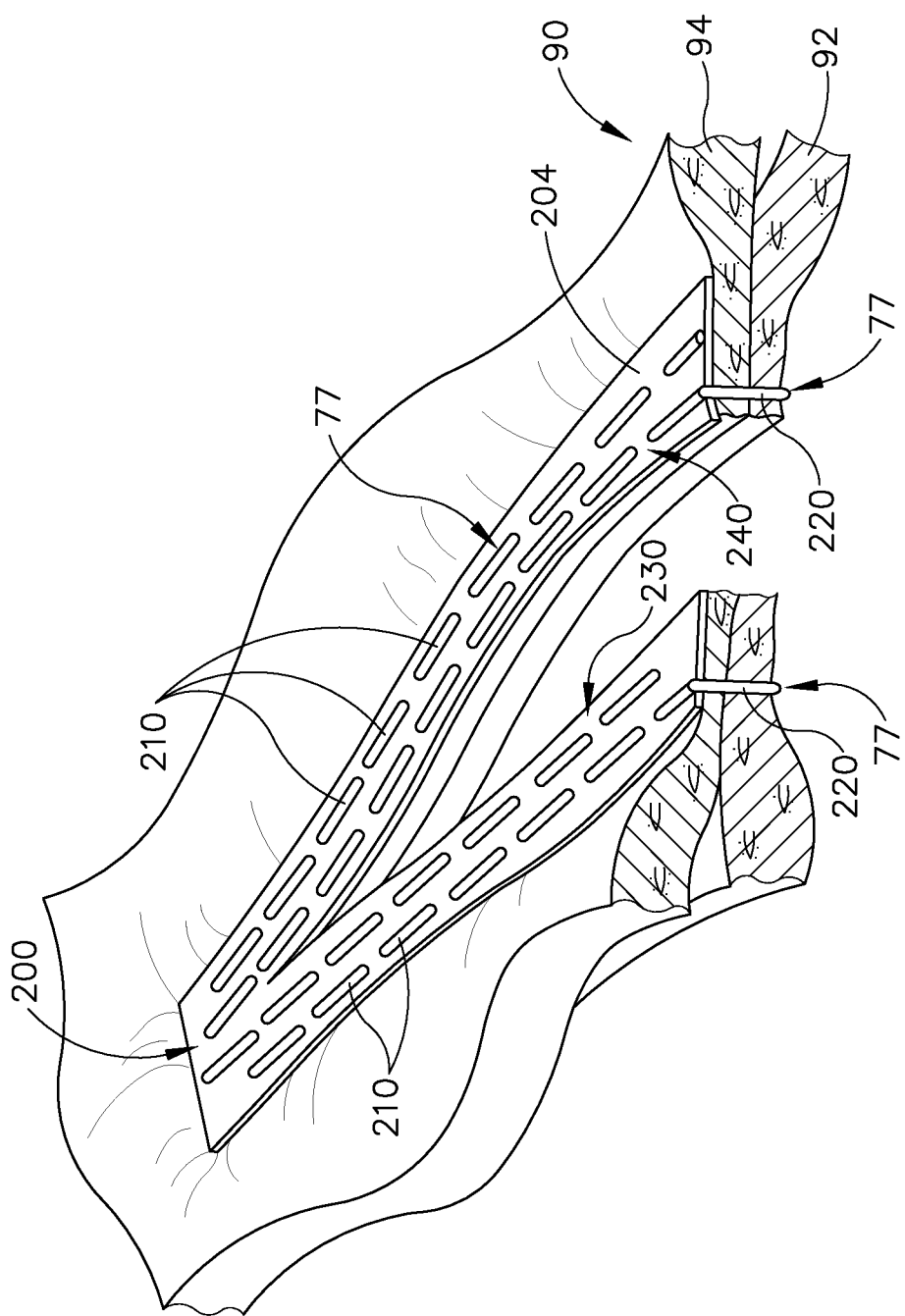
FIG. 14 depicts a perspective view of staples and the buttress of FIG. 12D having been secured to tissue by the end effector of FIG. 12D.
Figure 15:
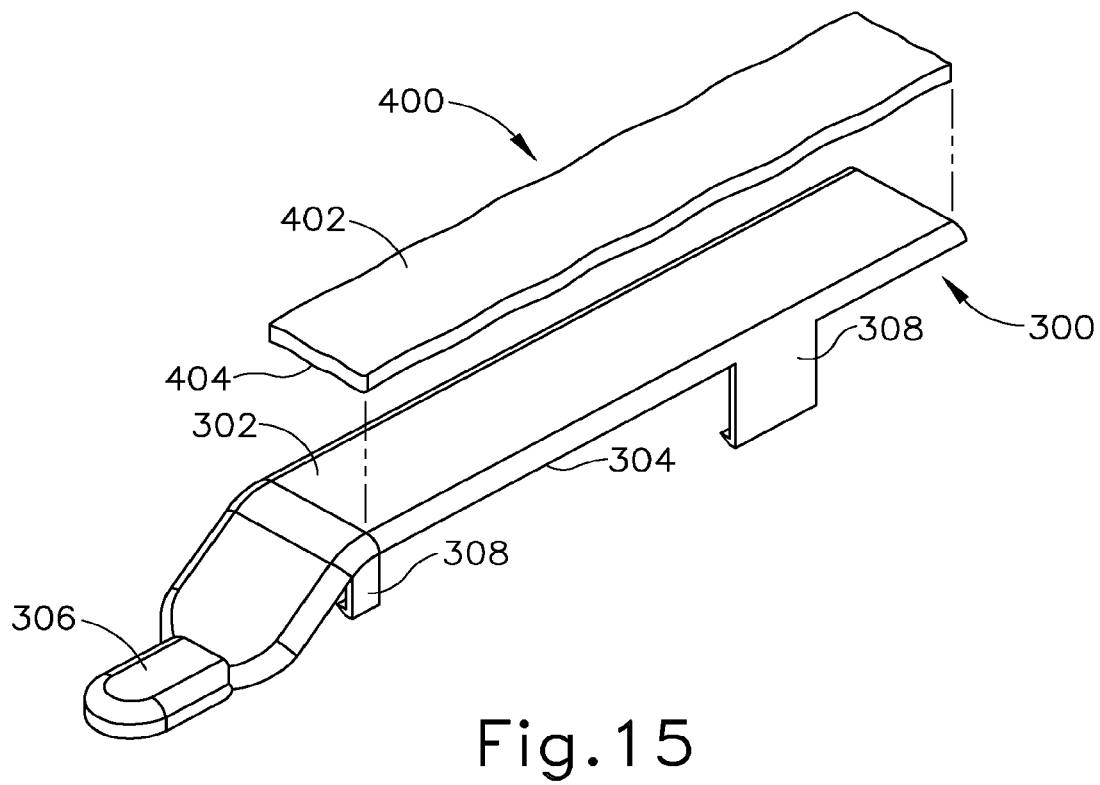
FIG. 15 an exploded perspective view of an exemplary buttress and retainer.
Figure 16:
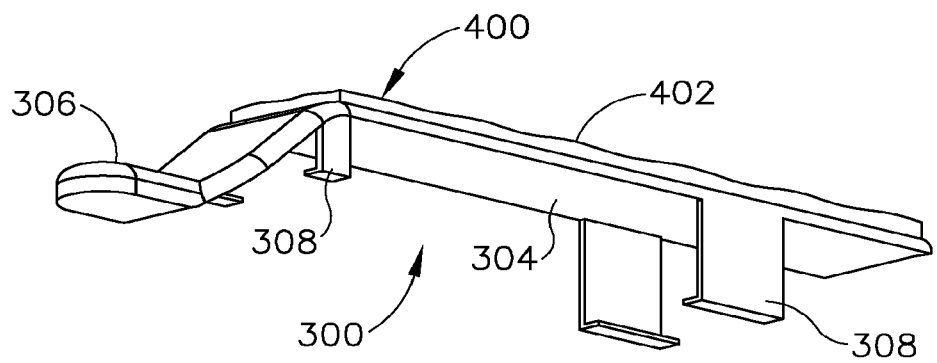
FIG. 16 depicts a perspective view of the buttress and retainer of FIG. 15, with the buttress secured to the top side of the retainer.

FIGS. 13A-13C show an end effector (40) loaded with buttress (200) being used to drive a staple (77) through tissue (90). In FIG. 13A, tissue (90) is placed between anvil (60) and staple cartridge (70), above buttress (200), with anvil (60) in the open position. In FIG. 13B, anvil (60) is driven to the closed position, compressing tissue (90) against buttress (200) and staple cartridge (70). End effector (40) is then actuated as described above, driving staple (77) through buttress (200) and tissue (90). As shown in FIG. 13C, crown (210) of driven staple (77) captures and retains buttress (200) against layer (94) of tissue (90). It should be understood that a series of staples (77) will similarly capture and retain buttress (200) against layer (94) of tissue (90), thereby securing buttress (200) to tissue (90) as shown in FIG. 14. As end effector (40) is pulled away from tissue (90) after deploying staples (77) and buttress (200), buttress (200) disengages deck (73) of staple cartridge (70), such that buttress (200) remains secured to tissue (90) with staples (77). Buttress (200) thus provides structural reinforcement to the lines of staples (77). As can also be seen in FIG. 14, knife member (80) also cuts through a centerline of buttress (200), separating buttress (200) into two sections (230, 240), such that each section (230, 240) remains secured to a respective severed region of tissue (90).

C. Exemplary Instrument and Technique for Securing Buttress to Anvil of End Effector FIGS. 15-17B show a combination of an exemplary buttress (400) with retainer (300). Buttress (400) of this example may be constructed in accordance with the teachings above relating to buttress assembly (100) and/or in accordance with other teachings herein. Buttress (400) includes an upper side (402) and an underside (404). In the present example, upper side (402) includes an adhesive (e.g., like upper adhesive layer (1064) to secure buttress (200) to underside (65) of anvil (60) as described in greater detail below.

In the present example, buttress (400) is secured to upper side (302) of retainer (300), such that underside (404) of buttress (400) apposes upper side (302) of retainer (300). In some versions, an adhesive such as lower adhesive layer (106) provides releasable adhesion of buttress (400) to upper side (302) of retainer (300). In some other versions, retainer (300) includes one or more features (e.g., flanges, clips, etc.) that are configured to selectively retain buttress (400) against upper side (302) of retainer (300). Various suitable ways in which buttress (200) may be releasably secured to upper side (302) of retainer (300) will be apparent to those of ordinary skill in the art in view of the teachings herein.

Figure 17A:
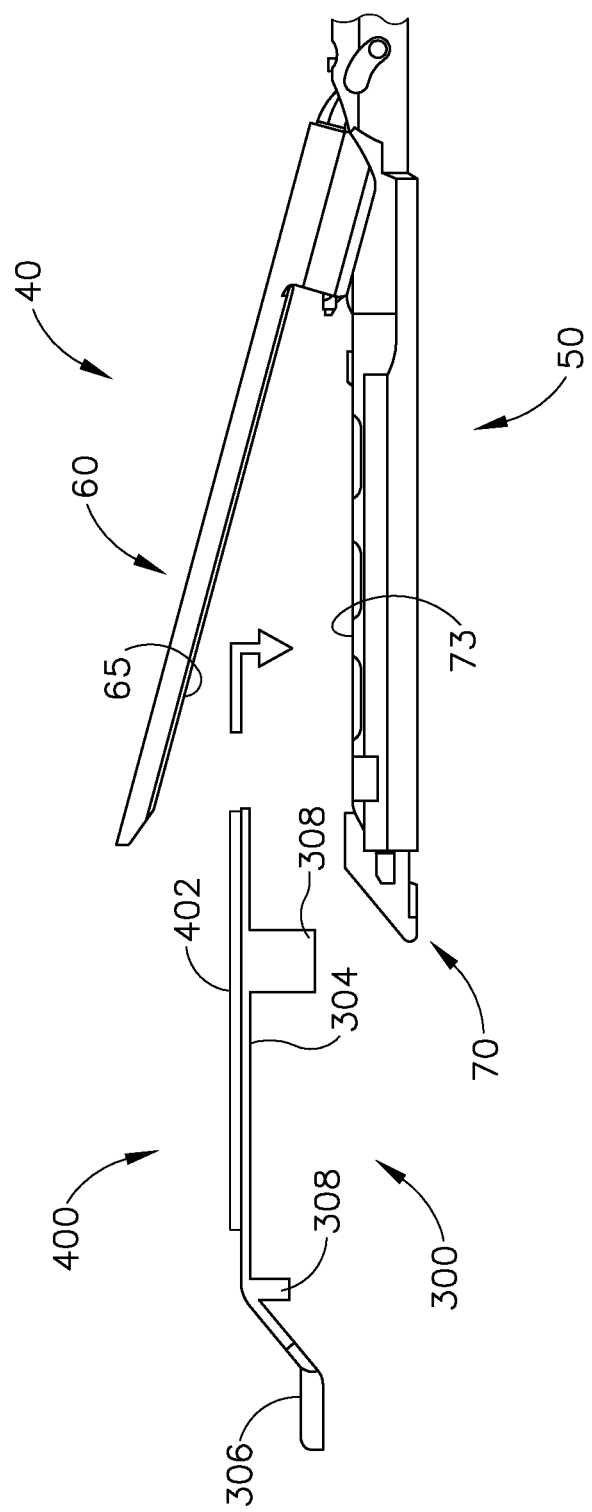
FIG. 17A depicts a side elevational view of the buttress and retainer of FIG. 15 positioned for engagement with the end effector of FIG. 3.
Figure 17B:
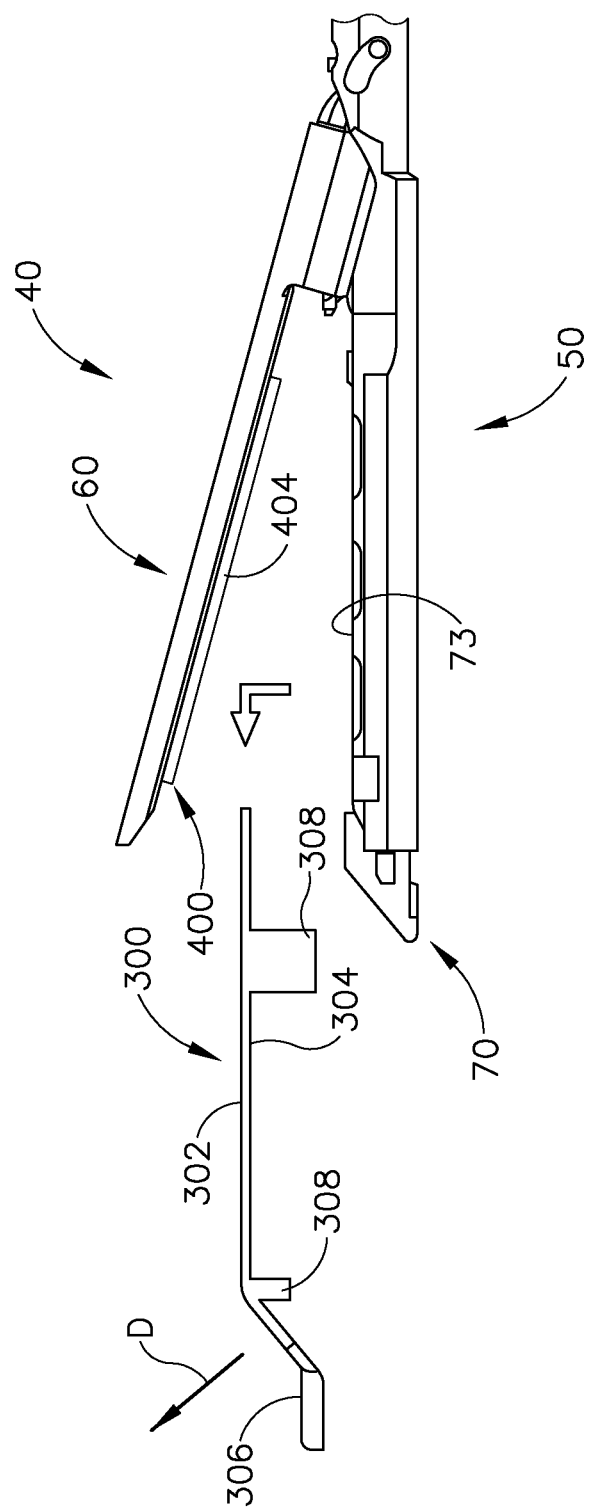
FIG. 17B depicts a side elevational view of the retainer of FIG. 15 being moved away from the end effector of FIG. 3, with the buttress of FIG. 15 being left behind on the end effector to form an end effector and buttress assembly.

As shown in FIG. 17A, the assembly formed by buttress (400) and retainer (300) may be placed before end effector (40) with anvil (60) in the open position. In some instances, a peel-away film (not shown) is positioned over upper side (402) of buttress (400) to protect buttress (400) and/or any adhesive material on upper side (402) of buttress (400). In such versions, the film is peeled away to expose upper side (402) of buttress (400) before reaching the stage shown in FIG. 17A. Such a film may comprise polytetrafluoroethylene (PTFE) and/or any other suitable material(s). After reaching the stage shown in FIG. 17A, the assembly formed by buttress (400) and retainer (300) may then be placed on staple cartridge (70) such that latches (308) are releasably secured to lower jaw (50) as described above. The operator may then drive anvil (60) toward the closed position as described above, eventually compressing buttress (400) underside (65) of anvil (60). Such compression may promote adhesion between upper side (402) of buttress (400) and underside (65) of anvil (60). After anvil (60) has been used to compress buttress (200) against underside (65) of anvil (60), anvil (60) may be moved back to the open position as shown in FIG. 17B. As also shown in FIG. 17B, retainer (300) may then be pulled away from end effector (40), leaving behind buttress (400) adhered to underside (65) of anvil (60). Underside (402) of buttress (400) is exposed. End effector (40) is thus loaded with buttress (400) and ready for use in severing and stapling tissue (90).

Figure 19:
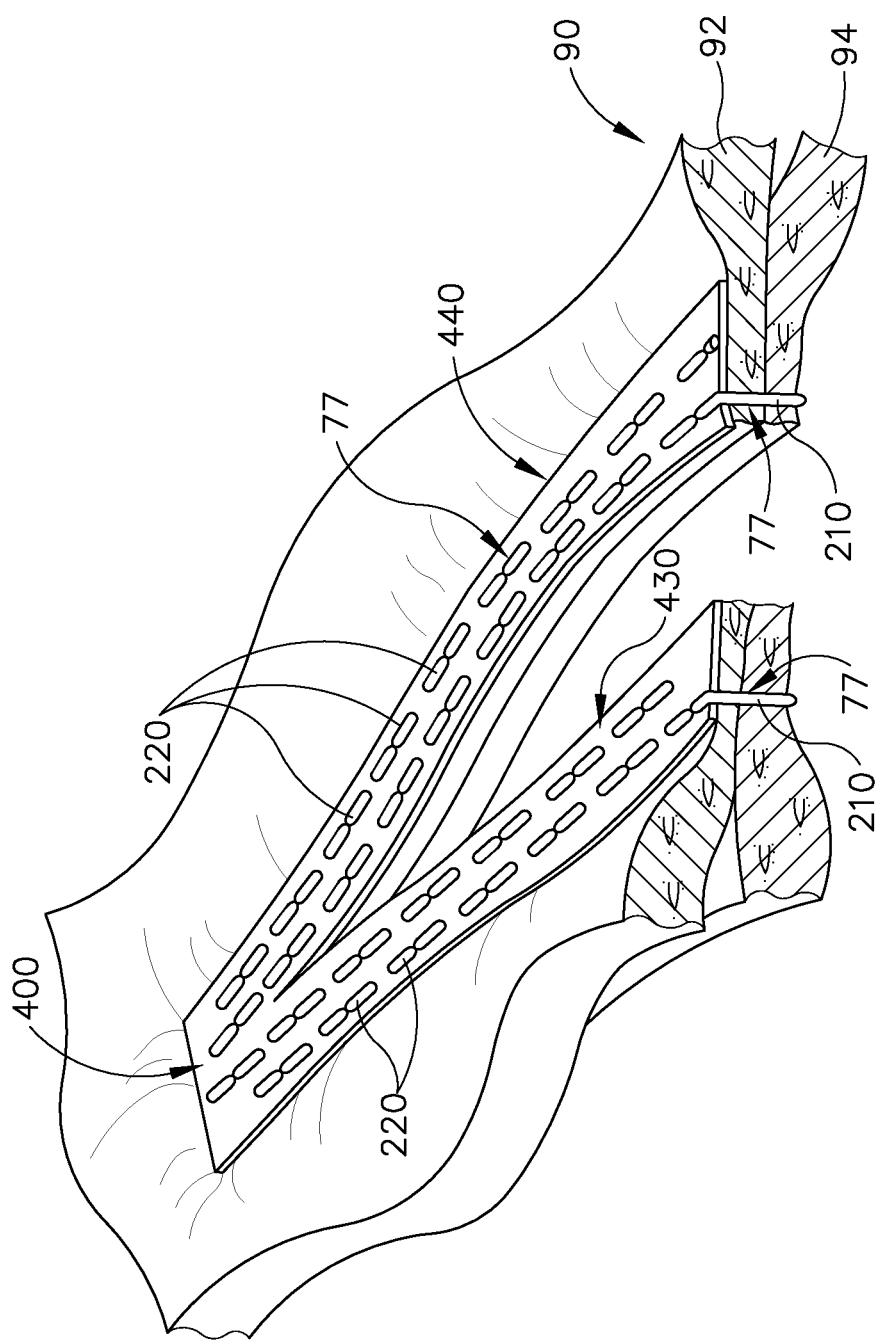
FIG. 19 depicts a perspective view of staples and the buttress of FIG. 17B having been secured to tissue by the end effector of FIG. 17B.

FIGS. 18A-18C show an end effector (40) loaded with buttress (400) being used to drive a staple (77) through tissue (90). In FIG. 18A, tissue (90) is placed between anvil (60) and staple cartridge (70), below buttress (400), with anvil (60) in the open position. In FIG. 18B, anvil (60) is driven to the closed position, compressing tissue (90) against buttress (400) and staple cartridge (70). End effector (40) is then actuated as described above, driving staple (77) through buttress (400) and tissue (90). As shown in FIG. 18C, bent legs (220) of driven staple (77) capture and retains buttress (400) against layer (92) of tissue (90). It should be understood that a series of staples (77) will similarly capture and retain buttress (400) against layer (92) of tissue (90), thereby securing buttress (400) to tissue (90) as shown in FIG. 19. As anvil (60) is returned to the open position to enable end effector (40) to be pulled away from tissue (90) after deploying staples (77) and buttress (400), buttress (400) disengages underside (65) of anvil (60), such that buttress (400) remains secured to tissue (90) with staples (77). Buttress (400) thus provides structural reinforcement to the lines of staples (77). As can also be seen in FIG. 19, knife member (80) also cuts through a centerline of buttress (400), separating buttress (400) into two sections (430, 440), such that each section (430, 440) remains secured to a respective severed region of tissue (90).

While the examples above provide either buttress (200) on underside (304) of retainer (300) or buttress (400) on upper side (302) of retainer (300), it should be understood that both retainers (200, 400) may be provided on the same retainer (300) if desired. In particular, retainer (200) may be provided on underside (304) of retainer (300) while buttress (400) is provided on upper side (302) of retainer (300). This may result in buttress (200) being provided on deck (73) of staple cartridge (70) and buttress (400) being provided on underside (65) of anvil (60) in the same end effector (400). This may ultimately result in buttress (200) being secured against layer (94) of tissue (90) by crowns (210) of staples (77) while buttress (400) is secured against layer (92) of tissue (90) by bent legs (220) of the same staples (77).

III. Exemplary Materials and Techniques for Providing Adhesion of Buttress to Surgical Stapler As noted above, a buttress assembly (100) may include at least one layer (104, 106) of adhesive material (or other form of adhesive material) that adheres buttress body (102) to either underside (65) of anvil (60) or deck (73) of staple cartridge (70). Such an adhesive material may provide proper positioning of buttress body (102) before and during actuation of end effector (40); then allow buttress body (102) to separate from end effector (40) after end effector (40) has been actuated, without causing damage to buttress body (102) that is substantial enough to compromise the proper subsequent functioning of buttress body (102). It may be desirable to minimize the impact of such an adhesive material on the functioning of firing beam (82) wedge sled (78), and staple drivers (75). For instance, it may be desirable to prevent the adhesive material from blocking or otherwise providing significant resistance to movement of firing beam (82) wedge sled (78), and staple drivers (75). Moreover, the adhesive material should allow buttress body (102) to detach easily enough from an actuated end effector (40) to avoid tearing tissue (90) after staples (77) have been fired through the tissue and anvil (60) is moved to the open position.

In some instances, it may be desirable for the adhesive material to provide additional effects, beyond merely adhering buttress body (102) to either underside (65) of anvil (60) or deck (73) of staple cartridge (70). For instance, the adhesive material may include one or more components that provide a therapeutic effect, hemostatic effect, or other desired effect on tissue (90). As another merely illustrative example, the adhesive material may fill in at least part of the paths that are formed through tissue (90) and/or buttress body (102) by legs (220) of staple (77) being driven through tissue (90) and buttress body (102).

In some instances, the adhesive material for a buttress body (102) may be pressure sensitive. In addition or in the alternative, the adhesive material may be configured to take the form of surface irregularities of buttress body (102); in addition to or in lieu of taking the form of surface irregularities in underside (65) of anvil (60) and/or deck (73) of staple cartridge (70).

The above noted characteristics of an adhesive material for a buttress body (102) are merely illustrative examples. Suitable adhesive materials may possess various other characteristics in addition to or in lieu of those above. Suitable adhesive materials may also be provided in various different kinds of compositions. Examples of various suitable compositions and configurations that may be used to form and provide an adhesive material for a buttress body (102), as well as various exemplary characteristics that such adhesive material may possess, are described in greater detail below.

A. Exemplary Polymeric Adhesive Materials with Synthetic Base

In some instances, an adhesive material (e.g., one or more of layers (104, 106)) for a buttress body (102) comprises an absorbable synthetic based polymer. Various physiomechanical properties of synthetic based polymers may be modified in order to provide different adhesive properties. Such variable characteristics include but are not limited to copolymer composition, glass transition temperature (Tg), molecular weight, inherent viscosity (IV), crystallinity, sequence distribution, copolymer chain composition, melting temperature (Tm), and surface tension. Several exemplary combinations of these variables will be provided below, though it should be understood that these examples are merely illustrative. It should also be understood that these examples of adhesive materials may be provided in upper adhesive layer (104). In addition or in the alternative, these examples of adhesive materials may be provided in lower adhesive layer (106). In addition or in the alternative, these examples of adhesive materials may be otherwise integrated into buttress body (102). It should therefore be understood that the adhesive material need not necessarily constitute a separate layer that is discretely identifiable as being different from a layer defined by buttress body (102).

In some examples, the adhesive material is formed by a copolymer of lactide and caprolactone (PLA/PCL). This composition may be provided at a ratio in the range of 20/80 to 60/40; or more particularly the range of 35/65 to 50/50. This composition may have a glass transition temperature (Tg) that is below 4° C., or more particularly below −10° C. This composition may have a molecular weight in the range of 10,000 g/mol to 145,000 g/mol; or more particularly below 200,000 g/mol. The composition may have an inherent viscosity (IV) in the range of 1.0 dL/g to 2.0 dL/g.

In some other examples, the adhesive material is formed by a copolymer of lactide and trimethylene carbonate (PLA/TMC). This composition may be provided at a ratio in the range of 20/80 to 50/50. The other characteristics may be within the same parameters set forth above with respect to the exemplary PLA/PCL composition. Alternatively, the PLA/TMC composition may have any other suitable characteristics.

In some other examples, the adhesive material is formed by a copolymer of trimethylene carbonate and caprolactone (TMC/PCL). This composition may be provided at a ratio in the range of 20/80 to 80/20; or more particularly in the range of 50/50 to 60/40. This composition may have an inherent viscosity (IV) in the range of 0.3 dL/g to 3.0 dL/g; or more particularly in the range of 0.5 dL/g to 1.0 dL/g. This composition may have a crystallinity below 20%; or more particularly below 5%; or more particularly at 0% (i.e., a completely amorphous polymer). This composition may have a glass transition temperature (Tg) below 0° C.; or more particularly below −20° C.

In some other examples, the adhesive material is formed by a copolymer of caprolactone and glycolide (PCL/PGA). This composition may be provided at a ratio in the range of 45/55 to 85/15; or more particularly in the range of 40/60 to 65/35; or more particularly in the range of 50/50 to 65/35. This composition may have an inherent viscosity (IV) in the range of 0.2 dL/g to 3.0 dL/g; or more particularly in the range of 1.0 dL/g to 2.0 dL/g. This composition may have a molecular weight in the range of 100,000 g/mol to 200,000 g/mol. This composition may have a crystallinity below 20%; or more particularly below 5%; or more particularly at 0% (i.e., a completely amorphous polymer). This composition may have a glass transition temperature (Tg) below 0° C.; or more particularly below −20° C. One particular example of this composition has a ratio of 50/50 PCL/PGA; an inherent viscosity (IV) of 0.2; a molecular weight of 83,000 g/mol; and a glass transition temperature (Tg) of −19.4°. Another particular example of this composition has a ratio of 65/35 PCL/PGA; an inherent viscosity (IV) of 1.04 to 1.07; a molecular weight of 110,000 g/mol to 118,000 g/mol; and a glass transition temperature (Tg) in the range of −37.3° to −38.6°.

Other exemplary synthetic based polymer compositions that may be used to form the adhesive material include the following: propanediol and caprolactone (PDO/PCL); a combination of propanediol, caprolactone, and trimethylene carbonate (PDO/PCL/TMC), with very low to no crystallinity and a glass transition temperature (Tg) below 0° C.; and a homopolymer poly(TMC), with an inherent viscosity (IV) of approximately 0.5 dL/g. Other suitable synthetic based polymer compositions will be apparent to those of ordinary skill in the art in view of the teachings herein.

The adhesive material may include a blocky copolymer. For instance, one example of a blocky copolymer that may be used in the adhesive material comprises blocky poly (TMC), with a low glass transition temperature (Tg). In some instances, the blocky copolymer may be randomized. In some other instances, such as when the copolymer is amorphous (e.g., 0% crystallinity), the blocky copolymer may be ordered.

The adhesive material may include various kinds of copolymer chain compositions. For instance, the copolymer chain composition may be branched with relatively short segments. This may further enhance the malleability experience. Alternatively, the copolymer chain may be linear. As another alternative, the copolymer may be cross-linked or star pattern. However, in versions where the copolymer is cross-linked, it may be desirable for the base copolymer segments to be more amorphous the more that those segment are cross-linked.

As noted above, the melting temperature (Tm) is a physiomechanical property of a polymer that may be selected to provide desired adhesive characteristics. In some instances, the lower melting temperature (Tm) of a monomer component could limit the amount of the co-monomer needed to create a desired adhesive effect. By way of example only, polydioxanone (PDS) has a melting temperature (Tm) around approximately 110° C. and a glass transition temperature (Tg) around approximately −10° C. Thus, polydioxanone (PDS) may need less caprolactone (PCL) to make a suitable pressure sensitive adhesive (PSA) copolymer. It should also be understood that polydioxanone (PDS) copolymers with polyglycolide (PGA) or lactide (PLA) may provide desired adhesive effects. It may be desirable for such copolymers to have a glass transition temperature (Tg) that is below room temperature; a melting temperature (Tm) that is at or below room temperature; a crystallinity in the range of 10% to 0%; and an inherent viscosity (IV) that is less than 2.0 dL/g, or more particularly less than 1.0 dL/g.

In some examples the adhesive material may comprise a blended copolymer. For instance, the high and low molecular weight of the same pressure sensitive adhesive (PSA) copolymer may allow for the degradation rate to be adjusted without adjusting the polymer chemistry. As the low molecular weight version breaks down, its acid byproducts would then change the pH and effect the breakdown of the high molecular weight parts. Preferred blends of copolymers would include those that will not affect the crystallinity, low melting temperature (Tm), and low glass transition temperature (Tg) of the copolymers.

Some examples of the adhesive material may comprise polyurethane. For instance, the polyurethane may be provided as a pressure sensitive adhesive (PSA). By of example only, polyurethane based pressure sensitive adhesives (PSAs) may be prepared from isocyanates, polyols, and chain extenders. Pressure sensitive adhesives (PSAs) may also be prepared from 100% solids, waterborne, or solvent borne systems. The properties of polyurethane based pressure sensitive adhesives (PSAs) may be controlled by varying the ratio of isocyanates to polyols and chain extenders. As another merely illustrative example, the polyurethane may be provided in a flowable form. For instance, a flowable polyurethane based adhesive material may have an inherent viscosity (IV) that is less than 1.0 dL/g, or more particularly less than 0.5 dL/g; a glass transition temperature (Tg) that is in the range of −10° C. and 10° C.; or more particularly closer to −10° C.; and a consistency similar to that of honey or oil, if desired, with the proper inherent viscosity (IV).

The foregoing examples of absorbable synthetic based polymers are provided for merely illustrative purposes. Other suitable examples will be apparent to those of ordinary skill in the art in view of the teachings herein. It should also be understood that the foregoing examples of absorbable synthetic based polymers may be readily incorporated into the various teachings and examples provided below. In other words, the foregoing examples of absorbable synthetic based polymers may be readily incorporated into any example herein that refers to an adhesive material.

B. Exemplary Polymeric Adhesive Materials with Natural Base

While the above discussion provides various examples of synthetic based polymers that may be used as an adhesive material (e.g., one or more of layers (104, 106)) for a buttress body (102), it should also be understood that a natural based polymer may be used as an adhesive material. Several merely illustrative examples of natural based polymers that may be used as an adhesive material will be described in greater detail below. It should also be understood that these examples of adhesive materials may be provided in upper adhesive layer (104). In addition or in the alternative, these examples of adhesive materials may be provided in lower adhesive layer (106). In addition or in the alternative, these examples of adhesive materials may be otherwise integrated into buttress body (102). It should therefore be understood that the adhesive material need not necessarily constitute a separate layer that is discretely identifiable as being different from a layer defined by buttress body (102).

In some instances, the adhesive material comprises a hydrogel. The hydrogel may generally comprise a hydrophilic polymer network capable of absorbing and/or retaining fluids. An exemplary hydrogel material is glycol methacrylate. By way of further example only, suitable hydrogel materials may comprise homopolymer hydrogels, copolymer hydrogels, multipolymer hydrogels, interpenetrating polymer hydrogels, and combinations thereof. In further examples, the hydrogel may comprise microgels, nanogels, and combinations thereof. The hydrogel may further comprise a non-crosslinked hydrogel, a crosslinked hydrogel, and combinations thereof. The hydrogel may comprise chemical crosslinks, physical crosslinks, hydrophobic segments and/or water insoluble segments. The hydrogel may be chemically crosslinked by polymerization, small-molecule crosslinking, and/or polymer-polymer crosslinking.

The hydrogel may be physically crosslinked by ionic interactions, hydrophobic interactions, hydrogen bonding interactions, sterocomplexation, and/or supramolecular chemistry. The hydrogel may be substantially insoluble due to the crosslinks, hydrophobic segments and/or water insoluble segments, but be expandable and/or swellable due to absorbing and/or retaining fluids. In some versions, the precursor may crosslink with endogenous materials and/or tissues.

Further examples of hydrogels that may be used include multifunctional acrylates, hydroxyethylmethacrylate (HEMA), and elastomeric acrylates. In additional or in the alternative, a hydrogel adhesive material may be constructed in accordance with at least some of the teachings of U.S. Pat. Pub. No. 2012/0241492, entitled "Tissue Thickness Compensator Comprising at Least One Medicament," published Sep. 27, 2012, issued as U.S. Pat. No. 9,839,420 on Dec. 12, 2017, the disclosure of which is incorporated by reference herein. Other suitable ways in which an adhesive material may be provided with hydrogel will be apparent to those of ordinary skill in the art in view of the teachings herein.

Further examples of naturally based polymers that may be used to form an adhesive material include alginate (e.g., calcium alginate, calcium sodium alginate, etc.); hyaluronic acid, collagen (including gelatin), and polysaccharide. In versions including a polysaccharide, the polysaccharide may include cellulose, chitin, pectin, or arabinoxylans. In versions including cellulose, the cellulose may comprise oxidized regenerated cellulose, carboxy-methylcellulose, carboxyethyl cellulose, hydroxypropyl cellulose, hydroxyethyl cellulose, or oxidized cellulose. In versions including chitin, the chitin may comprise chitosan (e.g., deacetylated chitin) or chitosan salts.

Some versions of naturally based polymers that may be used to form an adhesive material may include a putty or wax-like material. Some such versions may be non-absorbable and may be similar to a conventional bone wax. For instance, the material may comprise beeswax with one or more of the paraffin, petroleum jelly, isopropyl palmitate, sesame oil, carbolic acid; or any other conventional bone wax composition. Some other versions of a putty or wax-like material that may be used to form an adhesive material for buttress body (102) may be absorbable or resorbable. For instance, some such versions may comprise HEMASORB® putty by Abyrx, Ink of Irvington, N.Y., water-soluble alkylene copolymers (e.g., OSTENE by Baxter Healthcare Corporation of Deerfield, Ill.), glycerol, 1-lactide, glycolide, polyethylene glycol (PEG), polyethylene oxide (PEO), or polyolefin elastomer (POE). By way of further example, the adhesive material may comprise polyethylene glycol (PEG) or a polyethylene glycol (PEG) copolymer with a molecular weight of less than 20,000 g/mol. Having the molecular weight in such a range may promote passage of the dissolved form of the adhesive through the kidneys. See, e.g., Webster et al., "PEGylated Proteins: Evaluation of Their Safety in the Absence of Definitive Metabolism Studies," *Drug Metabolism and Disposition*, Vol. 35, No. 1, pp. 9-16 (2007), the disclosure of which is incorporated by reference herein. As yet another merely illustrative example, the adhesive material may be constructed in accordance with at least some of the teachings of U.S. Pat. No. 2,642,375, entitled "Hemostatic Compositions," issued Jun. 16, 1953, the disclosure of which is incorporated by reference herein.

Some polymer adhesives, including but not limited to the putty or wax-like compositions referred to above, may include oxidized regenerated cellulose (ORC), which is a hemostatic agent. For instance, a putty or wax-like composition may serve as a carrier for oxidized regenerated cellulose (ORC). U.S. Patent Pub. No. 2012/0241493, entitled "Tissue Thickness Compensator Comprising Controlled Release and Expansion," published Sep. 27, 2012, issued as U.S. Pat. No. 10,123,798 on Nov. 13, 2018, the disclosure of which is incorporated by reference herein, discusses various ways in which oxidized regenerated cellulose (ORC) may be incorporated into various compositions. It should be understood that such teachings of U.S. Patent Pub. No. 2012/0241493, issued as U.S. Pat. No. 10,123,798 on Nov. 13, 2018, may be readily applied herein in the context of incorporating oxidized regenerated cellulose (ORC) into polymer adhesives, including but not limited to the putty or wax-like compositions referred to above.

The foregoing examples of natural based polymers are provided for merely illustrative purposes. Other suitable examples will be apparent to those of ordinary skill in the art in view of the teachings herein. It should also be understood that the foregoing examples of natural based polymers may be readily incorporated into the various teachings and examples provided below. In other words, the foregoing examples of natural based polymers may be readily incorporated into any example herein that refers to an adhesive material.

C. Exemplary Surgical Staple Buttress with Integral Attachment and Reinforcement Features In some instances, it may be desirable to integrate attachment and reinforcement features into buttress body (102), in addition to or as an alternative to having one or more adhesive layers (104, 106) on upper or lower surfaces of buttress body (102). Such integral attachment and reinforcement features may enhance the attachment and reinforcement of buttress body (102) relative to tissue (90), relative to deck (73) of staple cartridge (70) and/or relative to underside (65) of anvil (60). The below examples include various exemplary configurations through which one or more attachment and reinforcement features may be combined with a buttress body (102) to enhance the attachment and reinforcement of buttress body (102) relative to tissue (90), relative to deck (73) of staple cartridge (70) and/or relative to underside (65) of anvil (60). In the present example, it is contemplated that the adhesive materials comprise a synthetic based polymer such as those referred to herein. By way of example only, an adhesive material composition that may be used in the below example may include a 65/35 a copolymer of caprolactone and glycolide (PCL/PGA) having a low inherent viscosity (IV) and low crystallinity. Other suitable compositions will be apparent to those of ordinary skill in the art in view of the teachings herein. It should also be understood that naturally based polymers may be incorporated with the below teachings.

1. Exemplary Buttress Assembly with Post-Stapling Adhesive Flow

Figure 20:
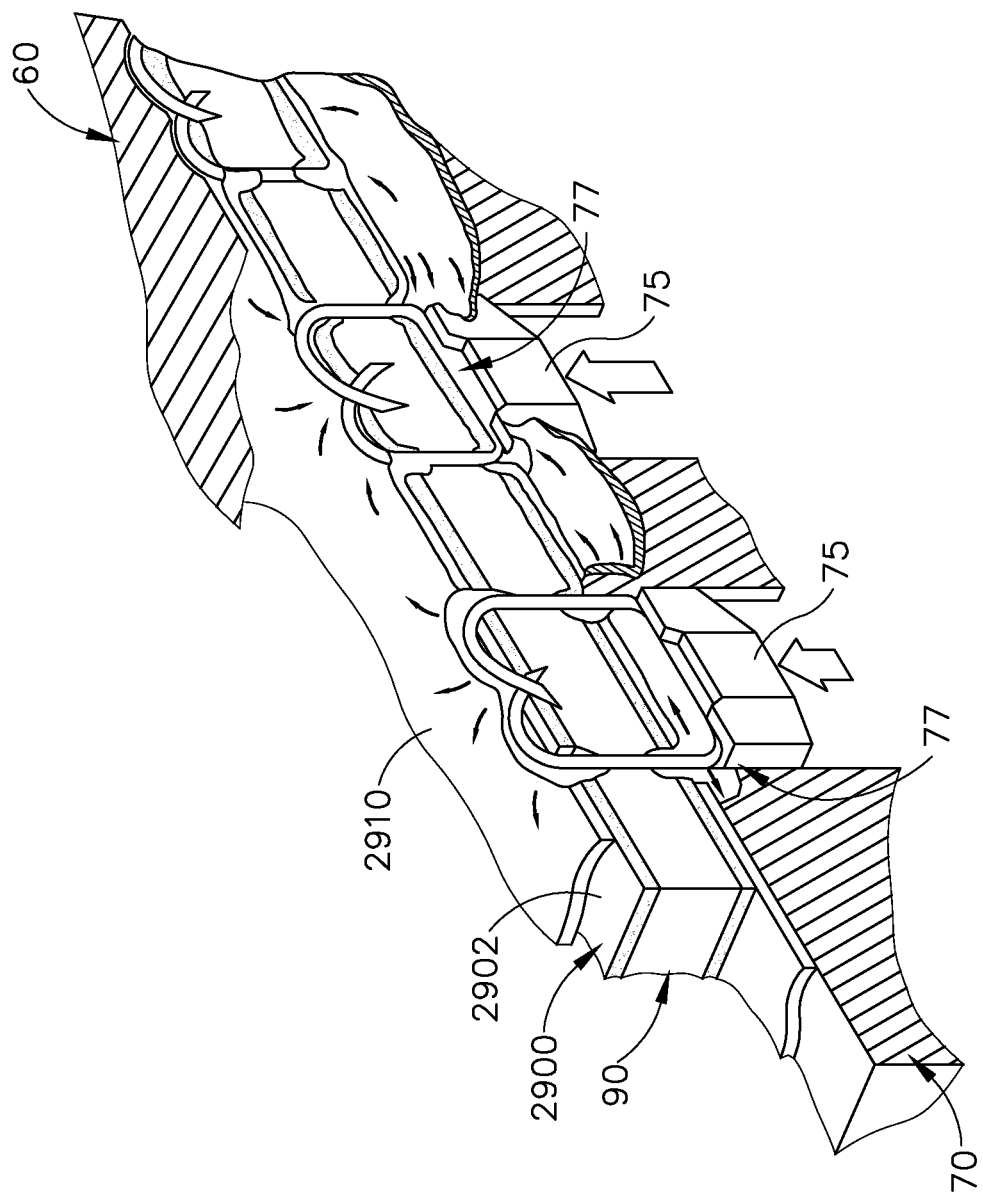
FIG. 20 depicts a perspective cross-sectional view of staples being driven through tissue and a buttress assembly.
Figure 21A:
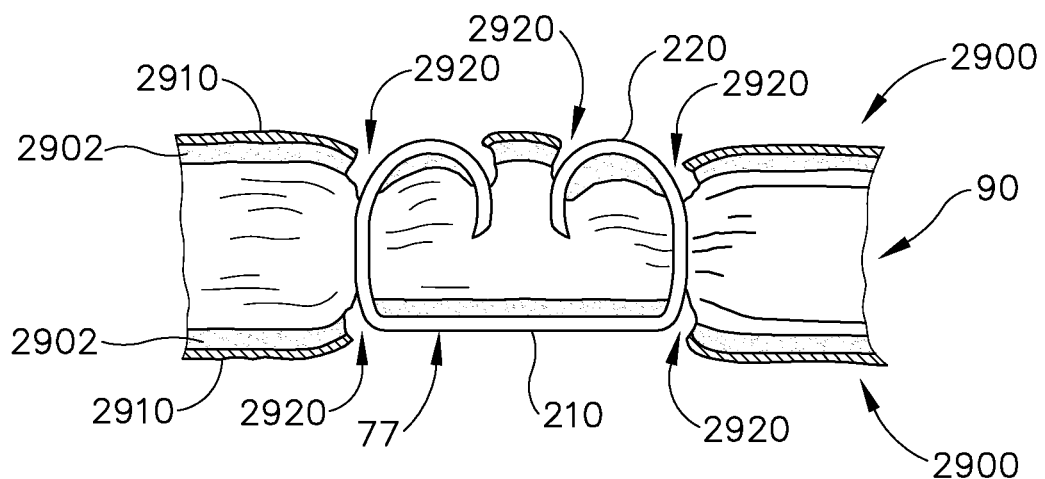
FIG. 21A depicts a perspective cross-sectional view of a staple driven through tissue and a buttress assembly, at a stage immediately after the staple has been driven through the tissue and buttress assembly.
Figure 21B:
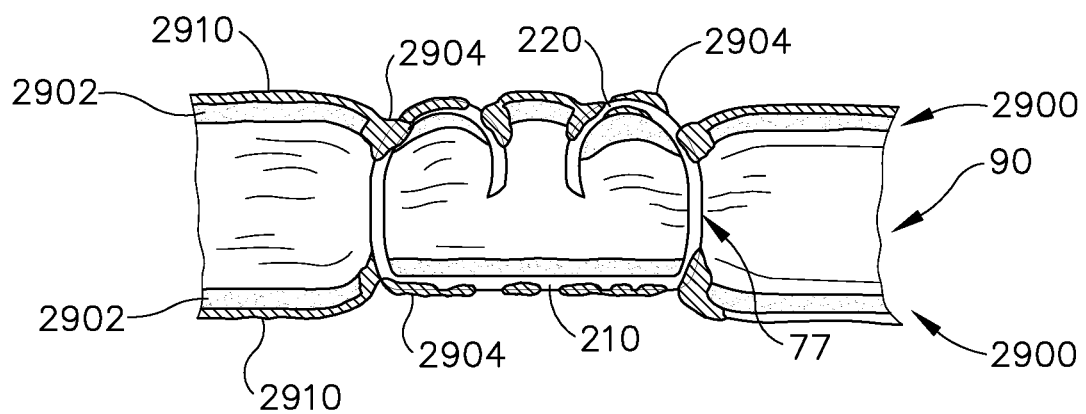
FIG. 21B depicts a perspective cross-sectional view of a staple driven through tissue and a buttress assembly, at a stage where an adjunct material has migrated into gaps around the staple legs.

FIGS. 20-21B show an exemplary buttress assembly (2900) that comprises a buttress body (2902) that contains an adhesive adjunct material (2904). Adhesive adjunct material (2904) may have a low viscosity enabling adhesive adjunct material (2904) to flow out of buttress body (2902) when buttress body (2902) is compressed. Various suitable compositions that may be used to provide adhesive adjunct material (2904) will be apparent to those of ordinary skill in the art in view of the teachings herein. Buttress body (2902) may have a fibrous structure, porous structure, and/or any other suitable kind of structure that is configured to absorb or otherwise contain adhesive adjunct material (2904). Various suitable materials and structures that may be used to provide buttress body (2902) will be apparent to those of ordinary skill in the art in view of the teachings herein.

A pressure sensitive, impermeable adhesive film (2910) is secured to one surface of buttress body (2902). Being impermeable, adhesive film (2910) is configured to prevent adhesive adjunct material (2904) from flowing out of that surface of buttress body (2902). Adhesive film (2910) is also configured to removably secure buttress assembly (2900) to underside (65) of anvil (60) or deck (73) of staple cartridge (70). In particular, adhesive film (2910) includes a pressure sensitive adhesive that provides enough adhesive strength to temporarily secure buttress assembly (2900) to underside (65) of anvil (60) or deck (73) of staple cartridge (70); yet the pressure sensitive adhesive also permits adhesive film (2910) to be pulled off of underside (65) of anvil (60) or deck (73) of staple cartridge (70) after end effector (40) has been actuated and staples (77) have been driven through buttress assembly (2900). Various suitable materials that may be used to form adhesive film (2910) will be apparent to those of ordinary skill in the art in view of the teachings herein. Similarly, various suitable materials that may be used to provide a pressure sensitive adhesive on or in adhesive film (2910) will be apparent to those of ordinary skill in the art in view of the teachings herein.

It should be understood that, when buttress assembly (2900) is loaded on retainer (300), the surface of upper side (302) or lower side (304) (depending on which side buttress assembly (2900) is loaded onto) may prevent adhesive adjunct material (2904) from flowing out of the surface of buttress body (2902) that is opposite to adhesive film (2910). FIGS. 20-21B show two buttress assemblies (2900), such that one buttress assembly (2900) would have been loaded onto upper side (302) of retainer (300) while the other buttress assembly (2900) would have been loaded onto lower side (304) of retainer (300). FIG. 20 in particular shows stapler drivers (75) driving staples (77) through tissue (90) and through both buttress assemblies (2900) as end effector (40) is being actuated. As shown in FIG. 21A, when staple (77) is initially driven through tissue (90) and buttress assemblies (2900), legs (220) of staple (77) tear through film (2910), creating gaps (2920) around crown (210) and staple legs (220). These gaps (2920) provide a path for adhesive adjunct material (2904) to flow out of buttress body (2902). Moreover, the series of applied staples (77) compress buttress assemblies (2900) against tissue (90), thereby urging adhesive adjunct material (2904) out of buttress body (2902) and into gaps (2920) as shown in FIG. 21B. This expelled adhesive adjunct material (2904) flows onto crown (210) and regions of legs (220) that would otherwise be exposed. The expelled adhesive adjunct material (2904) may eventually cure and thereby further reinforce the structural integrity of the applied buttress assembly (2900); and/or further reinforce the attachment of staples (77) to buttress assemblies (2900). The expelled adhesive adjunct material (2904) may also provide a hemostatic effect by blocking the flow of blood that might otherwise occur through gaps (2920).

In some variations of buttress assembly (2900), the adhesive adjunct material (2904) is provided in a layer that is laid over buttress body (2902) (in addition to or in lieu of being absorbed in or otherwise contained in buttress body (2902)). For instance, the adhesive adjunct material (2904) may be provided in a layer that is either used to replace impermeable adhesive film (2910) or in a layer that is interposed between buttress body (2902) and impermeable adhesive film (2910). Other suitable configurations will be apparent to those of ordinary skill in the art in view of the teachings herein.

2. Exemplary Buttress Assembly with Integral Fastening Strands

Figure 22:
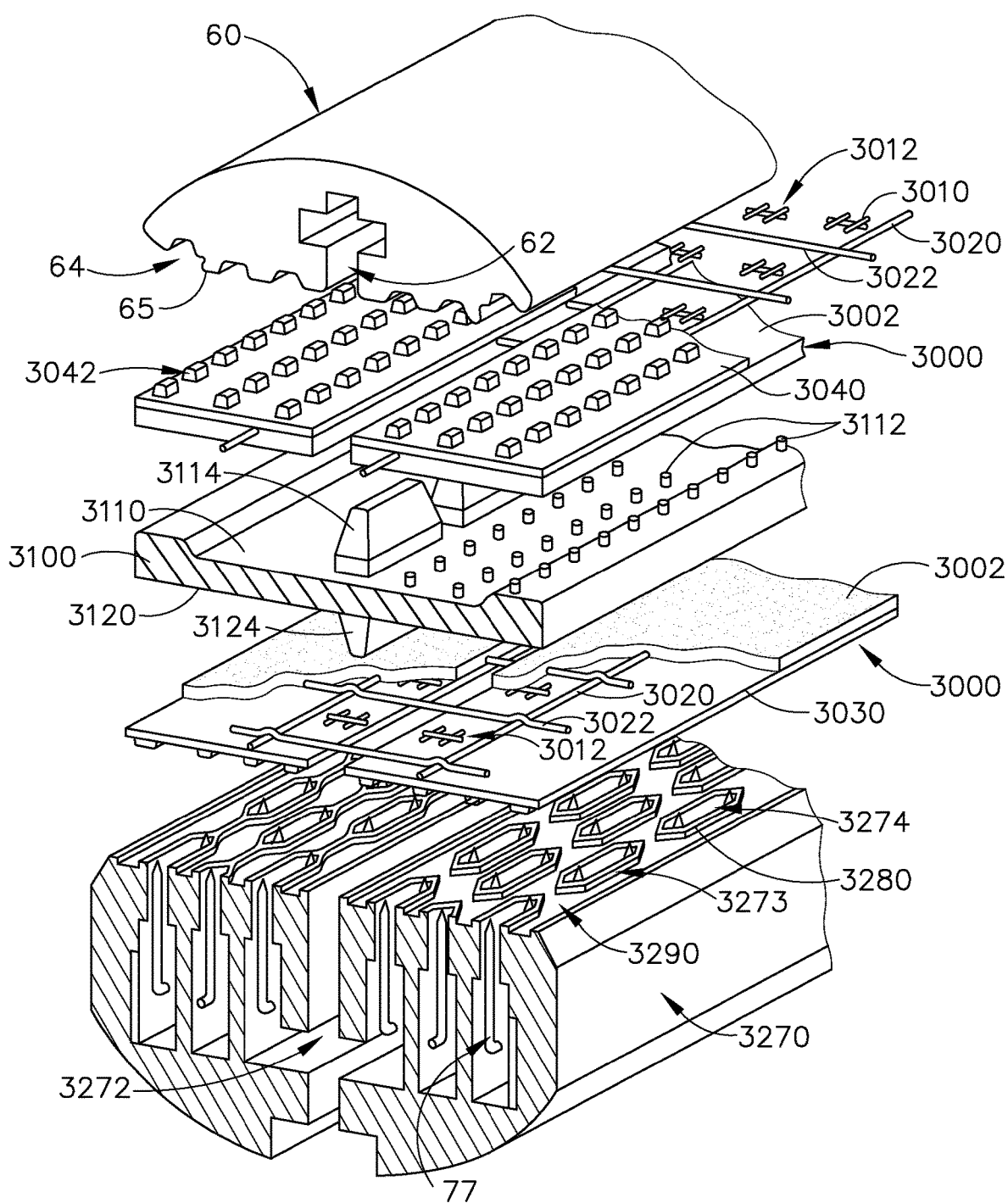
FIG. 22 depicts an exploded, perspective cross-sectional view of an exemplary end effector assembly, retainer, and pair of buttress assemblies.
Figure 23:
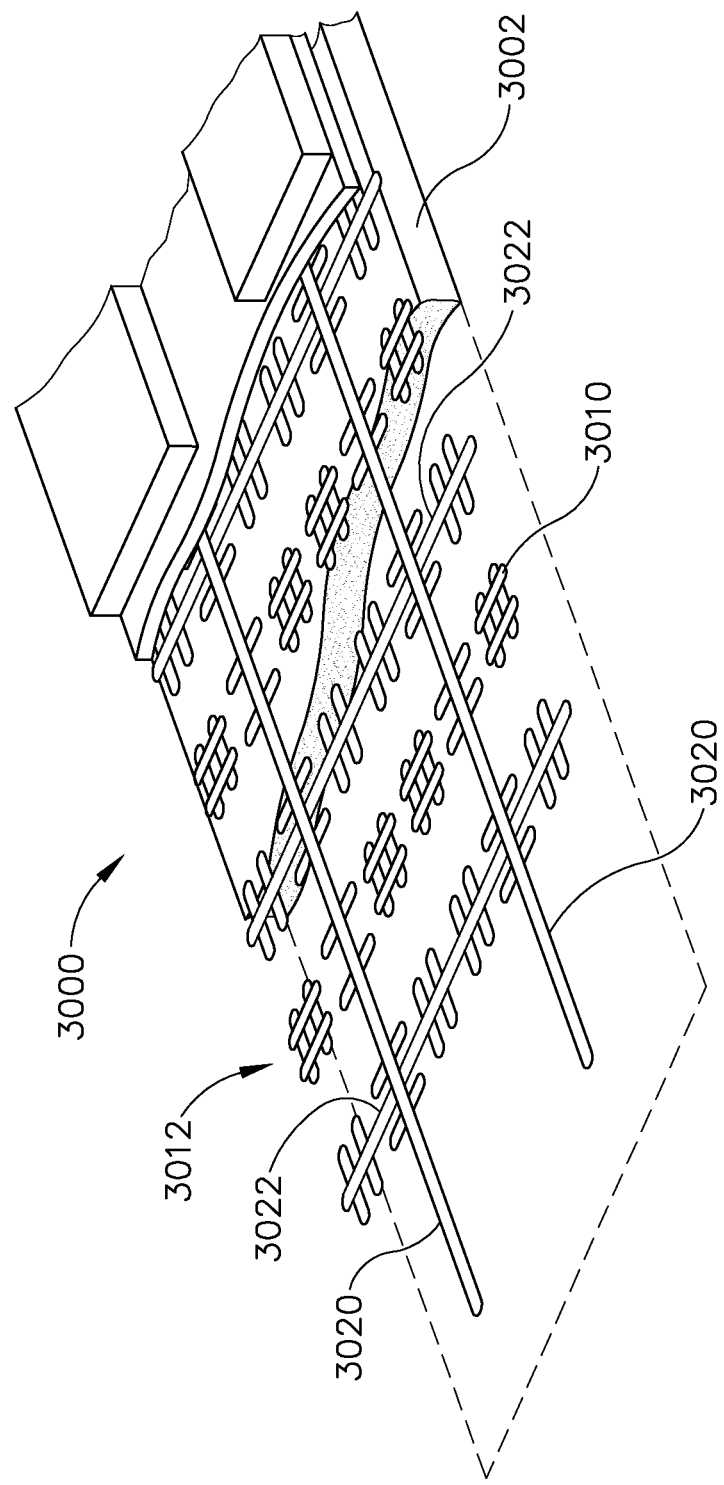
FIG. 23 depicts a partial perspective view of one of the buttress assemblies of FIG. 22.

FIGS. 22-26 show another exemplary buttress assembly (3000) with an exemplary alternative retainer (3100). Two buttress assemblies (3000) are shown, including one buttress assembly (3000) that is positioned to attach to underside (65) of anvil (60) and another buttress assembly (300) that is positioned to attach to a deck (3273) of a staple cartridge (3270). As best seen in FIG. 23, each buttress assembly (3000) of this example comprises a buttress body (3002) with a set of fastening strands (3010) woven therethrough. Buttress body (3002) may be configured and operable in accordance with any of the various buttress bodies referred to herein. By way of example only, fastening strands (3010) may comprise VICRYL® (polyglactin 910) suture material by Ethicon US, LLC. Alternatively, any other suitable material(s) may be used. In the present example, strands (3010) are provided only in a series of small, discrete woven regions (3012). In other words, strands (3010) are not woven throughout the entire buttress body (3002) in this example. The discrete woven regions (3012) of strands (3010) are positioned at locations where staples (77) will be driven through buttress assembly (3000), as will be described in greater detail below. In some other versions, strands (3010) are woven throughout the entire buttress body (3002) or in some other arrangement.

As also shown in FIG. 23, buttress assembly (3000) further includes a set of reinforcement members (3020, 3022). Reinforcement members (3020, 3022) may also comprise VICRYL® (polyglactin 910) suture material and/or any other suitable material(s). Each reinforcement member (3020) extends longitudinally along the full length of buttress body (3002). Reinforcement members (3022) extend transversely across the full width of buttress body (3002). Reinforcement members (3022) also span a gap (3004) defined between a pair of buttress bodies (3002), providing a connection of buttress bodies (3002) across gap (3004). In some versions, reinforcement members (3020, 3022) pass through discrete woven regions (3012) of strands (3010), such that reinforcement members (3020, 3022) are included in the weave at some of the discrete woven region (3012). In addition or in the alternative, reinforcement members (3020, 3022) may themselves be at least partially woven through buttress bodies (3002).

Figure 24:
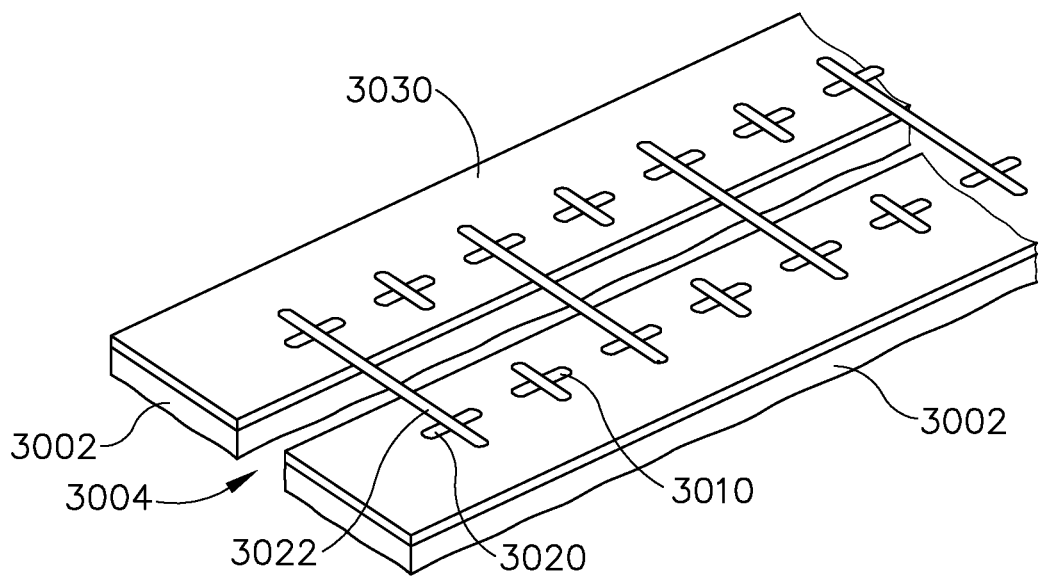
FIG. 24 depicts a perspective view of some elements of one of the buttress assemblies of FIG. 22.

As best seen in FIG. 24, buttress assembly (3000) further includes an impermeable layer (3030) laid over buttress body (3002). In the present example, strands (3010) and reinforcement members (3022) are partially woven through impermeable layer (3030); while reinforcement member members (3022) are positioned over impermeable layer (3030). In some other versions, impermeable layer (3030) is substituted with a semi impermeable layer, such as a layer of polydioxanone (PDS) and/or some other material(s). Various suitable materials that may be used to form impermeable layer (3030) (or a semi impermeable substitute therefor) will be apparent to those of ordinary skill in the art in view of the teachings herein.

Figure 25:
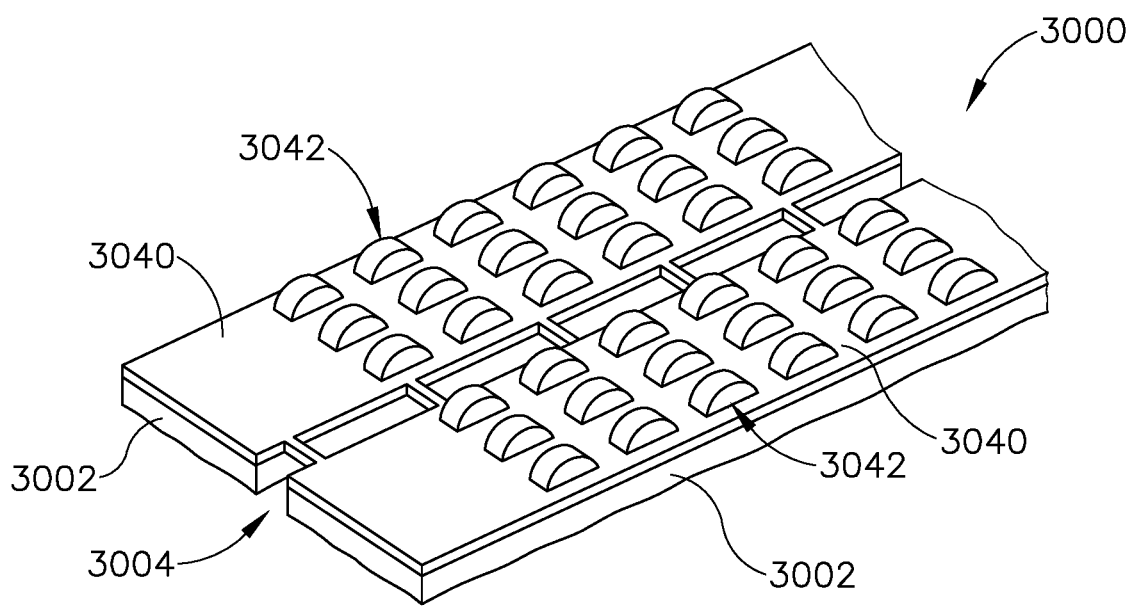
FIG. 25 depicts a perspective view of an assembled form of one of the buttress assemblies of FIG. 22.

As best seen in FIG. 25, buttress assembly (3000) further includes an impermeable peel-away film (3040) laid over impermeable layer (3030). Peel-away film (3040) defines a plurality of pockets (3042) that are configured to retain a flowable adhesive material (3050) (shown in FIG. 26) in an array of discretely formed droplets on impermeable layer (3030). Peel-away film (3040) is configured to adhere to impermeable layer (3030) during storage and transport of buttress assembly (3000), but may be peeled away to expose the flowable adhesive material (3050) under pockets (3042)

right before buttress assembly (3000) is installed on end effector (40). The discrete droplets of adhesive material (3050) are sized and positioned to correspond with the positioning of staple forming pockets (64) of anvil (60). Thus, the discrete droplets of adhesive material (3050) and pockets (3042) are arranged in three longitudinally extending linear arrays. Alternatively, any other suitable arrangement may be used. Various suitable materials that may be used to form peel-away film (3040) will be apparent to those of ordinary skill in the art in view of the teachings herein.

Referring back to FIG. 22, retainer (3100) has an upper surface (3110) and a lower surface (3120). A first pair of buttress assemblies (3000) are positioned on upper surface (3110) for adhesion of those buttress assemblies (3000) to underside (65) of anvil (60). A second pair of buttress assemblies (3000) are positioned on lower surface (3120) for adhesion of those buttress assemblies (3000) to deck (3273) of staple cartridge (3270). Upper surface (3110) includes an upwardly projecting, longitudinally extending rib (3114). Rib (3114) is sized to complement channel (62) of anvil (60). Lower surface (3120) also includes a downwardly projecting, longitudinally extending rib (3124), which is sized to complement channel (3272) of staple cartridge (3270). When anvil (60) is moved to a closed position to compress retainer (3100) and buttress assemblies (3000) between anvil (60) and staple cartridge (3270), ribs (3114, 3124) enter corresponding channels (62, 3472) and prevent flowable adhesive material (3050) from entering channels (62, 3472). Ribs (3114, 3124) may also ensure proper lateral alignment of retainer (3100) and buttress bodies (3000) with anvil (60) and staple cartridge (3270).

Upper surface (3110) of the present example further includes a plurality of upwardly extending projections (3112). While projections (3112) are only shown on one side of rib (3114), it should be understood that projections (3112) may also be located on the other side of rib (3114). Projections (3112) are configured and positioned to correspond with staple forming pockets (64) on underside (65) of anvil (60); and pockets (3042) of peel-away film (3040). When anvil (60) is moved to a closed position to compress retainer (3100) and buttress assemblies (3000) between anvil (60) and staple cartridge (3270), projections (3112) are configured to provide focused pressure to regions of buttress bodies (3002) at regions corresponding to staple forming pockets (64) the droplets of adhesive material (3050) formed by pockets (3042). While not shown, it should be understood that lower surface (3120) may also include downwardly extending projections, similar to projections (3112), to provide focused pressure to selected regions of buttress bodies (3002).

As also shown in FIG. 22, staple cartridge (3270) of the present example is substantially similar to staple cartridge (70) in that staple cartridge (3270) of this example includes channel (3272) and staple pockets (3274). However, staple cartridge (3270) of this example differs from staple cartridge (70) in that staple cartridge (3270) of this example includes upwardly extending walls (3280) that surround each staple pocket (3274), the outer edges of deck (3273), and the edges of deck (3273) adjacent to channel (3272). Walls (3280) thus define troughs (3290) that are configured to prevent adhesive material (3050) from flowing into staple pockets (3274), over the outer edges of deck (3273), and into channel (3272). In some other variations, staple cartridge (3270) is simply substituted with staple cartridge (70) or some other kind of staple cartridge.

Figure 26:
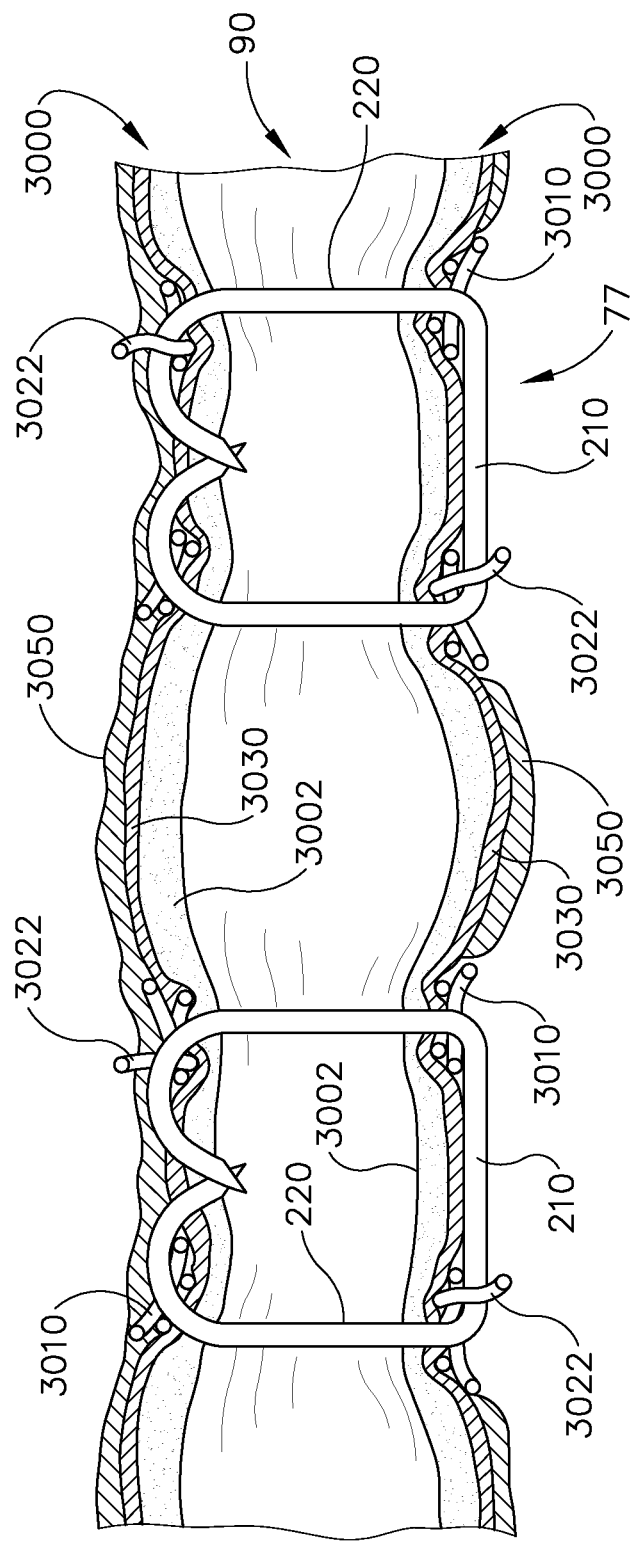
FIG. 26 depicts a cross-sectional view of staples driven through tissue and the buttress assemblies of FIG. 22.

FIG. 26 shows tissue (90) after an end effector formed by anvil (60) and staple cartridge (3270) has been actuated through the tissue (90). As shown, staples (77) secure buttress assemblies (3000) to the tissue (90). Crown (210) and legs (220) of each staple (77) capture strands (3010) and reinforcement members (3022), providing an attachment that may be more secure than what might otherwise be provided if buttress body (3002) lacked strands (3010) and reinforcement members (3022). It should be understood that, when firing beam (82) is advanced distally during actuation of the end effector, knife member (80) severs the portions of reinforcement members (3022) that span across gap (3004).

As is also shown in FIG. 26, some of the adhesive material (3050) remains on impermeable layer (3030). In some instances, this adhesive material (3050) may flow into gaps that might otherwise be present adjacent to crowns (210) and/or legs (220). The adhesive material (3050) may thus further reinforce the structural integrity of the applied buttress assembly (3000); and/or further reinforce the attachment of staples (77) to buttress assemblies (3000). The adhesive material (3050) may also provide a hemostatic effect by blocking the flow of blood that might otherwise occur through gaps that might otherwise be present adjacent to crowns (210) and/or legs (220). In some other variations, buttress assemblies (3000) are configured such that an appreciable amount of adhesive material (3000) is no longer present on impermeable layer (3030) after staples (77) are fired. Other suitable arrangements and compositions will be apparent to those of ordinary skill in the art in view of the teachings herein.

3. Exemplary Buttress Assembly with Heat Sensitive Strands

Figure 27:
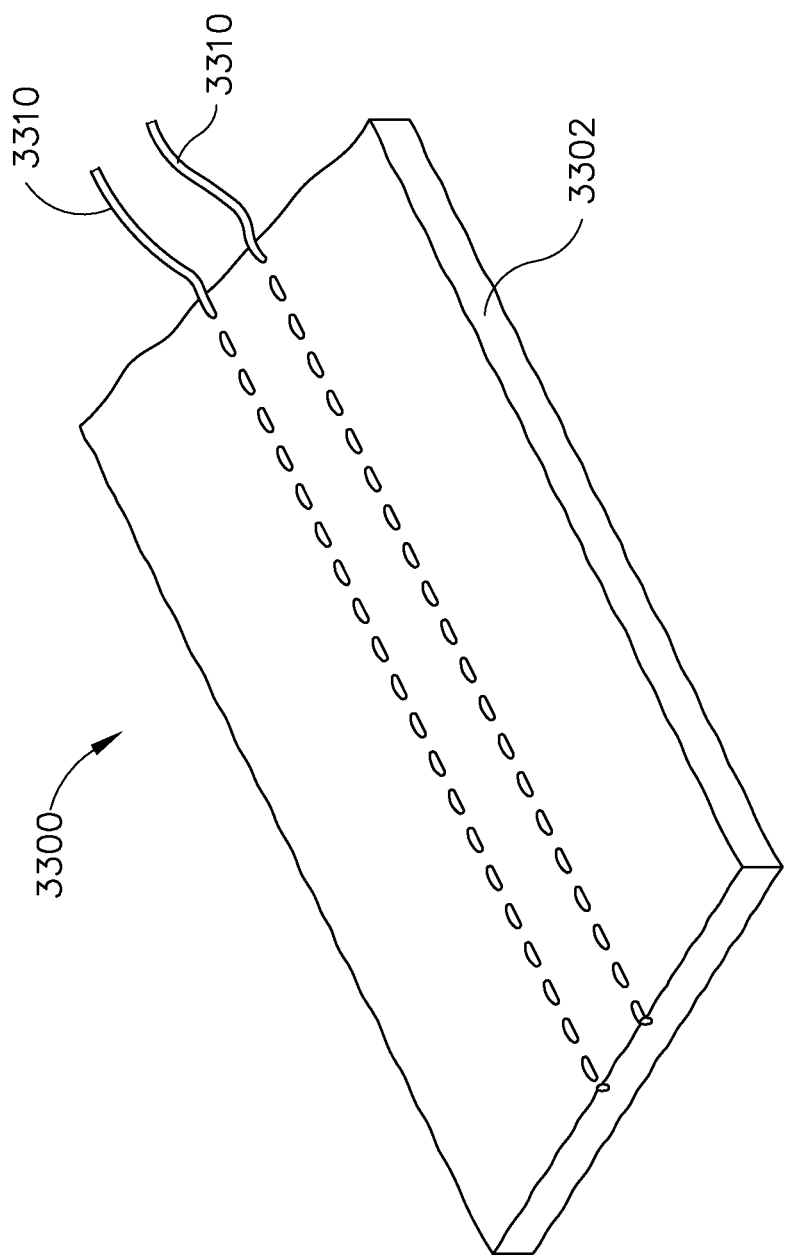
FIG. 27 depicts a perspective view of an exemplary alternative buttress assembly.
Figure 28:
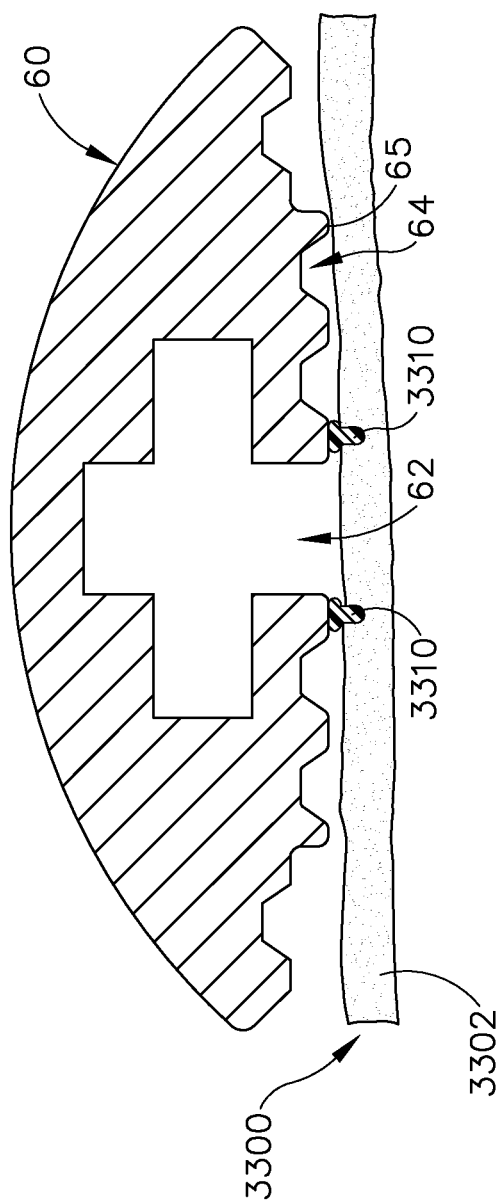
FIG. 28 depicts a cross-sectional end view of the buttress assembly of FIG. 27 applied to the anvil of the end effector of FIG. 3.
Figure 29:
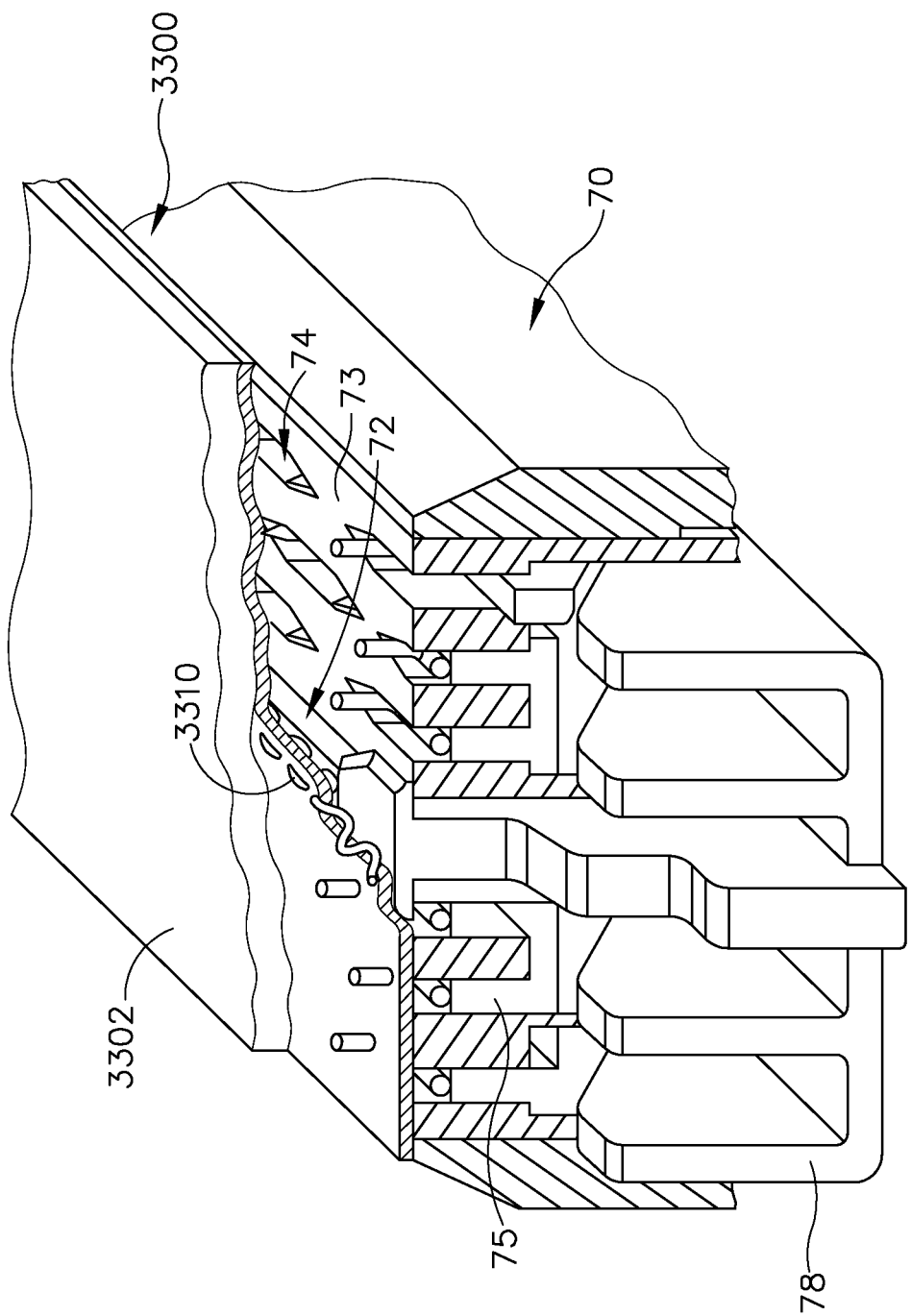
FIG. 29 depicts a partial, cross-sectional perspective view of the buttress assembly of FIG. 27 applied to the deck of the staple cartridge of the end effector of FIG. 3.

FIGS. 27-29 show another exemplary buttress assembly (3300). Buttress assembly (3300) of this example comprises a buttress body (3302) with a pair of heat sensitive strands (3310) woven through buttress body (3302). Buttress body (3302) may be formed in accordance with any buttress body referred to herein. Each heat sensitive strand (3310) is woven through buttress body (3302) such that heat sensitive strand (3310) extends along the full length of buttress body (3302). Heat sensitive strands (3310) are parallel to each other and are spaced apart by a distance complementing the lateral width of channels (62, 72). Heat sensitive strands (3310) are formed of a material that will melt at a relatively low temperature and adhere to a surface that it is in contact with when it melts and cools. The melting temperature (Tm) of heat sensitive strands (3310) is lower than the melting temperature (Tm) of buttress body (3302).

By way of example only, heat sensitive strands (3310) may comprise polydioxanone (PDS). In some such versions, buttress body (3302) comprises VICRYL® (polyglactin 910) material by Ethicon US, LLC, heat sensitive strands (3310) comprise polydioxanone (PDS), and buttress assembly (3300) is formed as a woven fleece material made from a 7:1 blend of VICRYL®:PDS that is heat treated to shrink polydioxanone (PDS) and bond individual fibers in the fleece together. Alternatively, any other suitable blend ratio may be used. In some versions where buttress assembly (3300) comprises a woven fleece material made from a blend of VICRYL® material and polydioxanone (PDS), the fleece may be attached to a polydioxanone (PDS) film that may be heated to secure buttress assembly (3300) to underside (65) of anvil (60) or deck (73) of staple cartridge (70).

As another merely illustrative example, buttress assembly (3300) may be constructed in accordance with at least some of the teachings of U.S. Pat. No. 5,686,090, entitled "Multi-Layered Implant," issued Nov. 11, 1997, the disclosure of which is incorporated by reference herein. Various other suitable materials that may be used to form heat sensitive strands (3310) will be apparent to those of ordinary skill in the art in view of the teachings herein. While buttress assembly (3300) only includes two heat sensitive strands (3310) in the depicted example, it should be understood that any other suitable number of heat sensitive strands (3310) may be incorporated into buttress assembly (3300) if desired.

FIG. 28 shows buttress assembly (3300) applied to underside (65) of anvil (60). As shown, heat sensitive strands (3310) are positioned on respective regions of underside (65) that are adjacent to channel (62). When buttress assembly (3300) is so positioned, heat sensitive strands (3310) may be heated to their melting point; then allowed to cool to thereby adhere buttress assembly (3300) to underside (65). By way of example only, buttress assembly (3300) may be applied to underside (65) using a modified version of retainer (300). For instance, such a modified version of retainer (300) may include a heating element at or under upper side (302). The heating element may be activated while anvil (60) is clamping down on buttress assembly (3300). Such a modified version of retainer (300) may also include a coating such as polytetrafluoroethylene (PTFE) to prevent heat sensitive strands (3310) from adhering to upper side (302). In addition or in the alternative, retainer (300) may include surface features that are configured to prevent heat sensitive strands (3310) from adhering to upper side (302). It should also be understood that heat sensitive strands (3310) may be woven through buttress body (3302) in such a way that heat sensitive strands (3310) will not contact upper side (302) of the modified retainer (300). Other suitable structures and techniques that may be used to provide heat to heat sensitive strands (3310) will be apparent to those of ordinary skill in the art in view of the teachings herein.

FIG. 29 shows buttress assembly (3300) applied to deck (73) of staple cartridge (70). As shown, heat sensitive strands (3310) are positioned on respective regions of deck (73) that are adjacent to channel (72). When buttress assembly (3300) is so positioned, heat sensitive strands (3310) may be heated to their melting point; then allowed to cool to thereby adhere buttress assembly (3300) to deck (73). By way of example only, buttress assembly (3300) may be applied to deck (73) using a modified version of retainer (300) as described above; or using any other suitable structures or techniques as will be apparent to those of ordinary skill in the art in view of the teachings herein.

4. Other Exemplary Buttress Assemblies

It should be understood that the adhesive material that removably secures a buttress body (102) to underside (65) of anvil (60) or to deck (73) of staple cartridge (70) may have various properties including malleability and tackiness that provides self-attachment to underside (65) of anvil (60) or to deck (73) of staple cartridge (70). In other words, the adhesive material may deform to the shape presented by the corresponding contact area of underside (65) or deck (73). It should also be understood that the adhesive material may be provided on buttress body (102) in various shapes and configurations. For instance, the adhesive material may be provided in a pattern that includes selective zones of adhesion to minimize the likelihood of collateral damage to areas such as staple pockets (74) whose performance might be adversely affected by influx of adhesive material. The pattern of the adhesive material may also minimize the number and size of the adhesive contact with underside (65) or deck (73), thereby minimizing the force required to pull buttress assembly (100) off of underside (65) or deck (73) after end effector (40) has been actuated. The geometry of the adhesive material may provide uniform thickness or variable thickness. The adhesive material may also provide variable stiffness. Providing a variable thickness and/or variable stiffness may provide a variable pressure distribution.

Figure 30:
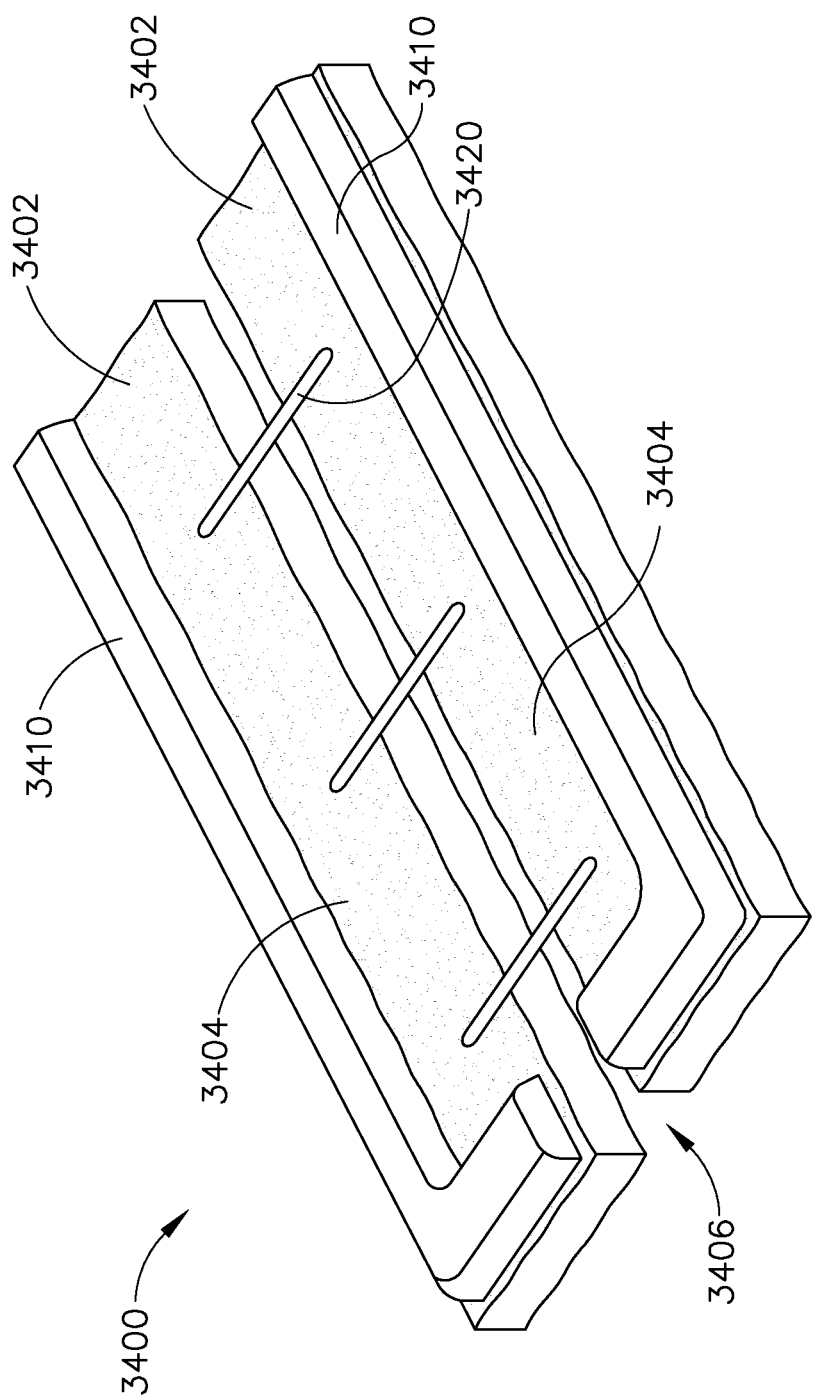
FIG. 30 depicts a perspective view of an exemplary alternative buttress assembly.

FIG. 30 shows an exemplary alternative buttress assembly (3400) that comprises a pair of buttress bodies (3402) and an adhesive material (3410) that is positioned along the outer perimeter of the upper surface (3404) of each buttress body (3402). Buttress bodies (3402) are separated by a gap (3406) that corresponds to channel (62) of anvil (60) and channel (72) of staple cartridge (70). A set of tethers (3420) extend transversely across gap (3406), connecting buttress bodies (3402). As described above with respect to other tethers, tethers (3420) of this example will be severed by knife member (80) when firing beam (82) is advanced distally during actuation of end effector (40). Due to the configuration and arrangement of adhesive material (3410), buttress assembly (3400) is only adhered to underside (65) or deck (73) along the outer perimeter of buttress body (3402), which may minimize the force required to pull buttress assembly (3400) off of underside (65) or deck (73) after end effector (40) has been actuated. Various suitable materials that may be used to form buttress bodies (3402), adhesive material (3410), and tethers (3420) will be apparent to those of ordinary skill in the art in view of the teachings herein.

Figure 31:
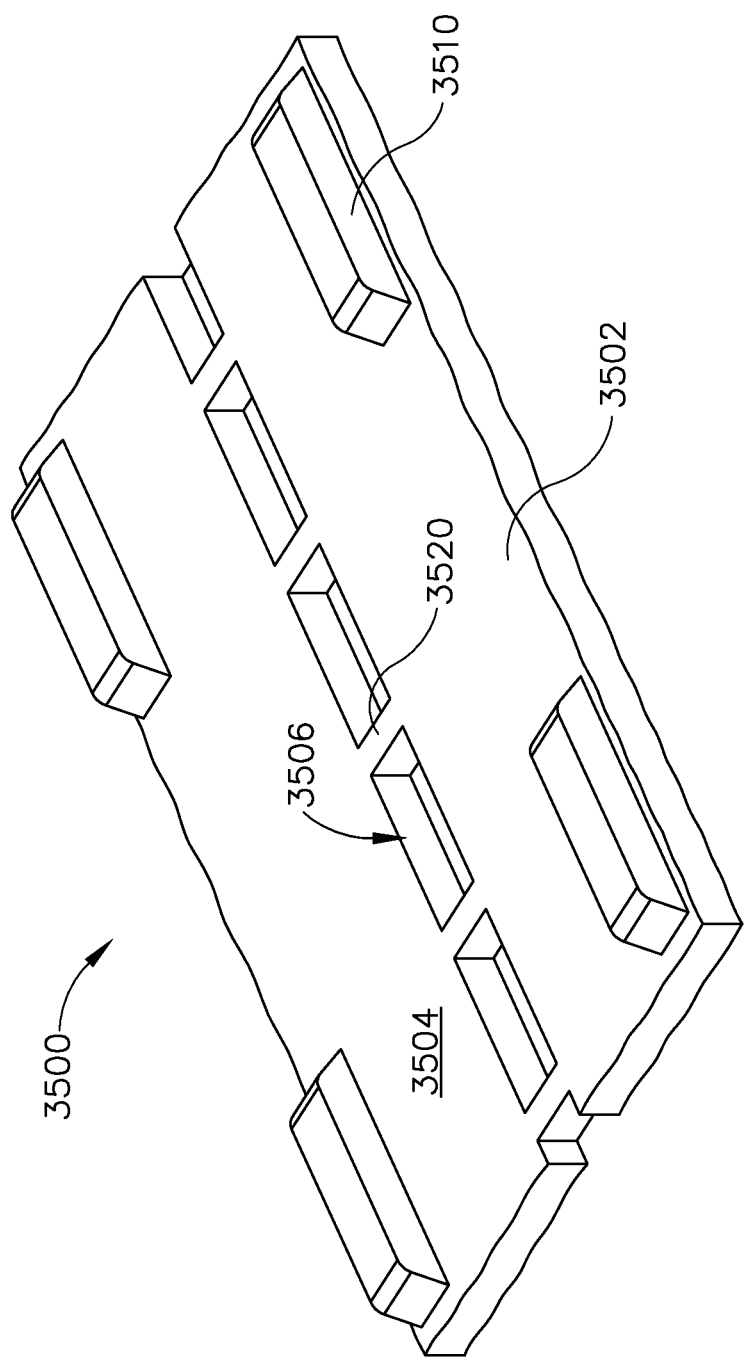
FIG. 31 depicts a perspective view of another exemplary alternative buttress assembly.

FIG. 31 shows another exemplary alternative buttress assembly (3500) that comprises a buttress body (3502) and an adhesive material (3510) that is positioned in discrete regions along the outer perimeter of the upper surface (3504) of buttress body (3502). Buttress body (3502) defines a longitudinally extending array of gaps (3506) that correspond to channel (62) of anvil (60) and channel (72) of staple cartridge (70). Buttress body (3502) further defines a set of transversely extending bridge regions (3520) that separate gaps (3506). As described above with respect to tethers, bridge regions (3520) of this example will be severed by knife member (80) when firing beam (82) is advanced distally during actuation of end effector (40). Due to the configuration and arrangement of adhesive material (3510), buttress assembly (3400) is only adhered to underside (65) or deck (73) at discrete regions along the outer perimeter of buttress body (3502), which may further minimize the force required to pull buttress assembly (3500) off of underside (65) or deck (73) after end effector (40) has been actuated. This pull-away force may be lower for buttress assembly (3500) than it is for buttress assembly (3400) since less adhesive material (3510) is used in buttress assembly (3500). Various suitable materials that may be used to form buttress body (3502) and adhesive material (3510) will be apparent to those of ordinary skill in the art in view of the teachings herein.

Figure 32:
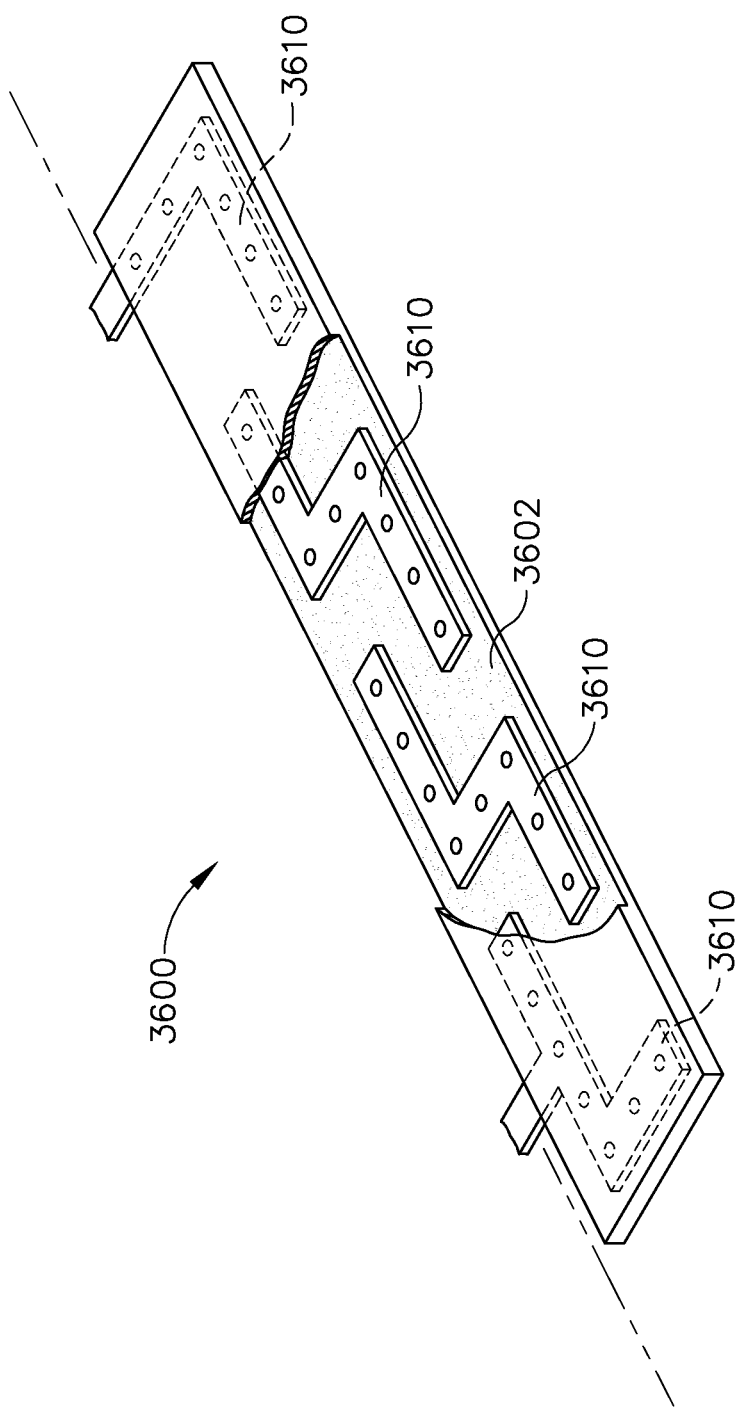
FIG. 32 depicts a perspective view of another exemplary alternative buttress assembly.

FIG. 32 shows yet another exemplary alternative buttress assembly (3600) that comprises a buttress body (3602) with a plurality of integral reinforcement members (3610). Buttress body (3602) may be configured and operable in accordance with any of the various buttress bodies described herein. An adhesive material (not shown) is incorporated into buttress body (3602) in order to provide removable attachment of buttress assembly (3600) to underside (65) of anvil (60) or deck (73) of staple cartridge (70). Various suitable compositions that may be used to provide the adhesive material, and various suitable ways in which such adhesive material may be incorporated into buttress body (3602), will be apparent to those of ordinary skill in the art in view of the teachings herein.

Reinforcement members (3610) are configured to provide structural reinforcement to buttress body (3602) and/or to the attachment of staples (77) that are driven through buttress assembly (3600). By way of example only, in some versions buttress body (3602) is formed of a porous sponge like material while reinforcement members (3610) are formed of a tight fibrous weave that has greater tensile strength than the material forming buttress body (3602). Various suitable materials and structures that may be used to form reinforcement members (3610) will be apparent to those of ordinary skill in the art in view of the teachings herein. In the present example, two of the reinforcement members (3610) have a generally "S" shaped configuration while the other two reinforcement members (3610) have a generally "L" shaped configuration. These shapes are configured to enable each reinforcement member (3610) to receive several staples (77) from different rows and columns of staple cartridge (70). By spanning across discrete sets of staples (77) from different rows and columns of staple cartridge (70), reinforcement members (3610) may provide greater reinforcement than what might otherwise be provided if reinforcement members (3610) spanned the entire array of staples (77) or just individual staples (77). Other suitable shapes and arrangements for reinforcement members (3610) will be apparent to those of ordinary skill in the art in view of the teachings herein. It should also be understood that reinforcement members (3610) may be integrated into buttress body (3602) in any suitable fashion, including but not limited to providing reinforcement members (3610) between apposed layers of buttress body (3602) or forming buttress body (3602) around reinforcement members (3610).

5. Exemplary Alternative Retainer

Figure 33:
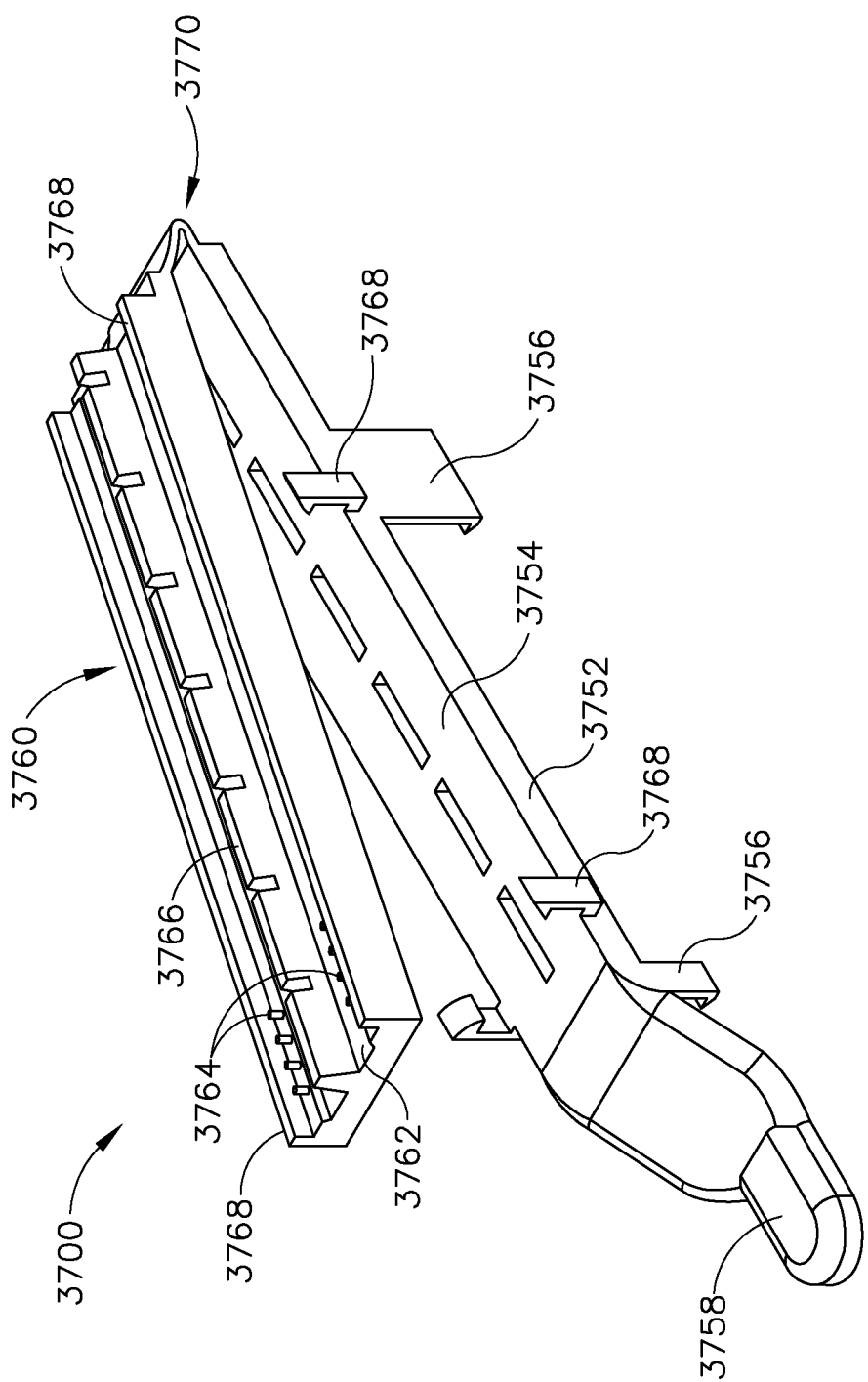
FIG. 33 depicts a perspective view of an exemplary alternative retainer.

FIG. 33 shows an exemplary alternative retainer (3700) that may be used with any of the various buttress assemblies described herein. Retainer (3700) of this example comprises a base member (3752) having an upper surface (3754), a plurality of latches (3756), and a distally projecting tongue (3758) that is configured to facilitate grasping and manipulation of retainer (3750). Retainer (3700) also includes an upper member (3760) that is secured to base member (3752) by a living hinge (3770). Upper member (3760) has an upper surface (3762) that is configured to engage buttress body (3702). Upper member (3760) includes a plurality of projections (3764) extending upwardly from upper surface (3762), and central rib (3766) extending upwardly and longitudinally along the laterally central region of upper surface (3762), and a pair of outer ribs (3768) extending upwardly and longitudinally along the outer edges of upper surface (3762). While projections (3764) are shown as spanning along only a portion of the length of upper surface (3762), it should be understood that projections (3764) may span along the entire length of upper surface. It should also be understood that projections (3764) may span along three rows on each side of central rib (3766), corresponding to three rows of staple forming pockets (64) on underside (65) of anvil (60).

It should be understood that retainer (3700) may be removably secured to end effector (40) in a manner similar to retainer (300) described above, with latches (3756) releasably engaging lower jaw (50). At such a stage, upper member (3760) is spaced away from upper surface (3754) of base member (3752) due to a resilient bias imposed by living hinge (3770). The resilient bias provided by living hinge (3770) may ensure that upper adhesive layer (104) of a buttress assembly (100) that is laid over upper surface (3762) will contact the appropriate region of underside (65) of anvil (60) before anvil (60) reaches a fully closed position. The resilient bias provided by living hinge (3770) may also provide and maintain a minimum consistent pressure during the closure of anvil (60) to enhance the attachment of upper adhesive layer (104) to underside (65) of anvil (60).

As anvil (60) is driven further toward the closed position, anvil (60) bears down on upper adhesive layer (104) and upper member (3760), thereby causing upper member (3760) to pivot toward base member (3752). Adhesive layer (104) is compressed between underside (65) of anvil (60) and projections (3764). Projections (3764) provide focused pressure to regions of buttress assembly (100) at regions corresponding to staple forming pockets (64) (and/or into other surface features of underside (65)), thereby further promoting adhesion between adhesive layer (104) and underside (65). Ribs (3766, 3768) may ensure proper lateral alignment of retainer (3700) and buttress assembly (100) with anvil (60) during the closure of anvil (60). Ribs (3766, 3768) may also prevent adhesive material from entering channel (62) or escaping from sides of anvil (60) during closure of anvil (60). When anvil (60) reaches the closed position, latches (3768) of retainer (3700) may secure upper member (3760) into apposition with base member (3752), facilitating removal of retainer (3750) from end effector (40). Buttress assembly (100) may then be left adhered to underside (65) of anvil (60), such that end effector (40) is then ready for use.

While retainer (3700) is described as being used in combination with buttress assembly (100), it should be understood that retainer (3700) may be used in combination with any other buttress assembly referred to herein.

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

EXAMPLE 1

A surgical stapler end effector assembly, the end effector assembly comprising: (a) a staple cartridge, wherein the staple cartridge comprises: (i) a plurality of staples, and (ii) a deck, wherein the staple cartridge is operable to drive the staples through the deck; (b) an anvil, wherein the anvil is movable from an open position toward the staple cartridge to reach a closed position, wherein the anvil includes an underside having staple forming surface configured to receive staples driven through the deck; and (c) a buttress assembly, wherein the buttress assembly comprises: (i) a buttress body, (ii) an adhesive material, wherein the adhesive material is configured to removably secure the buttress body to the deck of the staple cartridge or the underside of the anvil, and (iii) a plurality of reinforcement strands extending through the buttress body, wherein the reinforcement strands are configured to engage one or more staples fired through the buttress body.

EXAMPLE 2

The surgical stapler end effector assembly of Example 1 and any of the following Examples, wherein the adhesive material comprises a pressure sensitive adhesive.

EXAMPLE 3

The surgical stapler end effector assembly of any of the preceding or following Examples, wherein the reinforcement strands comprise polyglactin 910.

EXAMPLE 4

The surgical stapler end effector assembly of any of the preceding or following Examples, wherein at least some of the reinforcement strands are woven through the buttress body.

EXAMPLE 5

The surgical stapler end effector assembly of any of the preceding or following Examples, wherein at least some of the reinforcement strands are woven through the buttress body in discrete woven regions.

EXAMPLE 6

The surgical stapler end effector assembly of Example 5, wherein the staple cartridge is operable to drive the staples through the buttress body at regions corresponding to the discrete woven regions.

EXAMPLE 7

The surgical stapler end effector assembly of any of the preceding or following Examples, wherein the buttress body defines a length, wherein at least one of the reinforcement strands extends along the length of the buttress body.

EXAMPLE 8

The surgical stapler end effector assembly of any of the preceding or following Examples, wherein the buttress body defines a length, wherein at least one of the reinforcement strands extends transversely relative to the length of the buttress body.

EXAMPLE 9

The surgical stapler end effector assembly of any of the preceding or following Examples, wherein the buttress body comprises a pair of portions laterally spaced apart from each other by a gap.

EXAMPLE 10

The surgical stapler end effector assembly of Example 9, wherein at least one of the reinforcement strands extends across the gap.

EXAMPLE 11

The surgical stapler end effector assembly of any of the preceding or following Examples, wherein the buttress assembly further comprises an intermediate layer positioned between the buttress body and the adhesive material, wherein the intermediate layer is impermeable or semi-impermeable.

EXAMPLE 12

The surgical stapler end effector assembly of Example 11, wherein at least one of the reinforcement strands is positioned on or through the intermediate layer.

EXAMPLE 13

The surgical stapler end effector assembly of any of the preceding or following Examples, wherein the buttress assembly further comprises a film layer positioned over the adhesive material, wherein the film layer is impermeable.

EXAMPLE 14

The surgical stapler end effector assembly of Example 13, wherein the film layer is positioned over the plurality of reinforcement strands.

EXAMPLE 15

The surgical stapler end effector assembly of Example 13, wherein the film layer defines a plurality of pockets configured to contain the adhesive material in a plurality of discrete regions.

EXAMPLE 16

The surgical stapler end effector assembly of Example 15, further comprising a retainer assembly configured to releasably hold the buttress assembly, wherein the retainer assembly comprises a plurality of protrusions configured to engage the buttress assembly at locations corresponding to the discrete regions of adhesive material.

EXAMPLE 17

The surgical stapler end effector assembly of any of the preceding or following Examples, wherein each staple comprises a crown and a pair of legs, wherein at least one of the reinforcement strands is configured to engage either the crown or at least one of the legs of the staples.

EXAMPLE 18

A surgical stapler end effector assembly, the end effector assembly comprising: (a) a staple cartridge, wherein the staple cartridge comprises: (i) a plurality of staples, and (ii) a deck, wherein the staple cartridge is operable to drive the staples through the deck; (b) an anvil, wherein the anvil is movable from an open position toward the staple cartridge to reach a closed position, wherein the anvil includes an underside having staple forming surface configured to receive staples driven through the deck; and (c) a buttress assembly, wherein the buttress assembly comprises: (i) a buttress body, and (ii) a heat sensitive strand woven through the buttress body, wherein the heat sensitive strand is configured to melt in response to heat and thereby secure the buttress body to the underside of the anvil or the deck of the staple cartridge.

EXAMPLE 19

A surgical stapler end effector assembly, the end effector assembly comprising: (a) a staple cartridge, wherein the staple cartridge comprises: (i) a plurality of staples, wherein the staples are arranged in a plurality of rows and in a plurality of columns, and (ii) a deck, wherein the staple cartridge is operable to drive the staples through the deck; (b) an anvil, wherein the anvil is movable from an open position toward the staple cartridge to reach a closed position, wherein the anvil includes an underside having staple forming surface configured to receive staples driven through the deck; and (c) a buttress assembly, wherein the buttress assembly comprises: (i) a buttress body, wherein the buttress body comprises a porous material, (ii) an adhesive material, wherein the adhesive material is configured to removably secure the buttress body to the deck of the staple cartridge or the underside of the anvil, and (iii) a plurality of reinforcement members positioned on or in the buttress body, wherein the reinforcement members comprise a fibrous material, wherein each reinforcement member is configured to engage a respective set of staples fired through the buttress body, wherein each set of staples spans across a respective plurality of rows and columns.

EXAMPLE 20

The surgical stapler end effector assembly of Example 19, wherein at least one of the reinforcement members has an "L" shape or an "S" shape.

V. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; U.S. Pub. No. 2013/0012957, entitled y37 Automated End Effector Component Reloading System for Use with a Robotic System, published Jan. 10, 2013, issued as U.S. Pat. No. 8,844,789 on Sep. 30, 2014, the disclosure of which is incorporated by reference herein; U.S. Pub. No. 2012/0199630, entitled "Robotically-Controlled Surgical Instruments ," published Aug. 9, 2012, issued as U.S. Pat. No. 8,820,605 on Sep. 2, 2014, the disclosure of which is incorporated by reference herein; U.S. Pub. No. 2012/0132450, entitled "Shiftable Drive Interface for Robotically-Controlled Surgical Tool," published May 31, 2012, issued as U.S. Pat. No. 8,616,431 on Dec. 31, 2013, the disclosure of which is incorporated by reference herein; U.S. Pub. No. 2012/0199633, entitled "Surgical Stapling Instruments with Cam-Driven Staple Deployment Arrangements," published Aug. 9, 2012, issued as U.S. Pat. No. 8,573,461 on Nov. 5, 2013, the disclosure of which is incorporated by reference herein; U.S. Pub. No. 2012/0199631, entitled "Robotically-Controlled Motorized Surgical End Effector System with Rotary Actuated Closure Systems Having Variable Actuation Speeds," published Aug. 9, 2012, issued as U.S. Pat. No. 8,602,288 on Dec. 10, 2013, the disclosure of which is incorporated by reference herein; U.S. Pub. No. 2012/0199632, entitled "Robotically-Controlled Surgical Instrument with Selectively Articulatable End Effector," published Aug. 9, 2012, issued as U.S. Pat. No. 9,301,759 on Apr. 5, 2016, the disclosure of which is incorporated by reference herein; U.S. Pub. No. 2012/0203247, entitled "Robotically-Controlled Surgical End Effector System," published Aug. 9, 2012, issued as U.S. Pat. No. 8,783,541 on Jul. 22, 2014, the disclosure of which is incorporated by reference herein; U.S. Pub. No. 2012/0211546, entitled "Drive Interface for Operably Coupling a Manipulatable Surgical Tool to a Robot," published Aug. 23, 2012, issued as U.S. Pat. No. 8,479,969 on Jul. 9, 2013; U.S. Pub. No. 2012/0138660, entitled "Robotically-Controlled Cable-Based Surgical End Effectors," published Jun. 7, 2012, issued as U.S. Pat. No. 8,800,838 on Aug. 12, 2014, the disclosure of which is incorporated by reference herein; and/or U.S. Pub. No. 2012/0205421, entitled "Robotically-Controlled Surgical End Effector System with Rotary Actuated Closure Systems," published Aug. 16, 2012, issued as U.S. Pat. No.

8,573,465 on Nov. 5, 2013, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical stapler end effector assembly, the end effector assembly comprising:
   (a) a staple cartridge, wherein the staple cartridge comprises:
      (i) a plurality of staples, and
      (ii) a deck defining a plurality of openings, wherein the staple cartridge is operable to drive the staples through the openings of the deck;
   (b) an anvil, wherein the anvil is movable from an open position toward the staple cartridge to reach a closed position, wherein the anvil includes an underside having a staple forming surface configured to receive staples driven through the deck; and
   (c) a buttress assembly, wherein the buttress assembly comprises:
      (i) a buttress body having an exterior surface, wherein the buttress body extends along a horizontal plane and defines a length,
      (ii) an adhesive material, wherein the adhesive material is configured to removably secure the buttress body to the deck of the staple cartridge or the underside of the anvil,
      (iii) a first plurality of reinforcement strands woven through the buttress body in a plurality of discrete regions,
      (iv) a second plurality of reinforcement strands disposed on the exterior surface of the buttress body and extending along the length of the buttress body, and
      (v) a third plurality of reinforcement strands disposed on the exterior surface of the buttress body and extending transversely relative to the length of the buttress body;
   wherein at least one of the second plurality of reinforcement strands and at least one of the third plurality of reinforcement strands intersect at a locus disposed on an imaginary axis, wherein the imaginary axis is orthogonal to the horizontal plane of the buttress body and passes through at least one of the plurality of discrete regions.

2. The surgical stapler end effector assembly of claim 1, wherein the adhesive material comprises a pressure sensitive adhesive.

3. The surgical stapler end effector assembly of claim 1, wherein the reinforcement strands comprise polyglactin 910.

4. The surgical stapler end effector assembly of claim 1, wherein the buttress body comprises a pair of portions laterally spaced apart from each other by a gap.

5. The surgical stapler end effector assembly of claim 4, wherein at least one of the third plurality of reinforcement strands extends across the gap.

6. The surgical stapler end effector assembly of claim 1, wherein the buttress assembly further comprises an intermediate layer positioned between the buttress body and the adhesive material, wherein the intermediate layer is impermeable or semi-impermeable.

7. The surgical stapler end effector assembly of claim 6, wherein at least one of the reinforcement strands is positioned on or through the intermediate layer.

8. The surgical stapler end effector assembly of claim 1, wherein the buttress assembly further comprises a film layer positioned over the adhesive material, wherein the film layer is impermeable.

9. The surgical stapler end effector assembly of claim 8, wherein the film layer is positioned over the plurality of reinforcement strands.

10. The surgical stapler end effector assembly of claim 8, wherein the film layer defines a plurality of pockets configured to contain the adhesive material in a plurality of discrete regions.

11. The surgical stapler end effector assembly of claim 10, further comprising a retainer assembly configured to releasably hold the buttress assembly, wherein the retainer assembly comprises a plurality of protrusions configured to engage the buttress assembly at locations corresponding to the discrete regions of the adhesive material.

12. The surgical stapler end effector of claim 1, wherein each staple comprises a crown and a pair of legs, wherein at least one of the reinforcement strands is configured to engage either the crown or at least one of the legs of the staples.

13. A surgical stapler end effector assembly, the end effector assembly comprising:
(a) a staple cartridge, wherein the staple cartridge comprises:
 (i) a plurality of staples, and
 (ii) a deck, wherein the staple cartridge is operable to drive the staples through the deck;
(b) an anvil, wherein the anvil is movable from an open position toward the staple cartridge to reach a closed position, wherein the anvil includes an underside having staple forming surface configured to receive staples driven through the deck; and
(c) a buttress assembly, wherein the buttress assembly comprises:
 (i) a buttress body comprising a pair of portions laterally spaced apart from each other by a gap,
 (ii) an adhesive material, wherein the adhesive material is configured to removably secure the buttress body to the deck of the staple cartridge or the underside of the anvil, and
 (iii) a first plurality of reinforcement strands woven through the buttress body in a plurality of discrete regions,
 (iv) a second plurality of reinforcement strands disposed on an exterior surface of the buttress body and extending along a length of the buttress body, and
 (v) a third plurality of reinforcement strands disposed on the exterior surface of the buttress body and extending transversely relative to the length of the buttress body;
wherein at least one of the second plurality of reinforcement strands and at least one of the third plurality of reinforcement strands intersect at a locus disposed on an imaginary axis, wherein the imaginary axis is orthogonal to a horizontal plane of the buttress body and passes through at least one of the plurality of discrete regions.

14. A surgical stapler end effector assembly, the end effector assembly comprising:
(a) a staple cartridge, wherein the staple cartridge comprises:
 (i) a plurality of staples, and
 (ii) a deck, wherein the staple cartridge is operable to drive the staples through the deck;
(b) an anvil, wherein the anvil is movable from an open position toward the staple cartridge to reach a closed position, wherein the anvil includes an underside having staple forming surface configured to receive staples driven through the deck; and
(c) a buttress assembly, wherein the buttress assembly comprises:
 (i) a buttress body,
 (ii) an adhesive material, wherein the adhesive material is configured to removably secure the buttress body to the deck of the staple cartridge or the underside of the anvil,
 (iii) an impermeable layer positioned over the buttress body,
 (iv) an impermeable film laid over the impermeable layer, the film defining a plurality of pockets configured to contain the adhesive material in a plurality of discrete regions; and
 (v) a first plurality of reinforcement strands woven through the buttress body in a plurality of discrete regions,
 (vi) a second plurality of reinforcement strands disposed on an exterior surface of the buttress body and extending along a length of the buttress body, and
 (vii) a third plurality of reinforcement strands disposed on the exterior surface of the buttress body and extending transversely relative to the length of the buttress body;
wherein at least one of the second plurality of reinforcement strands and at least one of the third plurality of reinforcement strands intersect at a locus disposed on an imaginary axis, wherein the imaginary axis is orthogonal to a horizontal plane of the buttress body and passes through at least one of the plurality of discrete regions.

15. The surgical stapler end effector assembly of claim 14, further comprising a retainer assembly configured to releasably hold the buttress assembly, wherein the retainer assembly comprises a plurality of protrusions configured to engage the buttress assembly at locations corresponding to the discrete regions of the adhesive material.

16. The surgical stapler end effector assembly of claim 14, wherein the reinforcement strands comprise polyglactin 910.

* * * * *